US012332507B2

(12) United States Patent
Feinbloom et al.

(10) Patent No.: US 12,332,507 B2
(45) Date of Patent: Jun. 17, 2025

(54) EXAMINATION/VISUALIZATION/COLLECTION SYSTEM WITH LIGHT ENHANCEMENT

(71) Applicant: Designs for Vision, Inc., Bohemia, NY (US)

(72) Inventors: Richard E. Feinbloom, New York, NY (US); Moty Solomon, Beit uiel (IL)

(73) Assignee: DESIGNS FOR VISION, Inc., Bohemia, NY (US)

( * ) Notice: Subject to any disclaimer, the term of this patent is extended or adjusted under 35 U.S.C. 154(b) by 0 days.

(21) Appl. No.: 18/771,532

(22) Filed: Jul. 12, 2024

(65) Prior Publication Data

US 2024/0369855 A1    Nov. 7, 2024

Related U.S. Application Data

(63) Continuation-in-part of application No. 18/510,465, filed on Nov. 15, 2023, which is a
(Continued)

(51) Int. Cl.
*G02C 7/10* (2006.01)
*A61B 1/00* (2006.01)
(Continued)

(52) U.S. Cl.
CPC .......... *G02C 7/086* (2013.01); *A61B 1/00188* (2013.01); *A61B 1/24* (2013.01);
(Continued)

(58) Field of Classification Search
CPC .. G02B 21/18–22; G02B 23/04; G02B 23/08; G02B 23/10; G02B 23/105;
(Continued)

(56) References Cited

U.S. PATENT DOCUMENTS 2,246,817 A    6/1941   Sauer
2,986,969 A    6/1961   Mucheryan
(Continued)

FOREIGN PATENT DOCUMENTS

JP         2009098570 A  *  5/2009  ............. A61B 90/20
JP      WO2022259840         5/2022
(Continued)

OTHER PUBLICATIONS

English Machine Translation of JP-2009098570-A (Year: 2009).*
(Continued)

*Primary Examiner* — Nicholas R. Pasko
(74) *Attorney, Agent, or Firm* — Law Office of Carl Giordano, PC

(57) ABSTRACT

A user-wearable examination/visualization/collection system with light enhancement comprising a carrier suitable for the retention of a lighting assembly and a viewing and collection system is presented wherein images or video of objects may be collected under natural (e.g., white) light and/or non-visible light (e.g., IR, UV) conditions, processed and presented to a user on a local display. Further disclosed are lighting assemblies that provide for the light necessary to collect images different lighting conditions and optical filtering that allows for a limitation of the light viewable and collected.

19 Claims, 42 Drawing Sheets

Related U.S. Application Data continuation-in-part of application No. 18/102,747, filed on Jan. 29, 2023, now Pat. No. 12,038,630.

(60) Provisional application No. 63/661,264, filed on Jun. 18, 2024, provisional application No. 63/526,588, filed on Jul. 13, 2023, provisional application No. 63/426,367, filed on Nov. 18, 2022.

(51) Int. Cl.
| | |
|---|---|
| *A61B 1/24* | (2006.01) |
| *A61B 90/00* | (2016.01) |
| *G02B 25/00* | (2006.01) |
| *G02C 7/08* | (2006.01) |
| *G02C 9/04* | (2006.01) |

(52) U.S. Cl.
CPC ............ *A61B 90/361* (2016.02); *A61B 90/37* (2016.02); *G02B 25/004* (2013.01); *G02B 25/007* (2013.01); *G02B 25/008* (2013.01); *G02C 7/10* (2013.01); *G02C 9/04* (2013.01); *A61B 2090/3616* (2016.02); *A61B 2090/372* (2016.02); *A61B 2090/373* (2016.02)

(58) Field of Classification Search
CPC ...... G02B 23/12; G02B 23/125; G02B 23/14; G02B 25/001; G02B 25/004; G02B 25/007; G02B 25/008; G02B 25/02; G02B 27/106; G02B 27/108; G02B 27/14; G02B 27/141; G02B 27/142; G02B 27/143; G02B 27/144; G02B 27/149; G02B 27/126; G02B 27/16; G02B 27/283; G02B 13/16; G02C 7/086; G02C 7/10; G02C 9/04

See application file for complete search history.

(56) References Cited

U.S. PATENT DOCUMENTS

| | | | |
|---|---|---|---|
| 3,273,456 A | 9/1966 | Feinbloom | |
| 3,519,339 A | 7/1970 | Hutchinson | |
| 4,511,225 A | 4/1985 | Lipson | |
| 4,544,250 A * | 10/1985 | Tanaka | G02B 13/00 396/73 |
| 5,018,846 A | 5/1991 | Gutridge | |
| 5,042,930 A * | 8/1991 | Hutt | G02B 7/002 348/E5.029 |
| 5,078,469 A * | 1/1992 | Clark | A61B 90/361 351/158 |
| 5,162,647 A | 11/1992 | Field, Jr. | |
| 5,331,357 A | 7/1994 | Cooley | |
| 5,668,661 A | 9/1997 | Tomioka | |
| 5,742,434 A | 4/1998 | Carmeli | |
| 6,546,208 B1 | 4/2003 | Costales | |
| 6,697,195 B2 | 2/2004 | Weber | |
| 7,409,792 B2 | 8/2008 | March | |
| 7,682,042 B2 | 3/2010 | Feinbloom | |
| 7,690,806 B2 | 4/2010 | Feinbloom | |
| 8,120,847 B2 | 2/2012 | Chang | |
| 8,215,791 B2 | 7/2012 | Feinbloom | |
| 8,851,709 B2 | 10/2014 | Feinbloom | |
| 8,922,624 B2 | 12/2014 | Betorius | |
| 9,470,908 B1 | 10/2016 | Frankel | |
| RE46,463 E | 7/2017 | Feinbloom | |
| 9,720,260 B2 | 8/2017 | Clailung | |
| 9,791,138 B1 | 10/2017 | Feinbloom | |
| 10,061,115 B2 | 8/2018 | Feinbloom | |
| 10,132,483 B1 | 11/2018 | Feinbloom | |
| 10,146,039 B2 | 12/2018 | Schnitzler | |
| 10,146,063 B2 | 12/2018 | Kammans | |
| 10,215,977 B1 | 2/2019 | Feinbloom | |
| 10,240,769 B1 | 3/2019 | Braganca | |
| 10,247,384 B1 | 4/2019 | Feinbloom | |
| 10,288,886 B2 | 5/2019 | Jannard | |
| 10,288,908 B2 | 5/2019 | Calilung | |
| 10,330,927 B2 * | 6/2019 | Hoegele | G02B 21/361 |
| 10,437,041 B1 | 10/2019 | Feinbloom | |
| 10,698,196 B2 * | 6/2020 | Davidi | G02B 25/008 |
| 10,895,735 B1 | 1/2021 | Feinbloom | |
| 11,099,376 B1 | 8/2021 | Steier | |
| 11,119,309 B1 | 9/2021 | Feinbloom | |
| 11,193,662 B1 | 12/2021 | Feinbloom | |
| 11,231,165 B1 | 1/2022 | Feinbloom | |
| 11,359,798 B2 | 6/2022 | Feinbloom | |
| 11,719,925 B2 | 8/2023 | Steier | |
| 11,740,449 B2 | 8/2023 | Feinbloom | |
| 12,038,630 B1 * | 7/2024 | Feinbloom | G02B 23/14 |
| 2001/0005281 A1 | 6/2001 | Yu | |
| 2005/0078364 A1 | 4/2005 | Tseng | |
| 2007/0097703 A1 * | 5/2007 | Goldfain | F21V 13/14 362/800 |
| 2008/0219654 A1 | 9/2008 | Border | |
| 2009/0040600 A1 | 2/2009 | Vojtech | |
| 2009/0073558 A1 | 3/2009 | Jacobs | |
| 2010/0053311 A1 | 3/2010 | Luber | |
| 2010/0053540 A1 | 3/2010 | Blayden | |
| 2010/0182418 A1 * | 7/2010 | Jess | G02B 27/145 348/E7.091 |
| 2010/0210951 A1 | 8/2010 | Rahman | |
| 2010/0305436 A1 | 12/2010 | Chen | |
| 2011/0270035 A1 | 11/2011 | Gono | |
| 2012/0120636 A1 | 5/2012 | Wilt | |
| 2012/0275140 A1 | 11/2012 | Feinbloom | |
| 2013/0100534 A1 | 4/2013 | Jannard | |
| 2014/0036356 A1 | 2/2014 | Feinbloom | |
| 2014/0210972 A1 | 7/2014 | On | |
| 2014/0362343 A1 * | 12/2014 | Hauger | G02B 21/16 600/114 |
| 2015/0123880 A1 | 5/2015 | Tan | |
| 2015/0146290 A1 | 5/2015 | Chang | |
| 2015/0253589 A1 * | 9/2015 | Finkman | G02B 25/008 359/240 |
| 2017/0143442 A1 | 5/2017 | Tesar | |
| 2017/0340405 A1 * | 11/2017 | Aferzon | A61B 90/50 |
| 2018/0024341 A1 * | 1/2018 | Romanowski | G02B 21/06 359/385 |
| 2018/0224674 A1 | 8/2018 | Carabin | |
| 2018/0324277 A1 | 11/2018 | Wang | |
| 2021/0038339 A1 * | 2/2021 | Yu | G02B 25/008 |
| 2021/0306599 A1 | 9/2021 | Piece | |
| 2021/0396988 A1 | 12/2021 | Steier | |
| 2024/0168275 A1 * | 5/2024 | Feinbloom | G02B 25/004 |

FOREIGN PATENT DOCUMENTS

| | | |
|---|---|---|
| WO | WO199215039 | 9/1992 |
| WO | WO-2011002209 A2 * | 1/2011 ........... A61B 90/361 |
| WO | WO202205404 | 1/2022 |

OTHER PUBLICATIONS

International Search Report and Written Opinion of the International Searching Authority, Dated Mar. 21, 2024.

Notification of Transmittal of the International Search Report and the Written Opinion of the International Searching Authority or the Declaration, Jan. 29, 2025 (Jan. 29, 2025).

* cited by examiner

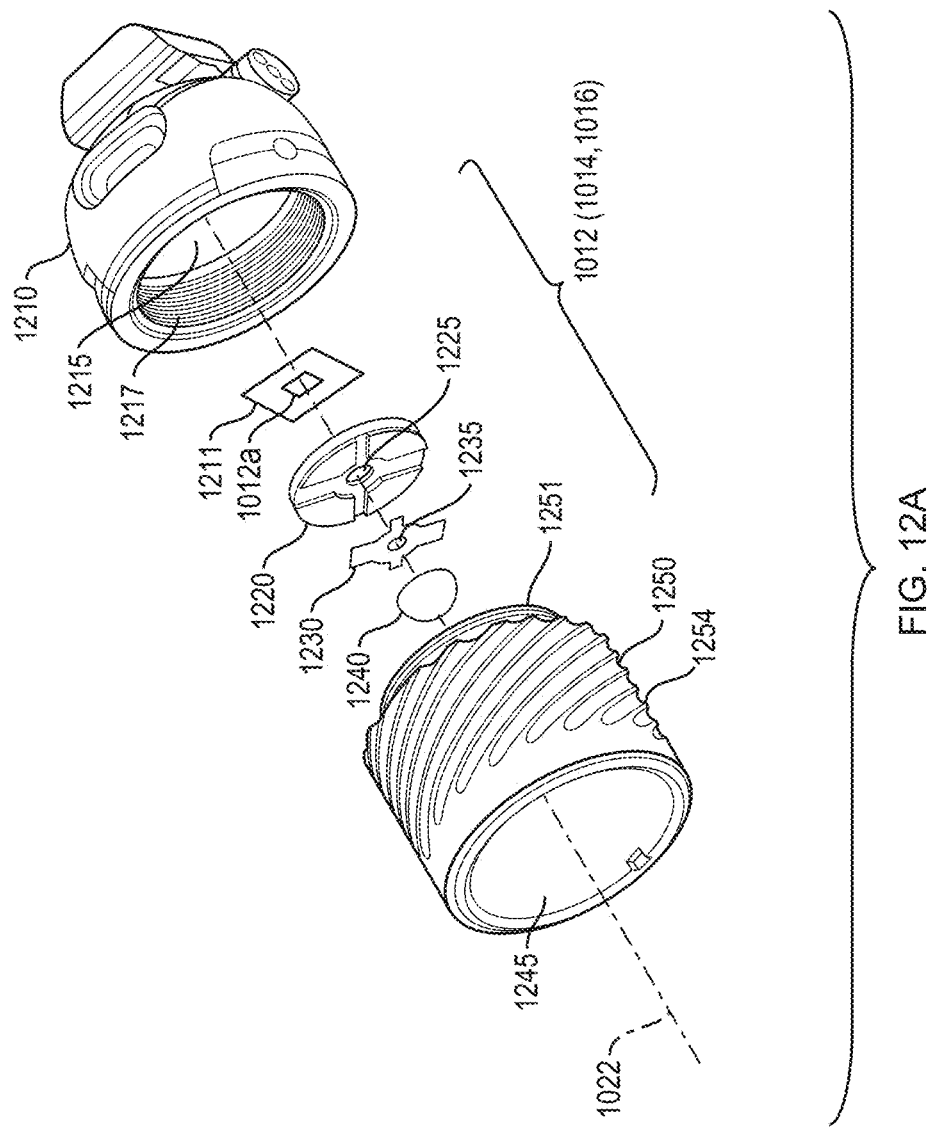

EXAMINATION/VISUALIZATION/COLLECTION SYSTEM WITH LIGHT ENHANCEMENT

CLAIM OF PRIORITY

This application claims, pursuant to 35 USC 119, claims priority to, and the benefit of, the earlier filing date of patent application Ser. No. 63/661,264 filed on Jun. 18, 2024, and pursuant to 35 USC 120, as a Continuation-in-part application, priority to, and the benefit of, the earlier filing date of patent application Ser. No. 18/510,465 filed on Nov. 15, 2023, which claimed pursuant to 35 USC 119, priority to, and the benefit of the earlier filing date of U.S. provisional patent application Ser. No. 63/526,588 filed on Jul. 13, 2023 and further claimed, pursuant to 35 USC 120, as a Continuation-in-part application, priority to, and the benefit of the earlier filing date of, patent application Ser. No. 18/102,747 filed on Jan. 29, 2023, which claimed pursuant to 35 USC 119, priority to and the benefit of, the earlier filing date of provisional application Ser. No. 63/425,367 filed on Nov. 18, 2022, the contents of all of which are incorporated by reference, herein.

RELATED APPLICATIONS

This application is related to, and incorporates by reference, the content and disclosure, in their entirety, of U.S. Pat. No. 11,231,165—Multiple Light Source Configuration; U.S. Pat. No. 11,099,376—User Wearable Fluorescence Enabled Visualization System; U.S. Pat. No. 10,895,735—Magnification Devices with Filtering and Method for Selection of Said Filters; U.S. Pat. No. 10,061,115—Magnification Device and Assembly; U.S. Pat. No. 10,247,384—LED Lighting Element and Method of Manufacturing Same; and U.S. Pat. No. 7,690,806—Illuminating Headlamp Providing Substantially Uniform Illumination and from those patents from which they depend as Continuation, Divisional and Continuation-in-Part and the patents and patent applications that are dependent as Continuation, Divisional, Continuation-in-part application and ReIssues, therefrom.

BACKGROUND OF THE INVENTION

Field of the Invention

This invention relates to the field of optical devices and, in particular, to an optical examination device incorporating image and video capturing and displaying, in at least one of the ultra-violet light wavelength range, a visible light wavelength range and an infra-red light wavelength range.

Background Information

Head-borne or wearable eyewear utilizing telescopic lens provide a practitioner with a magnified view of an area that the practitioner is viewing. Whether this is a patient's mouth, as in the case of a dentist, or in a body cavity, as in the case of a surgeon, the magnified view enables the practitioner to both see details that may not be viewable without the telescopic lens and provide more precise location of their instruments.

In addition, image capturing devices (e.g., digital cameras) have allowed for the capturing and memorializing of the images (photographic and/or video) viewed by a practitioner.

Smart microscopes, such as the Axiolab 5, by Carl Ziess, use microscope cameras to capture magnified images of an area being viewed through the microscope. And further provide for the identification of areas of infection that remain doing a surgical or dental procedure.

However, such devices are large, stationary and expensive and generally used by pathologists to analyze segments that may be taken outside of the area where the procedure is occurring. The smart microscope, while providing for the real-time capturing of a magnified image during a procedure (e.g., open-heart surgery) are expensive to install and operate, and further require skilled technical support to maintain them properly.

Hence, there is a need in the industry for the capturing of photographic and/or video images, in real-time, during dental or medical procedures (or other fields where close inspection and viewing is required) that provides for the real-time presentation of image and/or information data to the user.

SUMMARY OF THE INVENTION

Disclosed is a user-wearable device comprising telescopic lenses and image capturing devices that allows for the viewing of a magnified image of an object and the capturing of images of the object with a same or substantially a same magnification level as that the user sees under the same or different lighting conditions and a display system that provides digital representations of the images collected to the user in real-time.

Disclosed is a user-wearable device comprising telescopic lenses and image capturing devices that allows for the capturing of images with a different magnification level then the magnification level a user sees, under the same or different lighting conditions, and a display system that provides to the user, in real-time, digital representations of the images collected.

Disclosed is a user-wearable examination, visualization and image collection system comprising a magnification system, a filtering system and a display system that allows for the viewing of an object and for the collection of images of the object under different lighting conditions and further presents, in real time, a representation of the collected images to a user, wherein the system further comprises a lighting system that provides lighting to the object.

Disclosed is a user-wearable examination, visualization and image collection system comprising a lighting system that provides light in different wavelength ranges toward an object and a user wearable device comprising a magnification device incorporating an image capture device, therein, to allow the magnified viewing of the object and the concurrent capturing of a photo or video of the magnified view of the object being viewed under different lighting conditions.

Disclosed are embodiments of a user-wearable examination, visualization and image collection system comprising a lighting system that emits light in at least one of a plurality ranges extending from ultra-violet to infra-red wavelength and a user wearable device comprising a magnification device for viewing a magnified image of an object illuminated by the emitted light and an image capture device(s) configured to collect images of the illuminated object(s) and a display system that presents the collected images to a user. In one aspect of the invention, the image capture devices may capture images of objects illuminated by light in a limited wavelength range in at least one of the ultra-violet, visible light and infra-red light (IR).

Disclosed are exemplary embodiments of a user-wearable examination, visualization and image collection system comprising a lighting system, a magnification system, a light filtering system, and image capture device system that allows for the concurrent viewing and capturing of images of an object under different lighting conditions, wherein the captured images are stitched (or merged) together to form a combined image viewable by the user.

For a better understanding of exemplary embodiments and to show how the same may be carried into effect, reference is made to the accompanying drawings. It is stressed that the particulars shown are by way of example only and for purposes of illustrative discussion of the preferred embodiments of the present disclosure and are presented to clarify the most useful and readily understood description of the principles and conceptual aspects of the invention. In this regard, no attempt is made to show structural details of the invention in more detail than is necessary for a fundamental understanding of the invention. The description taken with the drawings make apparent to those skilled in the art how the several forms of the invention may be embodied in practice.

BRIEF DESCRIPTION OF THE DRAWINGS

The advantages, nature, and various additional features of the invention will appear more fully upon consideration of the illustrative embodiments described in detail in connection with the accompanying drawings, where like or similar reference numerals are used to identify like or similar elements throughout the drawings:

FIG. 12A illustrates an exploded perspective view of a first exemplary embodiment of a lighting element incorporated into the lighting assemblies shown in FIGS. 10 and 11.

It is to be understood that the figures, which are not drawn to scale, and descriptions of the present invention described herein have been simplified to illustrate the elements that are relevant for a clear understanding of the present invention, while eliminating, for purposes of clarity, many other elements. However, because these omitted elements are well-known in the art, and because they do not facilitate a better understanding of the present invention, a discussion of such elements are not provided herein. The disclosure, herein, is directed also to variations and modifications known to those skilled in the art.

DETAILED DESCRIPTION OF THE INVENTION

As used herein, the terms "comprises", "comprising", "includes", "including", "has", "having", or any other variation thereof, are intended to cover non-exclusive inclusions. For example, a process, method, article or apparatus that comprises a list of elements is not necessarily limited to only those elements but may include other elements not expressly listed or inherent to such process, method, article, or apparatus. In addition, unless expressly stated to the contrary, the term "of" refers to an inclusive "or" and not to an exclusive "or". For example, a condition A or B is satisfied by any one of the following: A is true (or present) and B is false (or not present); A is false (or not present) and B is true (or present); and both A and B are true (or present).

The terms "a" or "an" as used herein are to describe elements and components of the invention. This is done for convenience to the reader and to provide a general sense of the invention. The use of these terms in the description, herein, should be read and understood to include one or at least one. In addition, the singular also includes the plural unless indicated to the contrary. For example, reference to a composition containing "a compound" includes one or more compounds. As used in this specification and the appended claims, the term "or" is generally employed in its sense including "and/or" unless the content clearly dictates otherwise.

All numeric values are herein assumed to be modified by the term "about," whether or not explicitly indicated. The term "about" generally refers to a range of numbers that one skill in the art would consider equivalent to the recited value (i.e., having the same function or result). In any instance, the terms "about" may include numbers that are rounded (or lowered) to the nearest significant figure.

Figure 1:
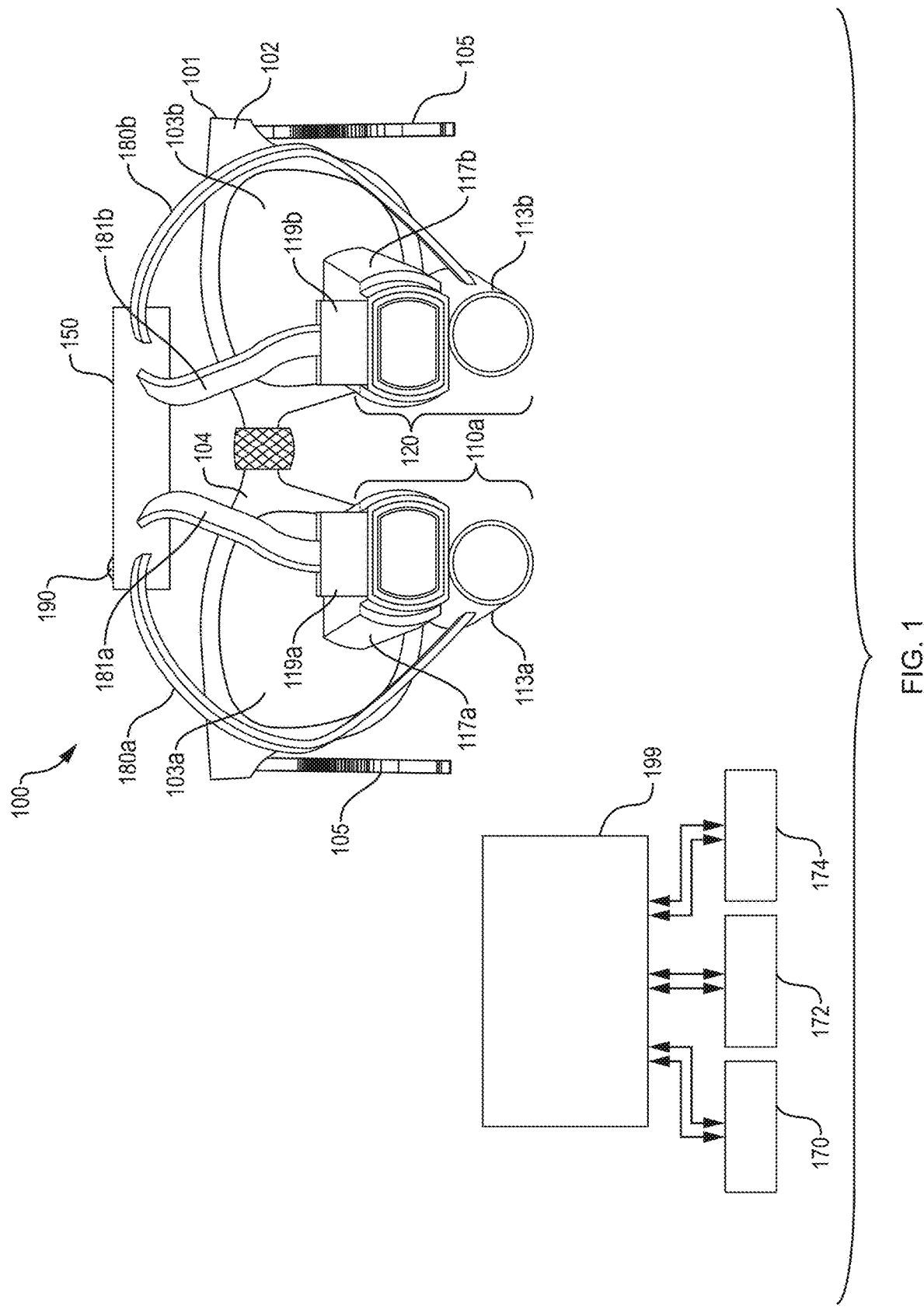
FIG. 1 illustrates a frontal view of a first exemplary embodiment of a head-borne examination/visualization system in accordance with the principles of the invention.

FIG. 1 illustrates a frontal view of a first exemplary embodiment of a head-borne examination/visualization system in accordance with the principles of the invention.

In this illustrated embodiment, examination/visualization system 100 comprises eyewear 101 comprising frame element 102 and a temple 105 extending from frame element 102. Included within frame element 102 are carrier lenses 103 (referred to as first lens 103a and second lens 103b) joined together by bridge element 104. Associated with each of the first lens 103a and the second lens 103b is visualization system 110, wherein visualization system 110 (referred to as 110a, 110b, respectively) is retained within corresponding ones of carrier lenses 103a, 103b.

Visualization system 110 comprises viewing/capturing system 120, comprising magnification device 117, image capture assembly 113 and display system 119, wherein magnification device 117 provides for a magnified view of an object within a desired field of view (FoV) or area, image capture assembly 113 provides for the capturing of images or video of the viewed object and display system 119 provides for the viewing of a magnified image (or enhanced image) of the object within the FoV or the area. In this illustrated embodiment, visualization system 110 associated with first lens 103a (referred to as 110a) comprises magnification device 117a, image capture assembly 113a and display system 119a. Similarly, visualization system 110 associated with second lens 103b (referred to as 110b) comprises magnification device 117b, image capture assembly 113b and display system 119b.

Image capture assemblies 113a, 113b may include a digital camera element (not shown), wherein a camera, including an integrated lens, is configured to convert light associated with an image of an object into electrical signals that are subsequently processed to form an image of the viewed object. Alternatively, image capture assemblies 113a, 113b may include one or more sensors, such as a charged coupled device (CCD) or a complementary metal-oxide-semiconductor (CMOS) device, that are configured to convert light associated with images of an object (in one or more wavelength ranges (e.g., ambient (i.e., light within a surrounding environment), white wavelength range, Infra-Red wavelength range, ultra-violet, color light (i.e., non-white visible light), etc.)) into electrical impulses that are used to form of an image of an object. In the configuration of a stand-alone sensor (i.e., CCD or CMOS device), a lens element (not shown) may be associated with the stand-alone sensor to allow for the convergence of light onto the sensor.

In one aspect of the invention, image capture assembly 113 may include magnification components that allow for the capturing of a magnified image of the object wherein the magnified image is of a same or a substantially same degree of magnification as that associated with the magnification device 117. In still another aspect of the invention, image capture assembly 113 may include magnification components that allow for the capturing of a magnified image of the object wherein the magnified image is magnified by a different degree of magnification that that associated with magnification device 117. In still another aspect of the invention, a further magnification system or a lens element associated with the image capture assembly 113 may be configured to increase the magnification level of the images associated with an object (e.g., a zoom lens).

Further illustrated is display system 119a, 119b, wherein information collected by image capture assemblies 113 (113a, 113b) may be provided to a practitioner or user through corresponding ones of first lens 103a and second lens 103b, respectively, in a manner that enables the practitioner to view desired data (e.g., images of the, not shown, object) without the practitioner altering their head position. Alternatively, display systems 119a, 119b may present to a practitioner bio-metric data that may be received from one or more external devices (e.g., EKG monitor, etc.).

Further illustrated is electronic assembly 150 positioned proximate to eyewear 101. Electronic assembly 150 includes electrical and electronic components (e.g., resistors, capacitors, integrated circuitry (e.g., application specific integrated circuitry (ASIC), field programmable gate array (FPGA), etc.) suitable for the transmitting, receiving and processing information for the control of an application of electrical energy to one or more of the display systems 119 and image capture assemblies 113.

Electronic assembly 150 may be connected to display system 119 and image capture assembly 113 with one or more of a wired connection. In this illustrated embodiment, display system(s) 119 are shown connected to electronic assembly 150 through wired connection 181 (181*a*, 181*b*). Similarly, image capture assembly 113 is shown connected to electronic assembly 15 through wired connection 180 (180*a*, 180*b*).

In one aspect of the invention electronic assembly 150 may further include transmitter 190, wherein images captured by image capture assembly 113 may be provided to electronic assembly 150 and presented to transceiver (i.e., transmitter/receiver) 190. Transceiver 190 may be configured to transmit the captured images or videos of an object (not shown) to a local or a remote receiving system 199 using one or more of a wired connection or a wireless connection (as will be further discussed).

Receiving system 199 may comprise one or more of a cellular phone, a laptop computer, a stand-alone server system, a cloud-based server system, a display, a storage device and other similar systems used for receiving, storing and/or displaying the information (e.g., images) provided by electronic assembly 150. In addition, receiving system 199 may include electronic components that provide for the processing of the received information to improve color, magnification, etc.

In addition, receiver 199 may further components that provide for the transmission of captured image data to one or more devices, such as remote display 170, storage system 172 and a processing system 174. Processing system 174 which may process the received data and provide a processed image to remote display 170 that includes improved color and/or magnification. Alternatively, processing system 174 may provide the processed image to receiving 199, which may also include components that provide for the transmission of the processed images to electronic circuitry 150 for subsequent presentation on displays system 119.

Although receiving system 199 is shown separated from remote display 170, storage system 172 and processing system 174, it would be recognized that receiving system 199 may be incorporated into remote display 170, storage system 172 and processing system 174 without alternating the scope of the invention claimed.

Receiving system 199 may be in wireless communication to one or more of remote display 170, storage system 172 and processing system 174 using conventional cellular and/or local area network protocols (i.e., Wi-Fi, which utilizes one or more of the IEEE 802.11 family standard protocols, near-field communication protocol (e.g., Zigbee), or BLUETOOTH,).

Alternatively, receiving system 199 may be in wired communication (not shown) with one or more of remote display 170, storage system 172 and processing system 174.

In addition, although receiving system 199 is shown in wireless communication with transmitter 190, using one or more conventional wireless communication protocols, it would be recognized that receiving system 199 may be in wired communication with transmitter 190. For example, HDMI, USB-c, etc., that may attach to a wire-ed connector used to transmit captured images/video to receiving system 199.

Alternatively, transmitter 190 may transmit the captured images directly to other types of receiving systems such as a computing system, a network server, a cloud-based server, etc. that may display the captured images on one or more of remote display 170, store the information on one or more storage system 172 and processing system 174. The transmission of the captured image through transmitter 190, may be accomplished using one or more known wireless communication protocols, as discussed.

Although a wired connection 180 is shown as providing data transfer capability between image capture assembly 113 and transmitter 190, it would be recognized that transmitter 190 may be incorporated within image capture assembly 113 to transmit captured images to, for example, the illustrated receiving system 199.

Similarly, image capture assembly 113 may be directly wired (not shown) to one or more remote devices (e.g., 170, 172, 174) that receive the captured images.

In accordance with the principles of the invention, receiver 199 may provide information (e.g., real-time data and/or image data to transmitter 190 for subsequent display on display system 119. In this case both receiving system 199 and transmitter 190 operate as transceiving systems (i.e., transmitter/receivers) that have capability to transmit and receive data wirelessly.

In this illustrated example, transmitter 190 is shown placed on electronic assembly 150.

However, it would be understood that transmitter 190 may be located in any position (e.g., a belt, a shirt collar, etc.) that may be reached by a length of wired connection 180 shown.

In accordance with the principles of the invention, images (and/or video) transmitted to system 199 may be viewed and stored in real-time while performing a procedure (e.g., dental surgery, etc.), wherein the images collected are magnified by a level comparable to, or greater than, the level of magnification of the object viewed through magnification devices 117.

In accordance with one aspect of the invention, the capture assemblies 113*a*, 113*b* associated with magnification devices 117*a*, 117*b*, respectively, may be a same device, wherein image capture assembly 113*a*, 113*b* include image capture devices (not shown) that capture and collect images (or video) under a same lighting condition. For example, a white light, a blue light or an ambient light (i.e., light within a surrounding area), etc. The images collected by image capture assemblies 113*a*, 113*b* may then be combined by receiving system 199 or processor 174 to form a stereoscopic presentation of the object or objects within the FoV of magnification devices 117. The processed images may then be provided to display systems 119*a*, 119*b* and/or remote display 170.

In accordance with another aspect of the invention, the image capture devices 270 associated with image capture assembly 113*a* and image capture assembly 113*b* may collect and process images under different lighting conditions. For example, first image capture assembly 113*a* may be configured to capture and collect images of object(s) (not shown) at the FoV of magnification devices 117 illuminated by a white light, a colored light, a natural light or an ambient light, while second image capture assembly 113*b* may be configured to capture images of the object(s) within the FoV under a different lighting condition For example, second image capture assembly 113*b* may capture images under blue light or infra-red lighting conditions. In this case the second image capture assembly 113b may include a sensor that is optimized to capture images in the desired wavelength range (i.e., blue light wavelength range, an infra-red wavelength range, etc.). Alternatively, image capture assembly 113a, 113b may each include image capture devices (i.e., sensors) that capture images of objects under both a white and a colored (e.g., blue) lighting conditions. For example, image capture device 270 may represent a sensor that is suitable for capturing images under one or both of a visible light (e.g., white light condition, non-white light condition) and a non-visible light condition (e.g., infra-red, ultraviolet).

As would be known in the art, infra-red radiation (light) is outside the normal viewing range of the human eye and, hence, the light reflected off of objects illuminated with infra-red radiation is not visible to the human eye. Hence, objects illuminated by infra-red light that are captured through the lens camera or sensor 270, which is customized to capture images in an infra-red wavelength range, may be transmitted to receiving system 199 to be post-processed to render the objects visible to a user.

In one aspect, images collected using the image capture device, which is for the purposes of this discussion associated with a white light, a natural light or an ambient light, and images collected using an infra-red image capture device may be combined, by processing in receiving system 199 and/or processing system 174, to create an enhanced image (e.g., higher contrast) that may be viewed on one or more of remote display system 170 and display system 119, and stored in storage unit 172.

In accordance with the principles of the invention, the range of light collected by image capture assemblies 113a, 113b may be determined by one or more filters that may be placed before a corresponding image capture device (wherein the term "before" refers to light entering the filter prior to the corresponding image capture device). For example, an IR image capture device may be limited by a bandpass optical filter to view light in the wavelength range of 750-900 nm, for example. In another example, the images captured by a white light image capture device or sensor 270 may be limited by the introduction of a long pass optical filter to view light wavelengths greater than a known wavelength. Alternatively, the images captured by a white light image capture device or sensor 270 may be limited by the introduction of a short pass optical filter to view light wavelengths less than a known wavelength.

Further illustrated is mounting connection 116 on bridge element 104. Mounting connection 116 provides for the attachment of one or more devices that may be incorporated into examination/visualization system 100, as will be further discussed.

Mounting connection 116 may comprise a T-slot type connection that allows for the mating of devices that include an inverse T-slot type connection. Alternatively, mounting connection 116 may comprise a snap-on or snap-fit connection that allows for the removable attachment of devices to eyewear 101, as will be discussed.

Figure 2A:
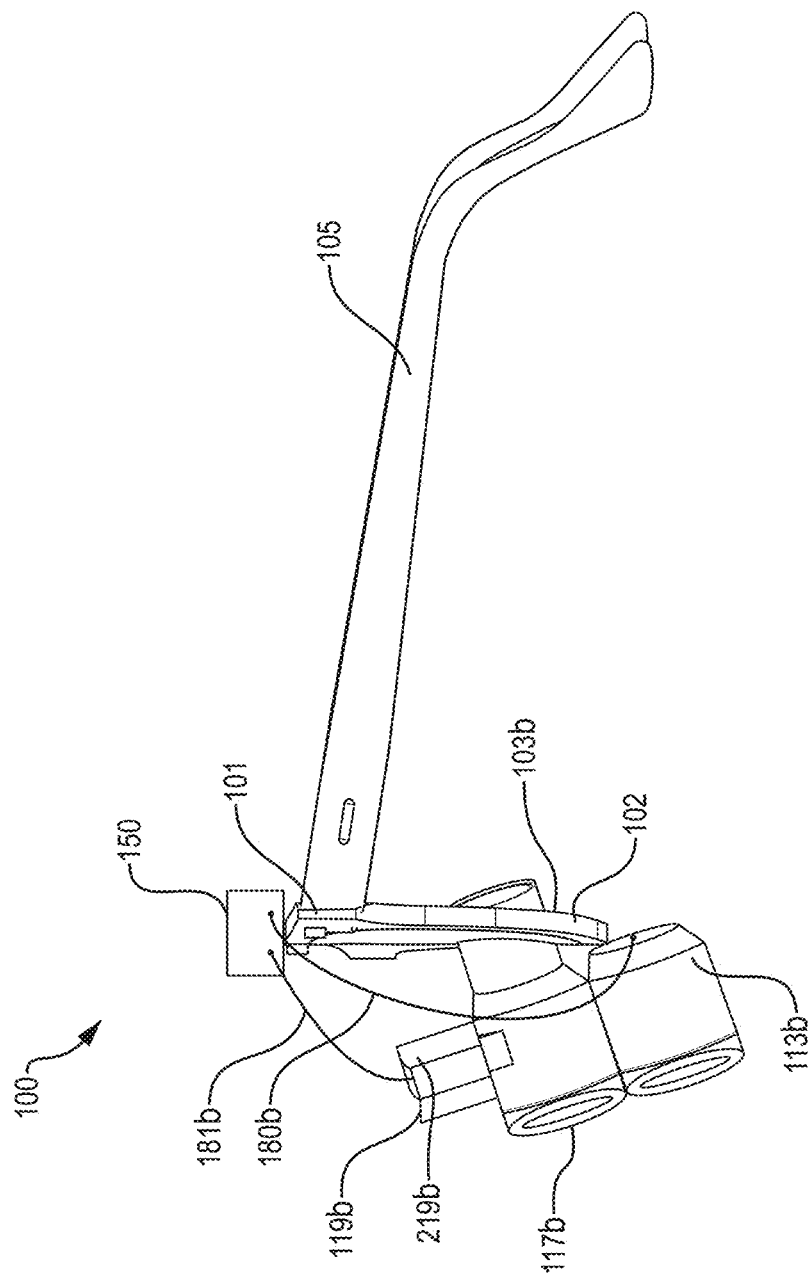
FIG. 2A illustrates a side view of the first exemplary embodiment of the examination/visualization system shown in FIG. 1.

FIG. 2A illustrates a side view of the first exemplary embodiment of the examination/visualization system shown in FIG. 1.

In this illustrated example, eyewear 101 includes frame 102 and temple 105 extending from frame 102, wherein temple 105 provides a means for retaining eyewear 101 to a practitioner.

Further illustrated is magnification device 117b extending, in this illustrated example, through second lens 103b. Retaining magnification device 117b through second lens 103b is known in the art and need not be discussed in further detail herein. Further illustrated is image capture assembly 113b, display system 119b and electronic assembly 150, wherein display system 119b and image capture assembly 113b are in wired communication (180b, 181b, respectively) with electronic assembly 150.

Display system 119b comprising display screen 219 (illustrated as 219b) positioned before lens 103b, wherein one of real-time data and images may be presented, through corresponding lens 103b, to the practitioner. Note, in this case, the term "before" refers to the position of the display screen 219 as being viewing through lens 103b.

In one aspect of the invention, wherein second lens 103b is a prescriptive or corrective lens, second lens 103b (and first lens 103a) provide necessary spherical and cylindrical correction compensation for viewing display screen 219b to assist in the focusing of information to the practitioner. Prescriptive or corrective lens are known in the art to provide compensation for the lack of the lens(es) of the practitioner's eye to focus light onto the practitioner's retina.

Alternatively, a spectral correction lens (not shown) may be incorporated onto display screen 219b to provide for one or both of spherical and cylindrical correction to assist in the focusing of data or images presented on display screen 219b to the practitioner's eye.

In one aspect of the invention, the spectral correction aspects of spectral correction lens (not shown) that would be applied to display screen 219b may be the same or similar to spectacle correction aspects that may be incorporated into lenses 103a, 103b when the user requires such vision correction (i.e., prescriptive lens).

Although discussion is made with regard to one element (113b, 117b, 119b, etc.) of eyewear 101, it would be recognized that the discussion of the 113b, 117b, 119b elements is applicable to the corresponding elements identified as 113a, 117a, 119a. Thus, a further discussion of the operation of these corresponding elements is not believed necessary for an understanding of the invention claimed.

Figure 2B:
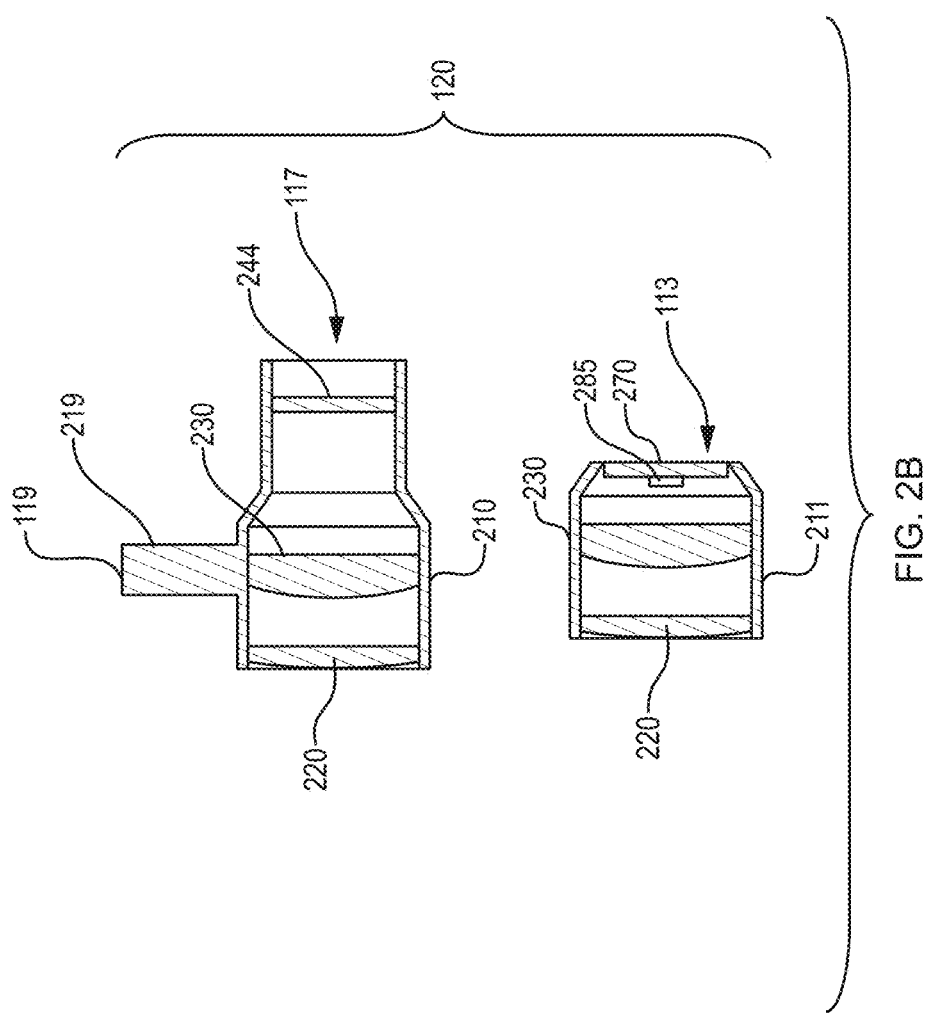
FIG. 2B illustrates a cutaway side view of the first exemplary embodiment of the examination/visualization system shown in FIG. 1.

FIG. 2B illustrates a cutaway side view of the first exemplary embodiments of the examination and visualization system shown in FIG. 1.

In this cutaway illustration of magnification device 117 and image capture assembly 113, magnification device 117 comprises a housing 210 into which are contained distal located objective lens 220 and proximal located eye-lens 230, wherein objective lens 220 and eye-lens 230 are separated by a known distance. As is known in art, the separation of objective lens 220 and eye-lens 230 creates a telescopic effect that magnifies an object viewed through the combination of objective lens 220 and eye-lens 230. The magnification level achieved by the telescopic effect is based, in part, by the distance separating objective lens 220 and eye-lens 230. For example, the greater the separation the greater the magnification level.

Further illustrated is spectral correction lens 244 that, as previously discussed, may be incorporated into magnification device 117, wherein spectral correction (or corrective) lens 244 provides for needed spherical and/or cylindrical necessary for creating an in-focus image to the practitioner.

In accordance with this illustrated aspect of the invention, image capture assembly 113 comprises second housing 211, which similar to housing 210, contains distally located objective lens 220 and proximal located eye-lens 230 separated by a distance similar or substantially similar to that shown with regard to magnification device 117. Further illustrated is image capture device 270 positioned to capture images of objects viewed by image capture assembly 113.

Image capture device 270 is configured to transform the light associated with images of object(s) through objective lens 220/eye-lens 230 into a format (e.g., electronic impulses) for subsequent transmission of the images of object(s) to electronic assembly 150. In one aspect of the invention, the transmission of the images of object(s) to electronic assembly 150 may be through a wired connection 180 (shown in FIG. 1). Alternatively, electronic elements (not shown) for the transmission of the images of objects to electronic assembly 150 by a wireless connection may be included and will be more fully discussed.

In addition to image capture device 270 is shown lens 285. Lens 285 focuses the light associated with the magnified images viewed through objective lens 220/eye-lens 230 onto the elements of image capture device 270. In one aspect of the invention, lens 285 may be integrated with image capture device 270 (e.g., a digital camera, wherein a camera is known in the art to include an optical element such as lens 285). Image capture module 270 may alternatively be represented as a stand-alone sensor (e.g., CCD) and lens 285 is a separate element that may be utilized to focus light onto the stand-alone sensor.

Although image capture assembly 113 illustrates an objective lens/eye-lens configuration that would create a same or a substantially same level of magnification of the images captured by device 270 as the images viewed by a practitioner, it would be known that image capture assembly 113 may further include objective lens/eye-lens configurations that may create different levels of magnification, without altering the scope of the invention. For example, image capture assembly 113 may possess a different level of magnification than that of magnification device 117 by the use of different lenses and/or different distances between the lenses. In addition, lens 285 may be configured to provide a further level of magnification, such that the images of objects captured by image capture assembly 113 may be the same or different than the magnification level of the images of objects viewed through magnification device 117.

Figure 3A:
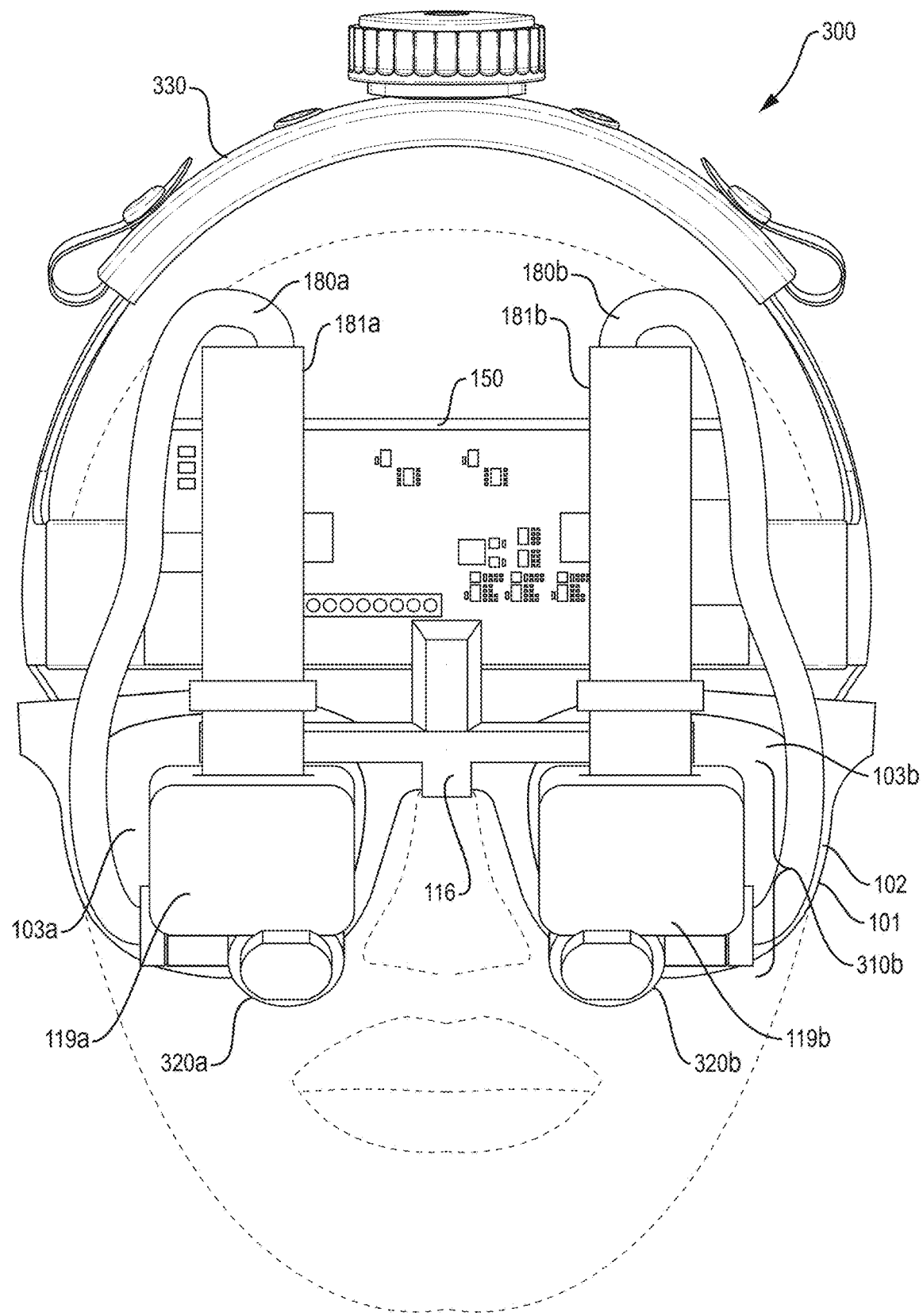
FIG. 3A illustrates a frontal view of a second exemplary embodiment of a head-worn examination/visualization system in accordance with the principles of the invention.

FIG. 3A illustrates a frontal view of a second exemplary embodiment of a head-worn examination/visualization system in accordance with the principles of the invention.

In this illustrated second exemplary embodiment, examination/visualization system 300 comprises eyewear 101 including lenses 103a, 103b and visualization system 310a, 310b, associated with each of lenses 103a, 103b, respectively. Visualization systems 310a, 310b comprise display systems 119a, 119b and viewing/capturing systems (or device) 320a, 320b, respectively, wherein viewing/capturing system 320a represents an integration of image capture assembly 113a and magnification device 117a into a single unit. Similarly, viewing/capturing system 320b represents an integration of image capture assembly 113b and magnification device 117b into a single unit.

In this illustrated exemplary second embodiment, display systems 119a, 119b are in wired connection 181a, 181b, respectively, and viewing/capturing system 320a, 320b are in wired connection 180a, 180b with electronic assembly 150. As previously discussed, images collected by the image capturing section of system 320 may be transferred to electronic assembly 150 for processing and subsequent viewing on corresponding one of display 119a, 119b, respectively. Alternatively, images collected by the image capturing section of system 320 may be transmitted to remote processor 174 for processing and subsequent viewing on display 119a, 119b. In addition, the processed images may be transmitted to remote display 170 for concurrent viewing.

As discussed, images collected by viewing/capturing systems 320a, 320b may be collected under different lighting conditions and subsequentially combined to produce a higher contrast image for viewing on the illustrated display systems as has been discussed.

Figure 3B:
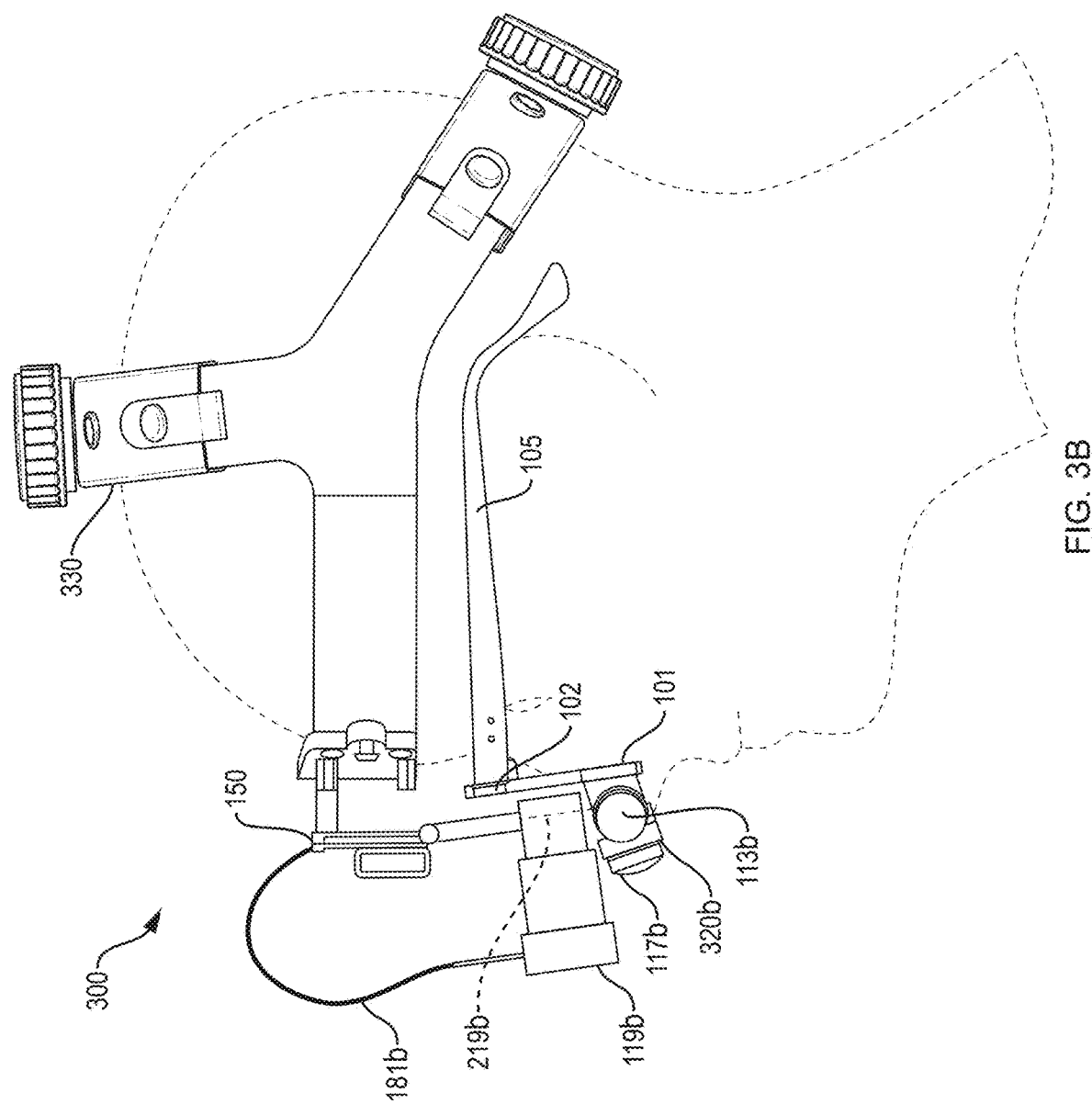
FIG. 3B illustrates a side view of the second exemplary embodiment of the head-worn examination/visualization system shown in FIG. 3A.

FIG. 3B illustrates a side view of the second exemplary embodiment of the head-worn examination/visualization system shown in FIG. 3A.

In this illustrated side view of examination/visualization system 300, temple 105 allows for the retention of system 300 to a practitioner. Further illustrated is electronic assembly 150 shown attached to headband 330 such that examination/visualization system 300 is further retained to a practitioner.

Further illustrated is display system 119b, proximate to lens 103b, in wired communication with electronic assembly 150. Display system 119b, as previously discussed, enables a practitioner to view data and/or images of objects by the image capturing section 113b of viewing/capturing system 320.

In accordance with this second embodiment of the invention, image capture element (i.e., assembly) 113b of integrated viewing/capturing system 320 offset from a direction of view of magnification element (device) 117b. In this illustrated example, image capture assembly 113 is not shown in wired connection to electronic assembly 150 to prevent obstruction of the illustrated embodiment. Although a wired communication (not shown) has been discussed, it would be recognized that the connection to electronic assembly 150 using one or more known communication protocols.

Figure 3C:
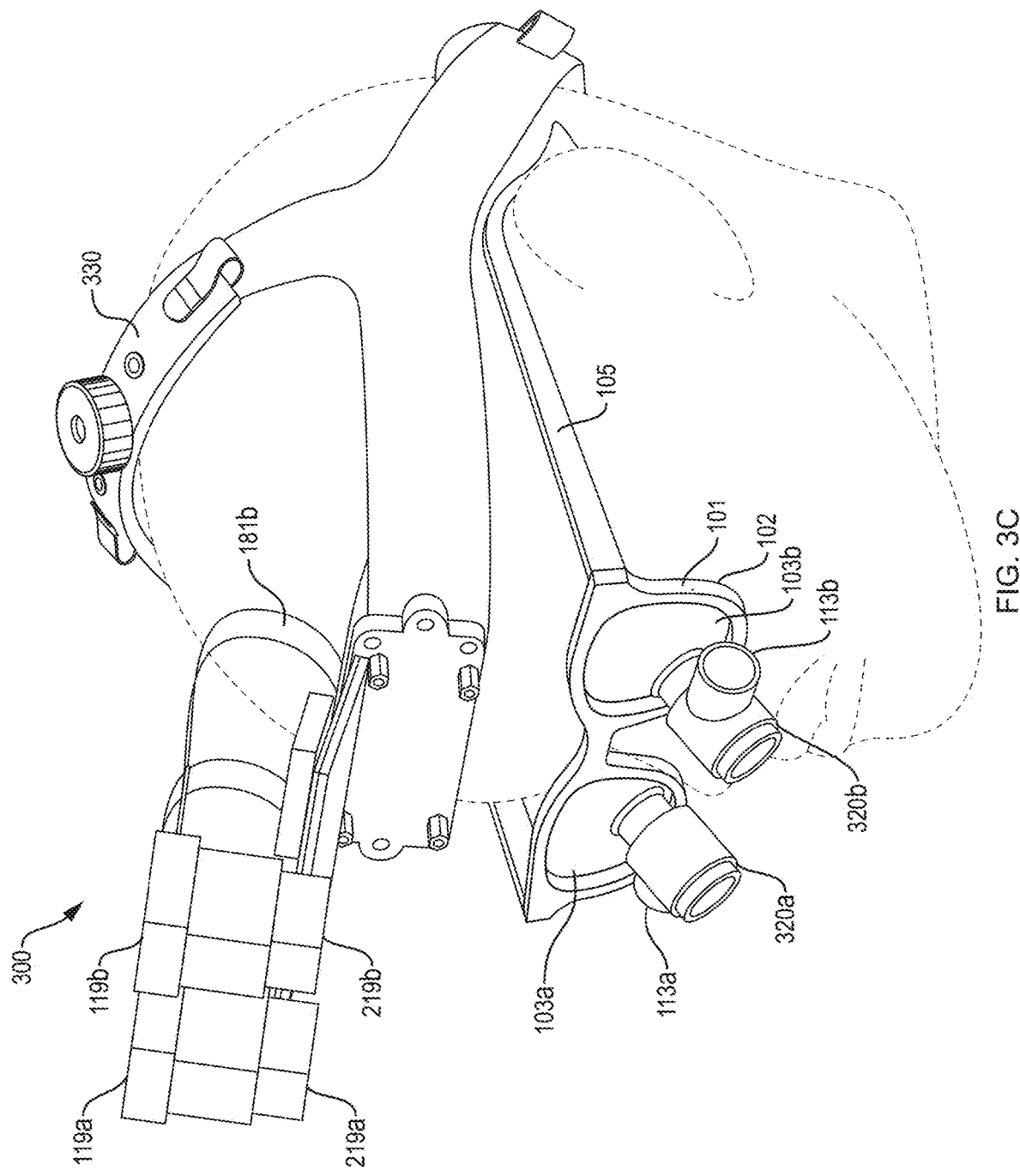
FIG. 3C illustrates a perspective view of a second aspect of the second exemplary embodiment of an examination/visualization system shown in FIG. 3A.

FIG. 3C illustrates a perspective view of a second aspect of the second exemplary embodiment of an examination/visualization system shown in FIG. 3A.

In this exemplary embodiment, examination/visualization system 300, comprises eyewear 101 including first lens 103a and second lens 103b, wherein integrated viewing/capturing systems 320a, 320b, respectively and display systems 119a, 119b are incorporated, therein.

Further shown is head strap (or head band) 330 to which is attached electronic assembly 150, wherein display systems 119a, 119b are also attached to assembly 150. In accordance with this aspect of the invention, electronic assembly 150 and display systems 119a, 119b are shown in an upward position such that display systems 119a, 119b are remote from corresponding lens 103a, 103b, respectively.

In one aspect of the invention, examination/visualization system 300 may be attached to headband by a hinge mechanism (not shown) wherein electronic assembly 150 (and display systems 119a, 119b) are held in the illustrated remote position by a locking mechanism (not shown). For example, a strut (not shown) extending from headband 330 to electronic assembly 150 may be utilized to retain electronic assembly 150 in the upward position. Alternatively, electronic assembly 150 may be held in the illustrated remote position by a detent mechanism. In still a further alternative embodiment, electronic assembly 150 may be held in the illustrated remote position by a counter-balancing element (not shown) that compensates for the weight of electronic assembly 150 and display systems 119a, 119b. In still another further alternative embodiment, electronic assembly 150 may be held in the illustrated remote position by a magnetic element.

Although not shown, it would be recognized that examination/visualization system 300 includes transmitter/receiving elements similar to that discussed with regard system 100, wherein images captured by magnification/recording devices may be transmitted to processing system 199 (see FIG. 1) for subsequent processing, storage and display, as previously discussed.

Figure 4A:
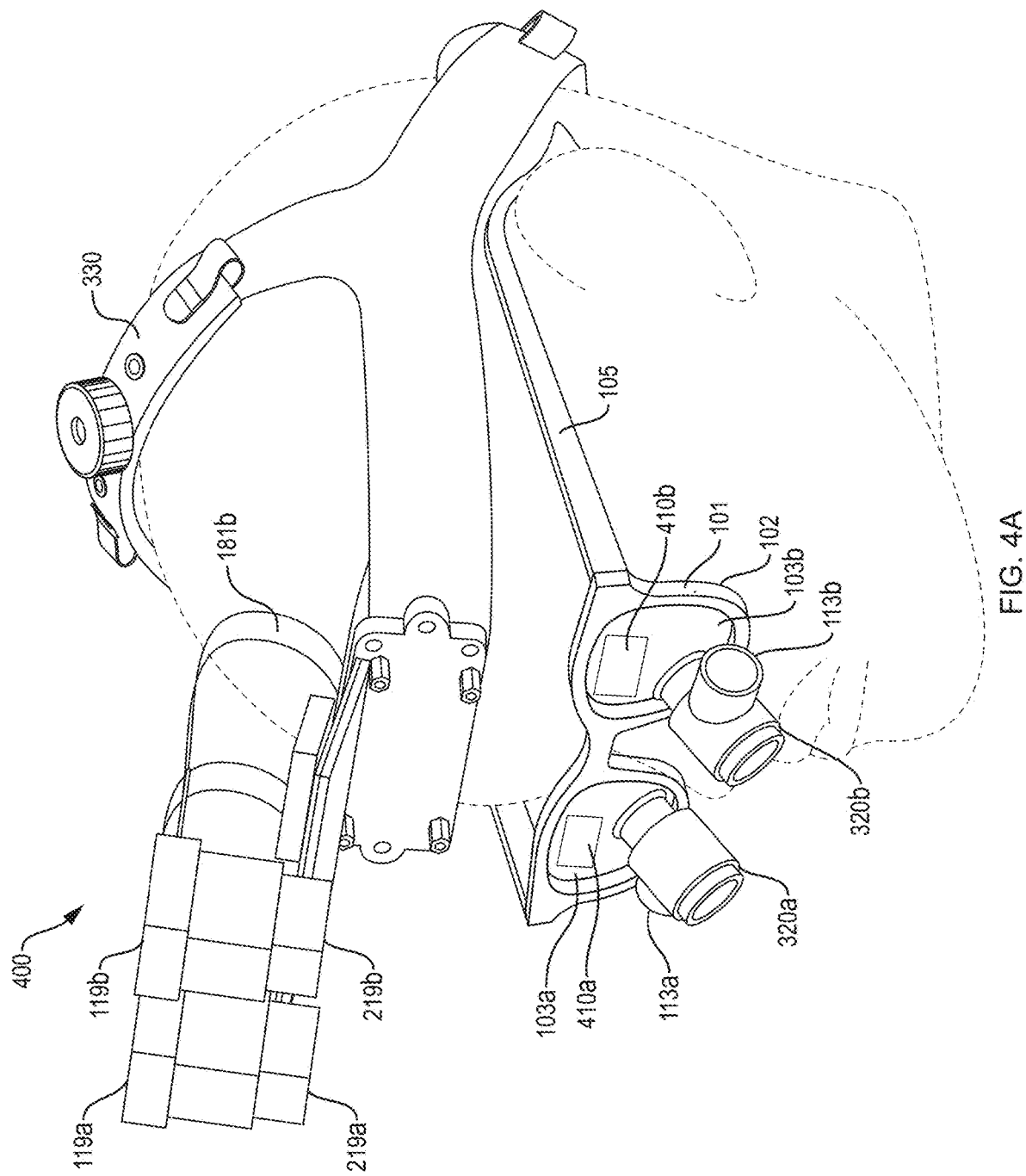
FIG. 4A illustrates a perspective view of a second aspect of the second exemplary embodiment of the examination/visualization system shown in FIG. 3A.

FIG. 4A illustrates a perspective view of a second aspect of the second exemplary embodiment of the examination/visualization system shown in FIG. 3A.

In accordance with this aspect of the invention, examination/visualization system 400 is comparable to system 300 shown in FIG. 3A and, thus a further discussion regarding those elements shown in FIG. 4A that are discussed with regarding to FIG. 3A is not believed needed to understand and o practice the invention shown in FIG. 4A.

In accordance with this aspect of the invention, first lens 103a and second lens 103b each include opening 410a, 410b, respectively, therein. Openings 410a, 410b allow for the placement of display screens 219a, 219b through lenses 103a, 103b (i.e., "through-the-lens" viewing) to place screens 219a, 219b closer to the eyes of a practitioner than shown in FIG. 3A. Such "through-the-lens" viewing provides for a clearer presentation of the information on display screens 219a, 291b, when for example, lenses 103a, 103b are tinted to reduce the intensity of light being viewed.

Figure 4B:
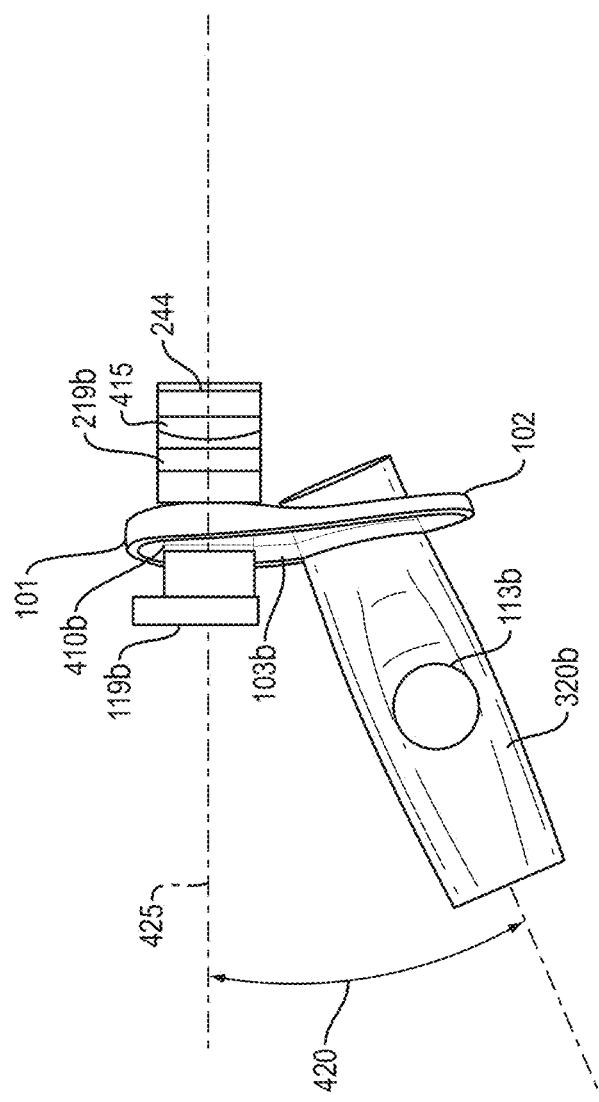
FIG. 4B illustrates a side view of the second aspect of the second exemplary embodiment of the examination/visualization system shown in FIG. 4A.

FIG. 4B illustrates a side view of the second aspect of the second exemplary embodiment of the examination/visualization system shown in FIG. 4A.

In this illustrated side view, display system 119b is shown positioned through opening 410b within lens 103b such that display screen 219b is after lens 103b, with respect to light entering lens 103b, and closer to a practitioner's eye (not shown) than lens 103b.

As shown, integrated viewing/capturing system 320b is positioned within second lens and retained at a desired angle of declination 420 with respect to a horizontal axis 425 taken with respect to eyewear 101. In one aspect of the invention, the angle of declination 420 is determined based, in part, on a desired distance from eyewear 101 that an object being viewed is in focus.

In this illustrated view, further details regarding display system 119b are discussed. For example, display system 119b includes collimating lens 415b, which is configured to have a focal point positioned on display screen 219b such that light emitted by display screen 219b is transformed to parallel light that may then be viewed by the user (not shown). In this illustrated example, collimating lens 415b is represented as a convex lens, which outputs light originating at its focal point in a parallel or a substantially parallel manner.

Although collimating lens 415b is illustrated as a convex lens, it would be understood that collimating lens 415b may be a concave lens, which similarly outputs light originating at its focal point in a parallel or substantially parallel manner.

The parallel light exiting collimating lens 415b may then be focused by lens of the practitioner's eye to provide a clear (in-focus) image to the practitioner.

In still another aspect of display system 119b, spectacle correction lens 244 may be positioned after lens 415b to receive the parallel light output by collimating lens 415b to assist in the focusing of the light (images) from display screen 219b to provide a clear (in-focus) image to the practitioner.

Spectral correction lens 244 provides for one or both spherical and cylindrical correction to present an in-focus image of the information on display 219b to the practitioner.

In one aspect of the invention, the spectral correction aspects of spectral correction lens 244 may be the same or similar to spectacle correction aspects that may be incorporated into second lens 103b when the practitioner requires such vision correction (i.e., prescriptive lens).

Figure 5A:
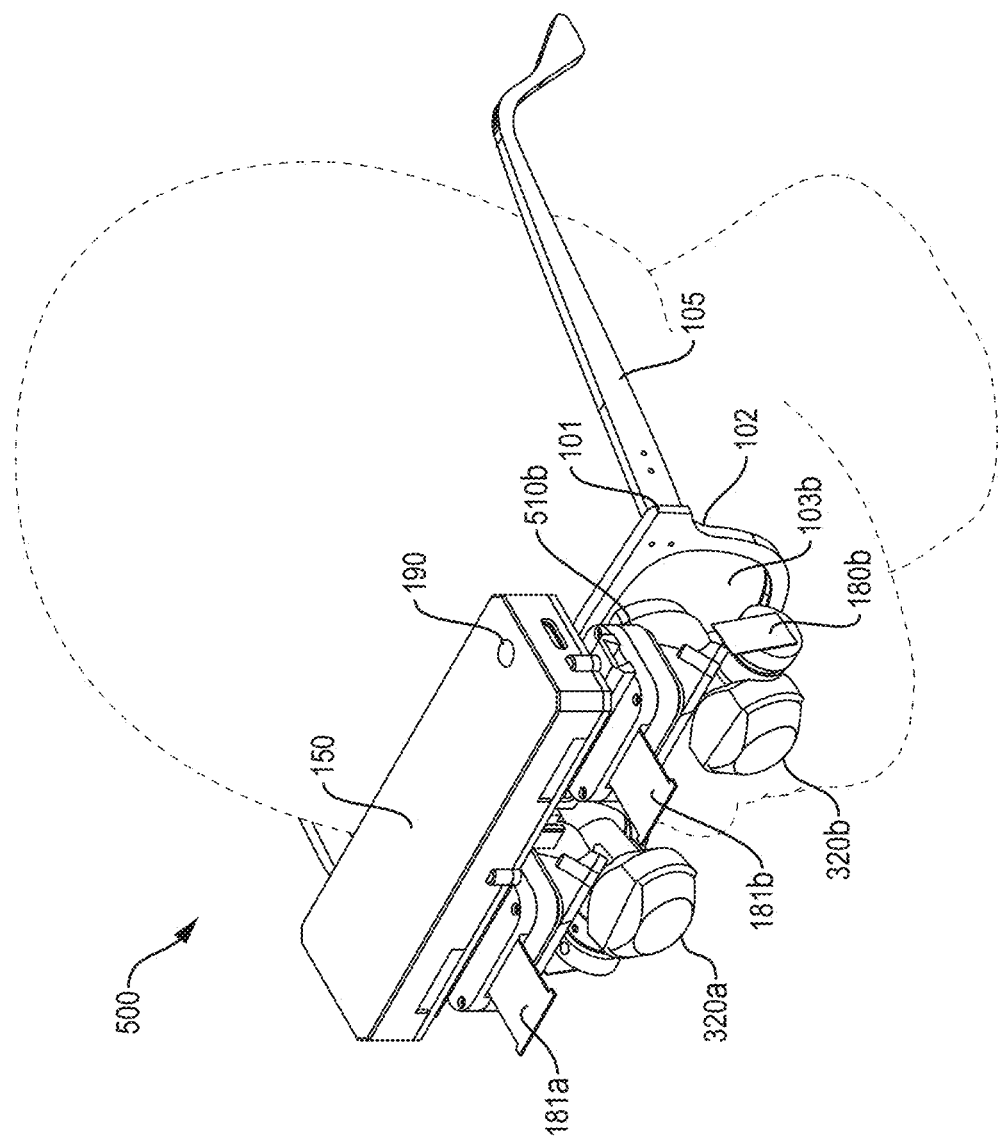
FIG. 5A illustrates a perspective view of a third exemplary embodiment of an examination/visualization system in accordance with the principles of the invention.

FIG. 5A illustrates a perspective view of a third exemplary embodiment of an examination/visualization system in accordance with the principles of the invention.

In this illustrated third exemplary embodiment, examination/visualization system 500, comprises eyewear 101 including first lens 103a and second lens 103b and corresponding integrated viewing/capturing systems 320a, 320b, respectively, incorporated therein. Further illustrated is electronic assembly 150 positioned on eyewear 101, which is in wired connection 181b (partially illustrated) between electronic assembly 150 and integrated viewing/capturing system 320b.

Eyewear 101, integrated viewing/capturing system 320, electronic assembly 150 and transmitter 190 are comparable to those elements disclosed previously. Thus, further discussion regarding these elements is not believed necessary as those skilled in the art would have an understanding of their operation from the previous discussion provided herein.

In this third exemplary embodiment, electronic assembly 150 is shown placed in a horizontal or a substantially horizontal position with respect to eyewear 101. Further shown integrated viewing/capturing system 320b and a wired connection 180b (partially illustrated) from image capture assembly 113b of integrated viewing/capturing system 320b.

In accordance with the embodiment, offset display system 510b extends downward from electronic assembly 150 to present images of objects viewed by integrated viewing/capturing system 320 to the illustrated practitioner.

Figure 5B:
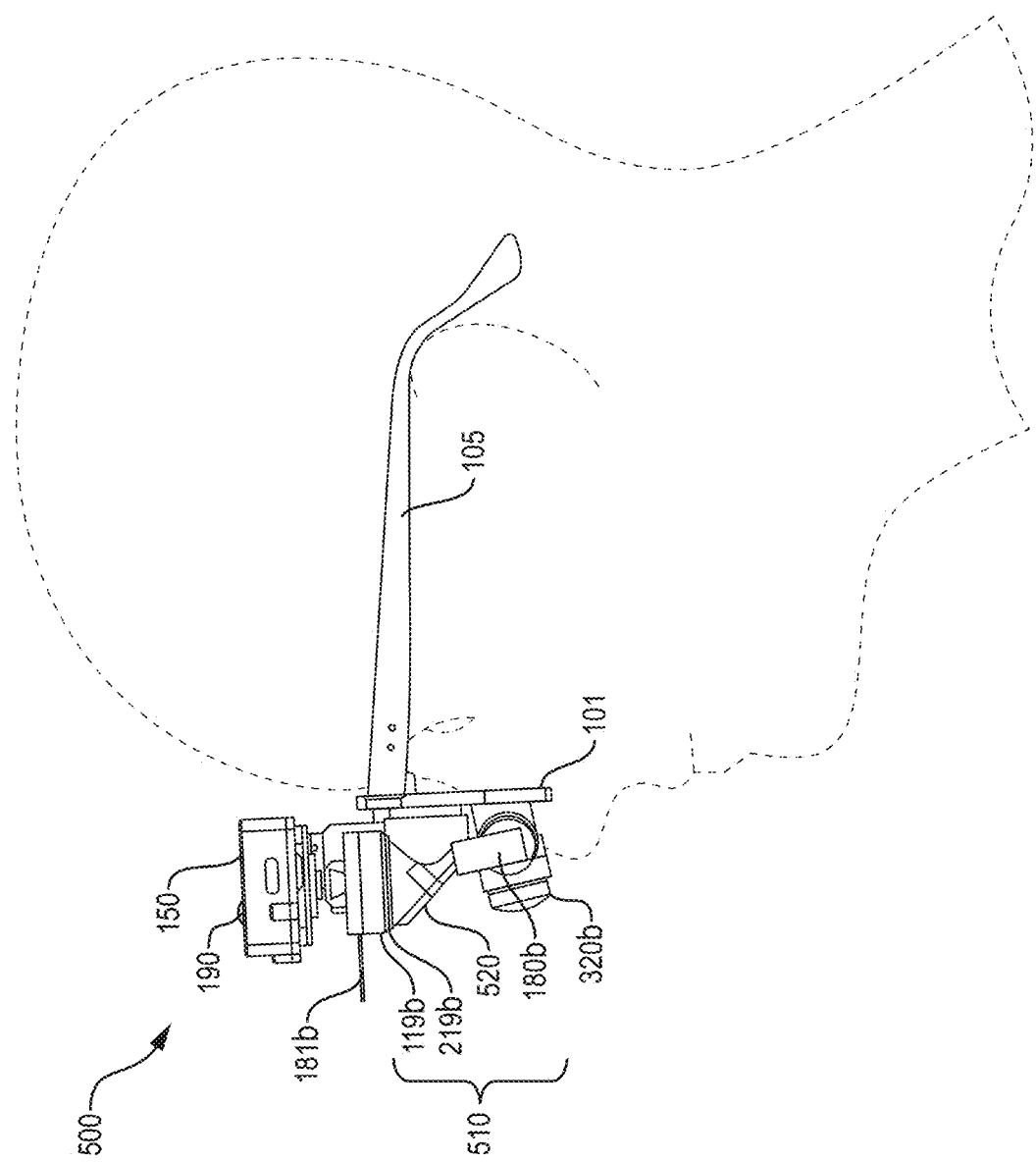
FIG. 5B illustrates a side view of the third exemplary embodiment of the examination/visualization system shown in FIG. 5A.

FIG. 5B illustrates a side view of the third exemplary embodiment of the examination/visualization system shown in FIG. 5A.

In accordance with this third exemplary embodiment, offset display system 510b comprises display system 119b, including display screen 219b (collimating lens 244 not being shown), and display director 520b oriented with respect to eyewear 101 to present light associated with images displayed on display screen 219b toward (or through) lens 103b for viewing by the practitioner.

Display director 520, which is composed of a highly reflective, non-distortive, surface (e.g., a mirror), is oriented to accommodate the orientation of display screen 219b with respect to second lens 103b. In the illustrated embodiment, display director 520b is oriented at an approximately forty-five (45) degree angle to present images displayed on display screen 219b correctly to the illustrated practitioner. However, it would be recognized that the orientation of display director 520b with respect to lens 103b is based, in part, on the orientation of display screen 219b with respect to the practitioner.

Although spectral correction lens 244 is not shown, it would be recognized, based on the prior discussion, that spectral correction lens 244 may be incorporated into display offset system 510 by those skilled in the art without undue experimentation to provide an in-focus image to a user, if necessary.

Figure 5C:
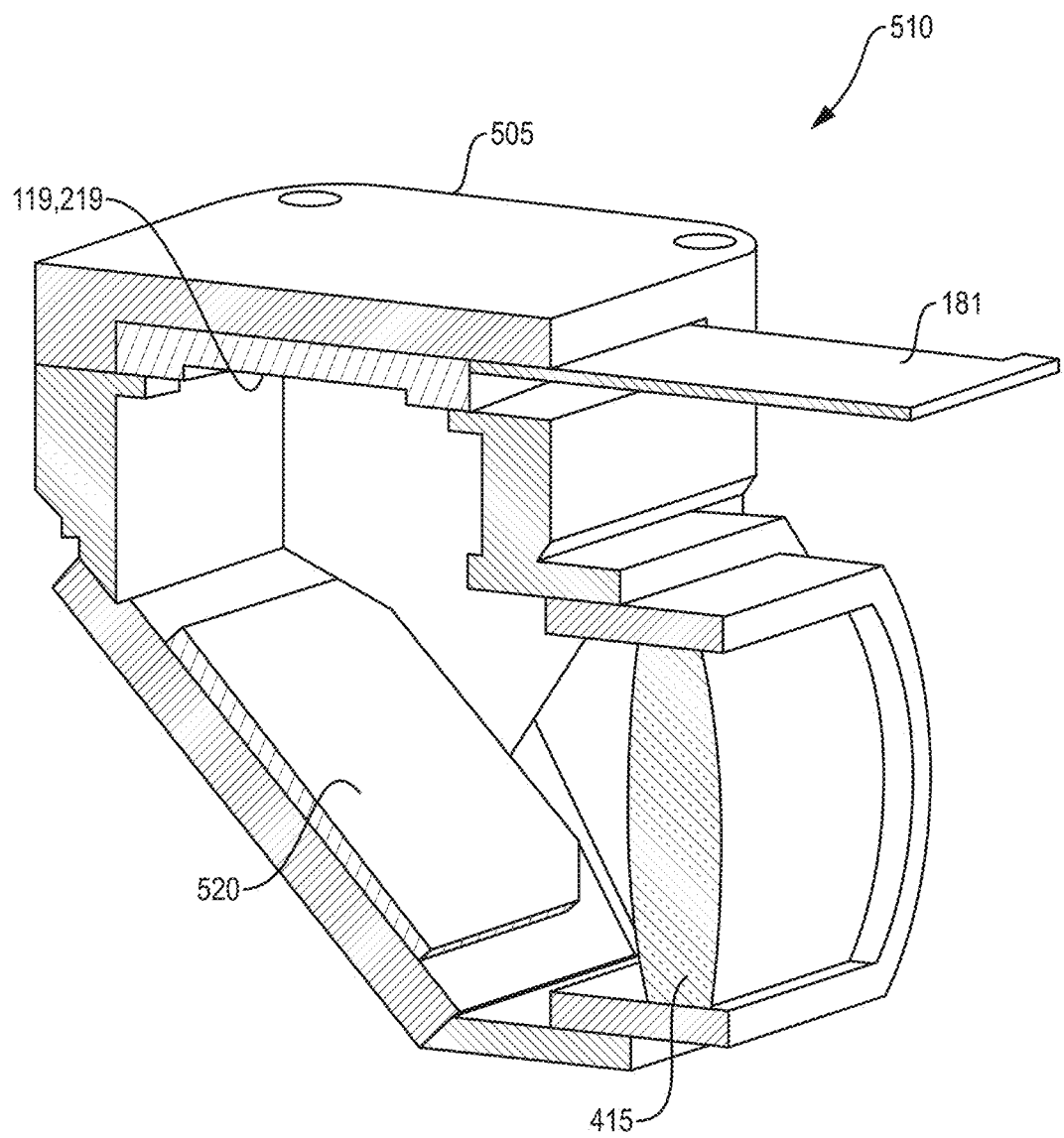
FIG. 5C illustrates a cut-away perspective view of the display offset system shown in FIGS. 5A and 5B.

FIG. 5C illustrates a cut-away perspective view of the display offset system shown in FIGS. 5A and 5B.

In accordance with the principles of this aspect of the invention, offset display system 510 comprises housing 505 into which are placed display system 119, including display screen 219, and reflective surface 520. Reflective surface 520 receives light from the images presented on display screen 219 and redirects the received light toward collimating lens 415 and subsequently toward (or through) lens 103 (not shown).

Further, partially shown, is connection 181, which provides information to be displayed onto display screen 219. As would be understood by those skilled in the art, because reflective surface 520 inverts the images presented on display screen 219, the images presented on display screen 219 may be inverted by the elements of electronic assembly 150 when provided through, in this illustrated example, wired connection 181.

Although corrective lens 244 is not shown, it would be understood by those skilled in the art, that corrective lens 244 may be incorporated in to the housing 510 to provide needed spherical and cylindrical correction of the information or images presented on display screen 219.

Figure 6A:
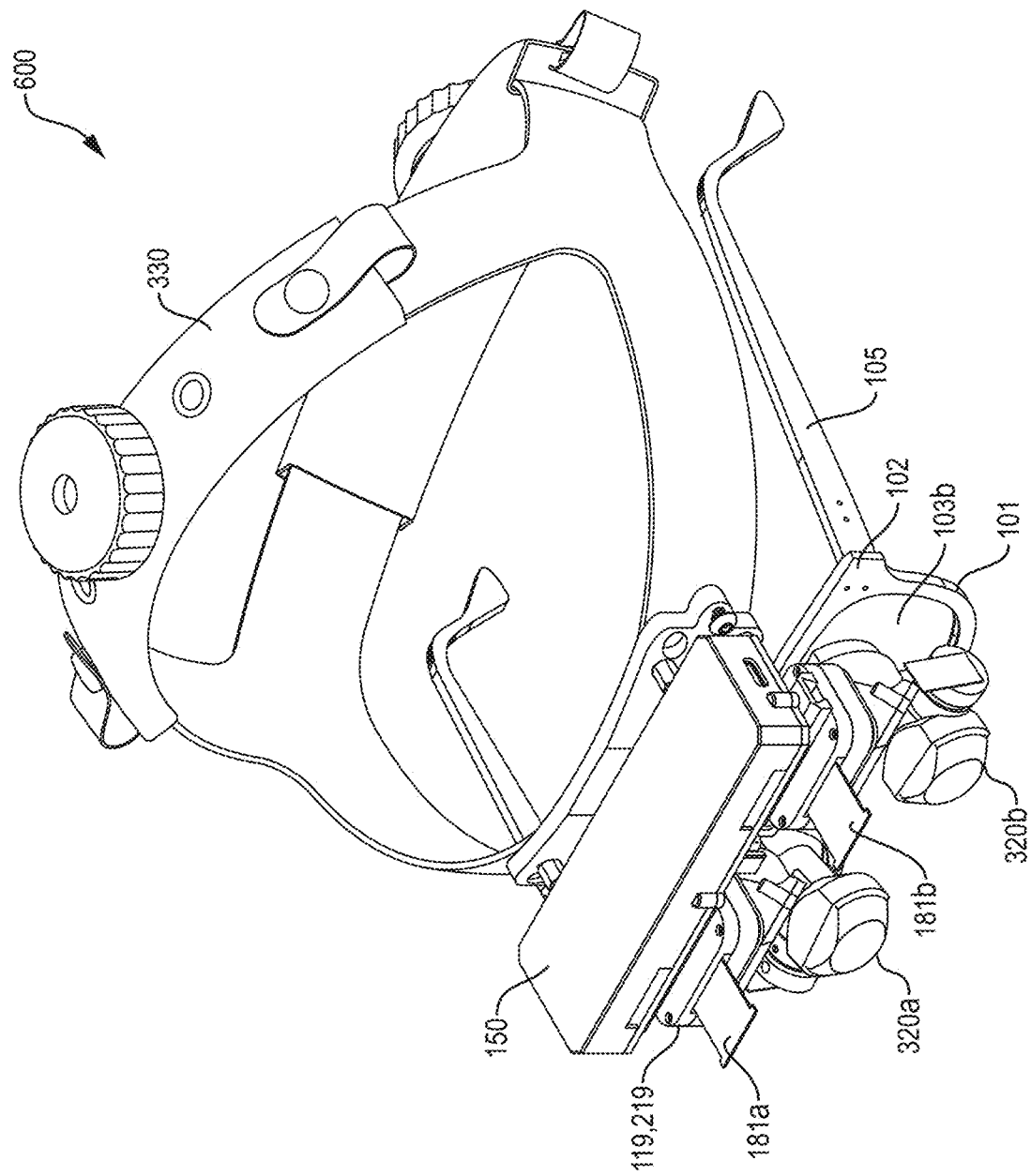
FIGS. 6A and 6B illustrate further aspects of the embodiments of an examination/visualization system shown in FIGS. 5A-5C.
Figure 6B:
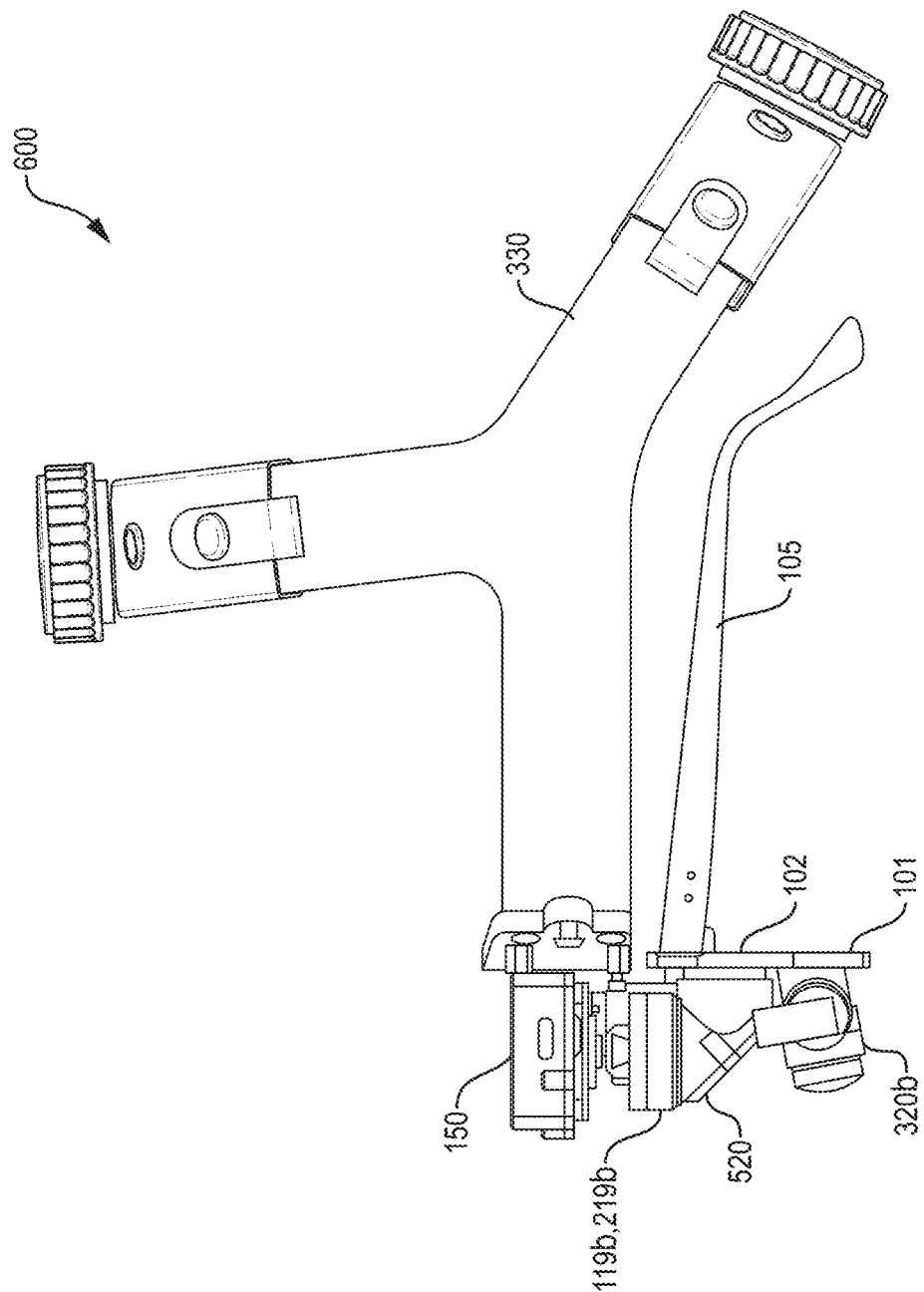

FIGS. 6A and 6B illustrate further aspects of the embodiments of an examination/visualization system shown in FIGS. 5A-5C.

FIG. 6A illustrates an aspect of the invention, wherein the examination/visualization system 600, which is similar to the system shown in FIG. 5A, is incorporated onto, or attached to, head strap 330 rather than onto the eyewear 101. System 600 operates in a manner similar to that of system 500 shown in FIG. 5A and, thus, a detailed discussion regarding the elements and operation of system 600 is believed not necessary for an understanding of its operation by those skilled in the art without further discussion.

FIG. 6B illustrates a side view of the configuration shown in FIG. 6A, wherein electronic assembly 150 is shown attached head strap 330. The attachment of assembly 150 to head strap 330 provides a further means for securing and retaining examination/visualization system 600 while distributing the weight of examination/visualization system 600.

Although FIGS. 6A and 6B illustrate a head band configuration with regard to the embodiment of the examination/visualization system shown in FIGS. 5A-5C, it would be recognized that a head strap (as discussed with regard to FIG. 11) would also be suitable for each of the examination/visualization systems discussed, herein.

Figure 7A:
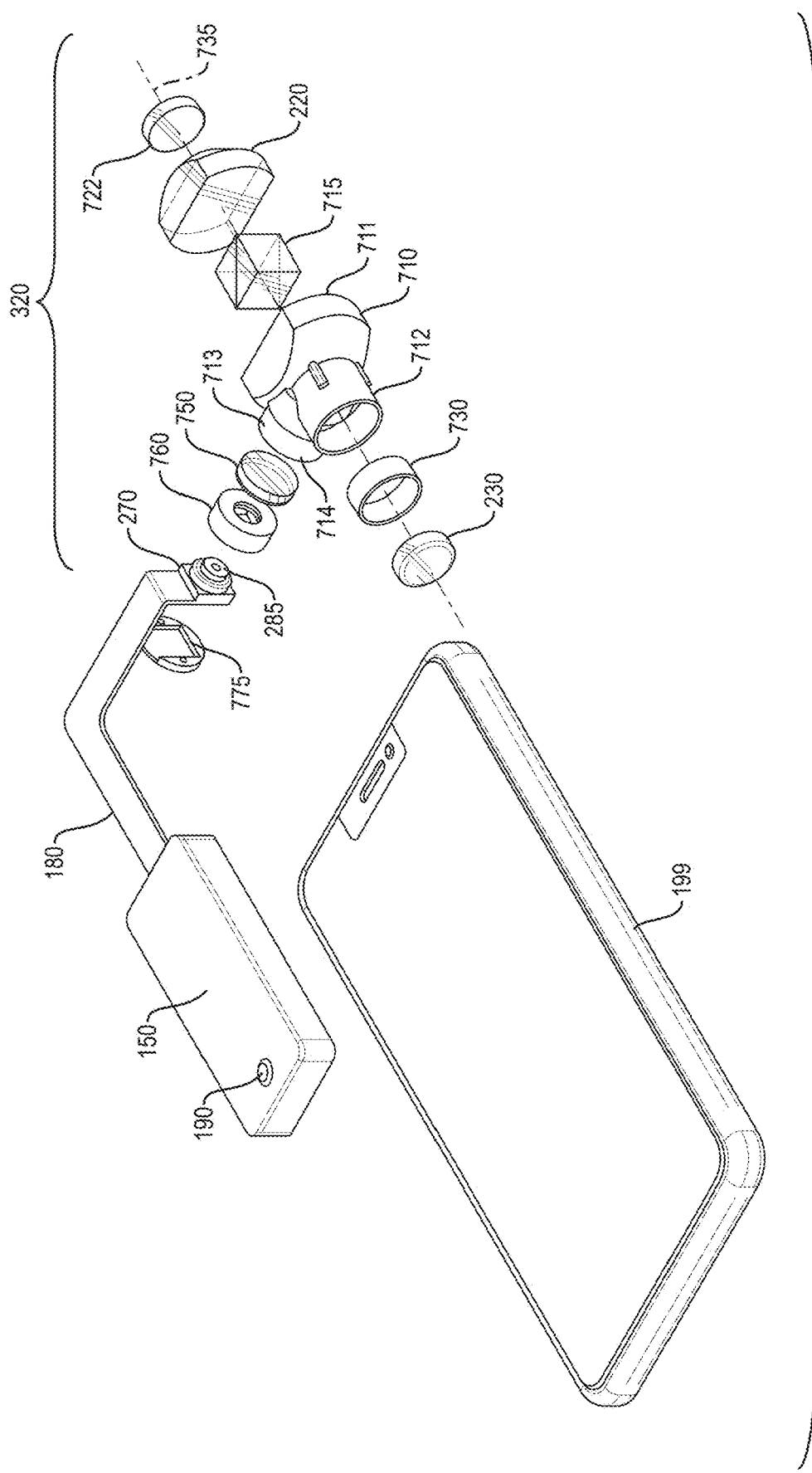
FIG. 7A illustrates an exploded perspective view of a second exemplary embodiment of a viewing/capturing system in accordance with the principles of the invention.

FIG. 7A illustrates an exploded perspective view of a second exemplary embodiment of an examination and visualization system in accordance with the principles of the invention.

In accordance with the principles of the invention, viewing/capturing system 320 represents an integration of magnification device 117 and image capture assembly 113 within a single housing 710. Housing 710 includes a distal (anterior) end 711 into which may be placed objective lens 220 (FIG. 2) and proximal (posterior) end 712 into which may be placed eye-lens housing 730. Further illustrated is eye-lens 230, which may be placed and retained within eye-lens housing 730. Objective lens 220 and eye-lens 230 form a first magnification (or telescopic) device system (i.e., magnification device 117) that allows for the enlarged or magnified view of an object (not shown) when the object is placed along the optical axis 735 (i.e., first optical axis) formed by objective lens 220 and eye-lens 230 at a known distance from objective lens 220.

Working distance lens 722 positioned prior to (or in front of) objective lens 220 establishes a focal point or focal region (i.e., field of view (FoV)) at which objects within the FoV are in focus with respect to a user (not shown). For example, working distance lens 722 may be configured to establish a field of view at a distance between 12-15 inches or at a distance of 13-18 inches or 12-20 inches. Although specific examples are provided, it would be recognized that working distance lens 722 may provide for field of views at other distances without altering the scope of the invention.

Further illustrated is an offset image capture section 713 (i.e., image capture assembly 113) intersecting housing 710 between distal end 711 and proximal end 712, wherein offset image capture section 713 comprises second proximal end 714 and a distal end opening (not shown) into housing 710.

Within second proximal end 714 is positioned sensor housing 760 and second eye-lens 750, wherein second eye-lens 750 forms a second magnification (telescopic) device with respect to objective lens 220 within integrated viewing/capturing system 320 (similar to assembly 113 previously discussed). In one aspect of the invention, second eye-lens 750 may be comparable to eye-lens 230 shown in FIG. 2B.

Within sensor housing 760 is further positioned image capture device 270 and lens 285, wherein lens 285 and image capture device 270 operate to capture images of object (not shown) under one or more lighting conditions (i.e., light of different wavelength bands) being viewed.

In accordance with one aspect of the invention, eye-lens 230 and second eye-lens 750 have a same or a substantially same physical and optical properties (e.g., material, focal lens, curvature, etc.) such that the first magnification device formed by the combination of objective lens 220 and eye-lens 230 has a level of magnification that is a same or a substantially same as a level of magnification of the second magnification device formed by the combination of objective lens 220 and second eye-lens 750.

Second proximal end 714 is further closed or capped by cap 775 such that objective lens 220, second eye-lens 750 and cap 775 seal integrated viewing/capturing system 320 to prevent dust or damage to the elements of integrated viewing/capturing system 320.

Further illustrated is beam splitter or light director 715 positioned within housing 710, which is configured to direct light (i.e., obtained from an object (not shown) being viewed) entering objective lens 220 to both eye-lens 230 and second eye-lens 750, concurrently.

In this illustrated aspect of integrated viewing/capturing system 320, offset image capture section 713 is positioned orthogonal or substantially orthogonal to optical axis 735, wherein the term "substantially orthogonal" refers to a configuration or orientation that is not exactly ninety (90) degrees. Rather the term "substantially orthogonal" would be understood in the art as being 90 degrees within exemplary manufacturing tolerances. For example, plus or minus one-hundredth (1/100) of a degree.

Alternatively, the term "substantially orthogonal" may refer to a range of orientation with respect to the optical axis 735. For example, eight-nine (89) to ninety-one (91) degrees with respect to optical axis 735.

Although offset image capture section 713 is discussed with regard to an offset of substantially orthogonal to the optical axis 735, it would be recognized by those skilled in the art that the angle of offset image capture section 713 may be altered with appropriate accommodation of the orientation of splitter (i.e., light director) 715 to enable light entering objective lens 220 to be directed to both eye-lens 230 and second eye-lens 750 concurrently. Such accommodation would be well-known to those skilled in the art and, thus, is not believed needed for a further understanding of the invention claimed.

In one aspect of the invention, beam splitter (or light director) 715 may split incoming light evenly, (i.e., 50/50 split), for example, between eye-lens 230 and second eye-lens 750 such that the light intensity viewed through eye-lens 230 is a same or substantially a same as the light intensity viewed through second eye-lens 750. Alternatively, beam splitter 715 may split the incoming light differently. For example, 60/40, 70/30, 80/20, 90/10, wherein a greater or larger amount of light is passed through beam splitter 715 toward eye-lens 230 and the remaining (a lesser) amount of light being directed by beam splitter 715 toward second eye-lens 750. In one aspect of the invention, the greater sensitivity of the image capturing capability of module 270 allows for an unequal split of the light entering objective lens 220.

Although FIG. 7A illustrates beam splitter 715 as being a block-shaped element (i.e., block beam splitter) it would be recognized that splitter 715 may comprise a plate beam splitter, a mirror assembly, where the mirror is partially transmissive and partially reflective, etc.

In accordance with one aspect of the invention, wherein offset image capture section 713 is oriented substantially orthogonal to axis 735, the orientation of the reflective element 716 of light director 715 may be oriented at substantially a forty-five (45) degree angle with respect to axis 735.

Although the orientation of the reflective surface 716 of beam splitter 715 is discussed with orientation of plate beam splitter or mirror assembly as being forty-five (45) degrees with regard to axis 735, it would be recognized by those skilled in the art that the orientation of the reflective surface of beam splitter 715 (plate beam splitter, mirror assembly or similar devices that are configured to divide an input light beam into two light beams) may be altered, wherein the alternation is based, in part, by the angle of offset image capture section 713 with respect to axis 735. In the example orientation shown, (i.e., ninety (90) degrees), it would be known in the art that the orientation of forty-five (45) degrees for the reflective surface 716 of director 715 allows for the maximum amount of light to be captured by image capture device 170.

However, it would be recognized that the orientation of offset section 713 may be, in part, determined by the field of view of image capture device 270, such that image capture device 270 is offset and a maximum amount of light is not captured by image capture device 270.

In one aspect of the invention, offset image capture section 713 may be positioned, and sized, with respect to housing 710 to enable the distance between second eye-lens 750 and objective lens 220 to be the same or substantially the same as the distance between objective lens 220 and eye-lens 230. Hence, the magnification of an image of the object being viewed through second eye-lens 750 may be the same or substantially the same as the magnification of the image of the object being viewed through eye-lens 230.

In a second aspect of the invention, the images captured by image capture device 270 may be enlarged by a different degree of magnification as the images viewed by a user (not shown) through eye-lens 230, as will be discussed.

For example, offset image capture section 713 may be sized with respect to housing 710 to create a distance between second eye-lens 750 and objective lens 220 to be different than the distance between eye-lens 230 and objective lens 220. Accordingly, the magnification level of offset image capture section 713 may be significantly increased (e.g., 3× v. 2×).

Figure 7B:
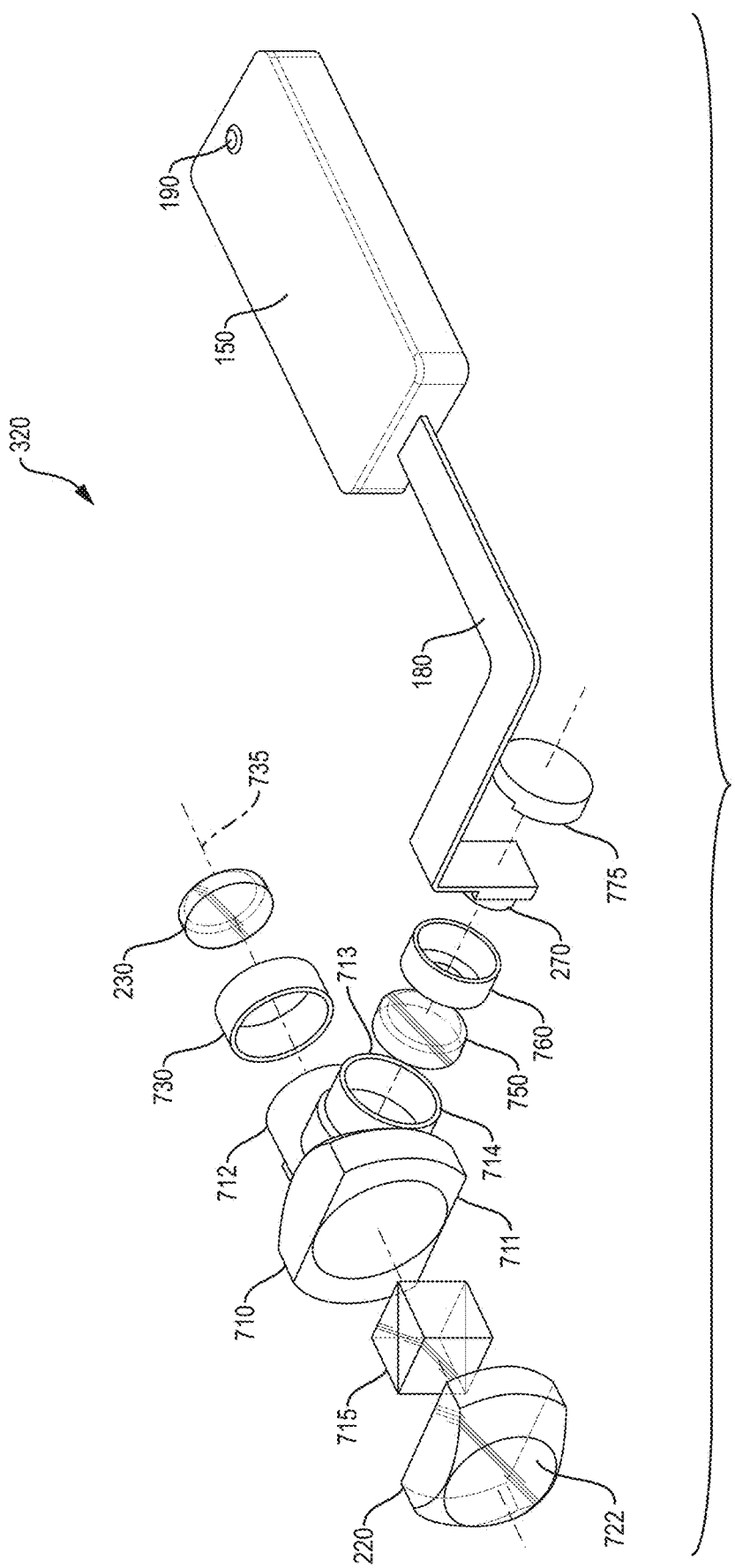
FIG. 7B illustrates a second exploded perspective view of the second exemplary embodiment of the viewing/capturing system shown in FIG. 7A.

FIG. 7B illustrates a second exploded perspective view of the second exemplary embodiment of the viewing/capturing system shown in FIG. 7A.

In this second perspective view, visualization system 320 comprises objective lens 230 positioned at distal end 711 of housing 710, beam splitter 715 within housing 710 and eye-lens 230 positioned within proximal end 712 of housing 710. Further illustrated is offset image capture section 713, positioned between proximal end 711 and distal end 712, into which may be positioned second eye-lens 750 and image capture device 270 (lens 285 (not shown)).

In accordance with the principles of this illustrated aspect of the invention, the positioning of offset image capture section (alternatively referred to as "housing extension") 713 with respect to housing 710 allows for the management of the magnification level of offset image capture section 713. For example, in this illustrated example, offset image capture section 713 is sized to maintain a same or a substantially same equal distance (as light travels) between objective lens 220 and eye-lens 230 and objective lens 220 and second eye-lens 750 to allow for the magnified view of objects viewed and captured.

Further illustrated is the incorporation of working distance lens 722 into objective lens 220 by the appropriate shaping of objective lens 220. The shaping of objective lens 220 to provide for an appropriate working distance lens is known in the art and, thus, a discussion of such shaping is not believed necessary for an understanding of the invention claimed.

Further illustrated are eye-lens housing 730 and sensor housing 760 into which eye-lens 230 and second eye-lens 750, respectively, may be retained. Eye-lens housing 730 and sensor housing 760 may be slidable within corresponding ones of proximal end 712 and second proximal end 714 to render the distance between objective lens 220 and eye-lens 130 the same or substantially the same as the distance between objective lens 220 and second eye-lens 750.

In one aspect of the invention, eye-lens housing 730 and sensor housing 760 may be collimated and glued in place once the appropriate distances are established. In another aspect of the invention, proximal end 712 and second proximal end (or port) 714 may include a screw thread into which corresponding eye-lens housing 730 and sensor housing 760, each with a corresponding screw thread, may be positioned within housing 710.

Although a slidably arrangement or a screw thread configuration is discussed, it would be recognized that other types of connections (e.g., a bayonet connection) for one or both of eye-lens housing 730 and sensor housing 760 may be incorporated into housing 710 without altering the scope of the invention.

Figure 7C:
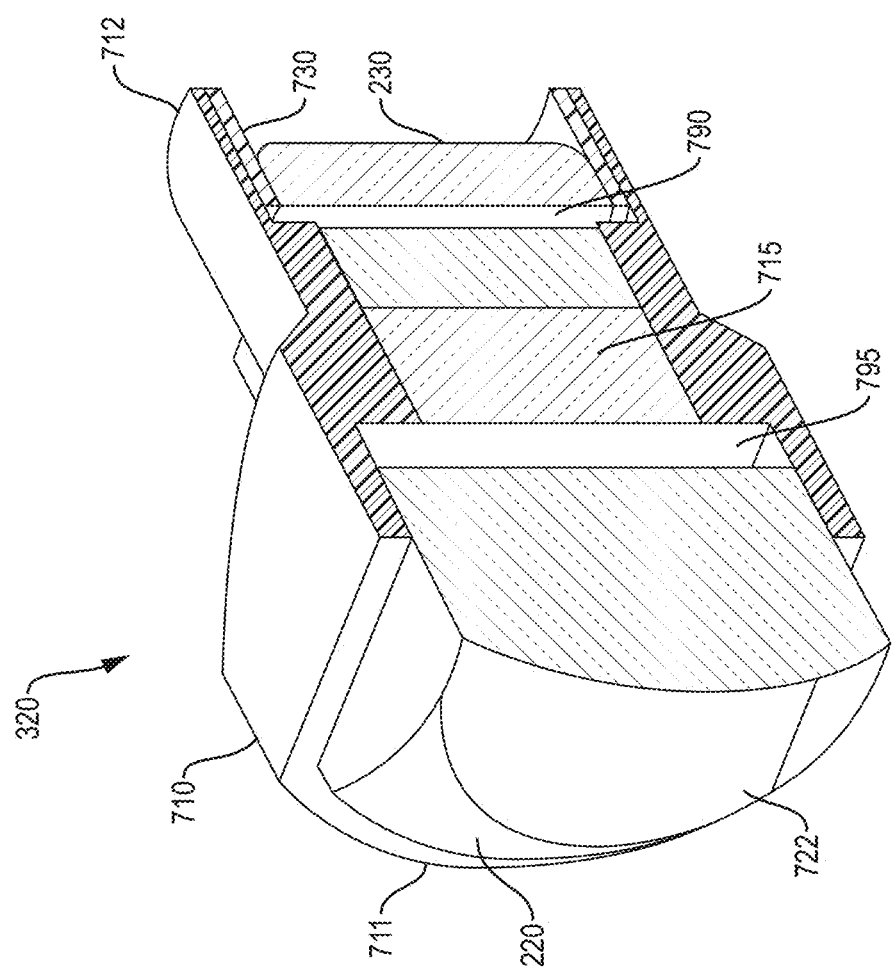
FIG. 7C illustrates a cutaway side view of the assembled viewing/capturing system shown in FIG. 7A.

FIG. 7C illustrates a cutaway perspective view of the assembled viewing/capturing system shown in FIG. 7A.

In this illustrated view, objective lens 220 is positioned within housing 710 and spaced apart from light director 715 by spacer 790. Spacer 790 may comprise an optically clear material of a desired thickness that allows light director 715 to be appropriately positioned within housing 710. Further illustrated is spacer 795, which similar to spacer 790, may comprise an optically clear material of a desired thickness to separate eye-lens 230 an appropriate distance from light director 715 and objective lens 220. Spacers 790 and 795 and light director 715 create a distance between objective lens 220 and eye-lens 230 that determines, in part, the magnification level of integrated viewing/capturing system 320.

Although spacers 795 and 790 are discussed with regard to optically clear material, it would be recognized that spacers 795 and 790 be represented as air gaps that provide for the appropriate distances and spacing of objective lens 220 and eye-lens 230. In one aspect of the invention, the positioning of objective lens 220, light director 715 and eye-lens 230 may be achieved by ridges along an inner surface within housing 710 that limit the movement of the elements contained within the ridges. Thus, spacers 795 and 790 may be represented by ridges within housing 710 that define the fixed placement of the objective lens 220, light director 715 and, in part, housing 730.

In one aspect, the air-gap distance of spacer 790 may be determined by the positioning of eye-lens holder 730 within the proximal end 712 of housing 710. Similarly, an air-gap distance between light director 715 and second eye-lens 750 may be determined by the positioning of second eye-lens holder 750 within proximal end 714.

Figure 7D:
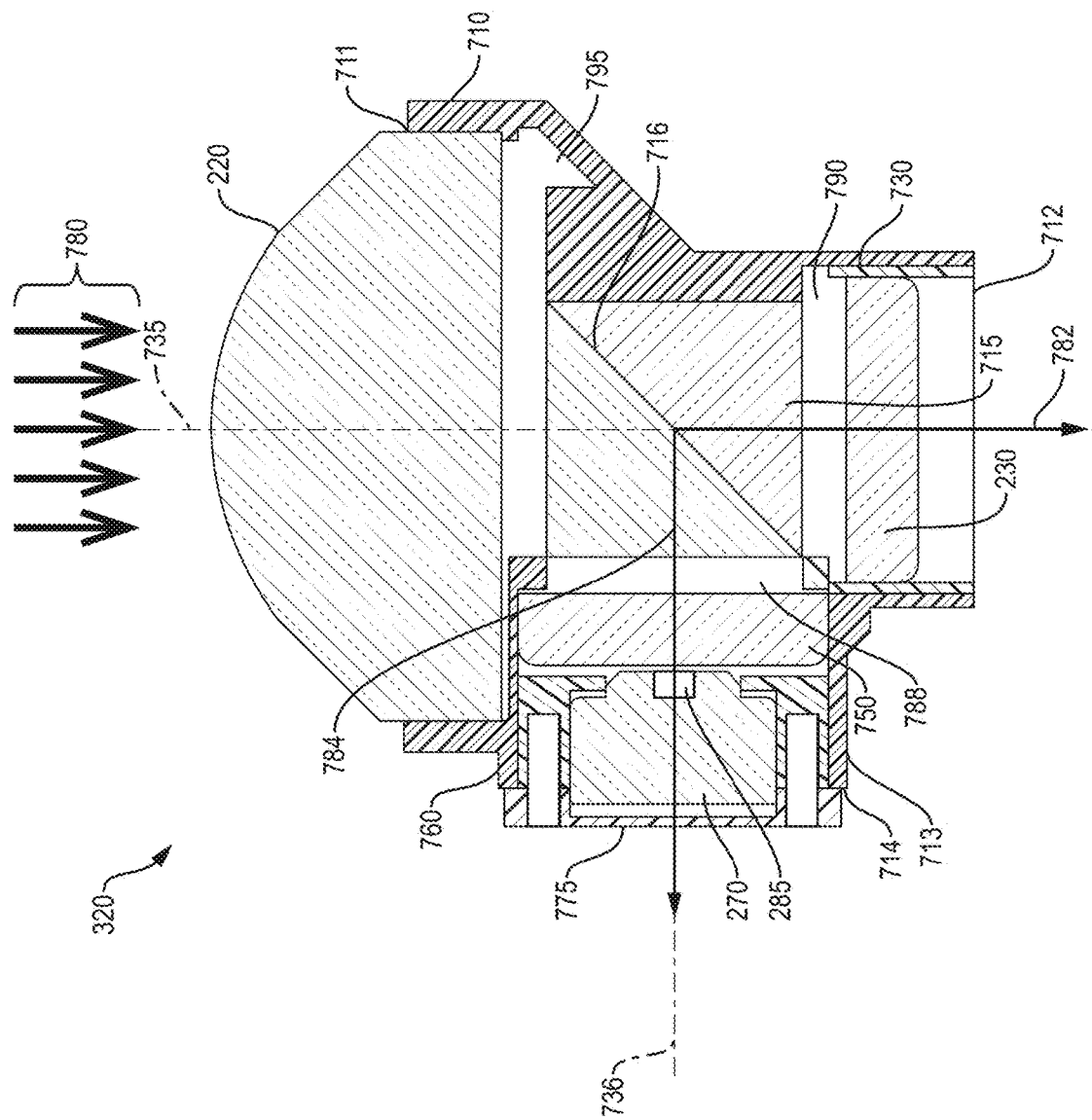
FIG. 7D illustrates a cutaway top view of the viewing/capturing system shown in FIG. 7A.

FIG. 7D illustrates a cutaway top view of the assembled viewing/capturing system shown in FIG. 7A.

In this illustrated view, optical axis 735 is shown extending along a longitudinal axis of integrated viewing/capturing system 320 through objective lens 220 and eye-lens 320, wherein light 780, generally parallel light, associated with an object (not shown) within the FoV from objective lens 220 enters objective lens 220. Further illustrated, is second optical axis 736 (i.e., second optical axis) extending through offset image capture assembly 713, wherein spacer 788 positions second eye-lens 750 a known distance from light director 715 to provide appropriate separation to enable a distance between objective lens 220 and second eye-lens 750 to be, in one aspect of the invention, the same or substantially the same as a distance between objective lens 220 and eye-lens 230. Optical axis 735 and second optical axis 736 intersect along (partially) reflective surface 716 associated with light director (e.g., beam splitter) 715.

In accordance with the principles of the invention, light 780 associated with an image entering objective lens 220 impinges upon partially reflective surface 716 of beam splitter 715, wherein a known portion of light (light 782) of the input parallel light 780 continues through reflective surface 716 toward eye-lens 230 where the outputted light (light 782) may be viewed by a user (not shown). The remaining portion (light 784) of input light 780, which is reflected by reflective surface 716, is directed toward second eye-lens 750, where an image (or a video), which has been magnified by the positioning of objective lens 220 and second eye-lens 750, is captured by image capture device 270.

In one aspect of the invention, the partially reflective surface 716 may allow for an equal distribution (50-50) of light 780 impinging upon its surface being viewed through eye-lens 230 and second eye-lens 750. In another aspect of the invention, the distribution of light 750 may allow for a greater amount (or intensity) of light 750 (i.e., light 782) to pass so as to be viewed and less amount (or intensity) of light 750 (light 784) to be captured by image capture device 270.

For example, reflective surface 716 may possess a transmission/reflective property of a 70/30 light distribution wherein seventy (70%) percent of the light 780, associated with an object impinging upon reflective surface 716, is passed through reflective surface 716 (light 782) to be viewed by a user (not shown), while thirty (30%) percent of the light 780 (i.e., light 784) is reflected by reflective surface 716 toward image capture device 270. Other combinations of light distribution (90/10, 80/20, 60/40, etc.) associated with reflective surface 716 may similarly be incorporated into the transmission/reflective properties associated with light director 715 without altering the scope of the invention.

In this illustrated example, a 75/25 split is shown by the dimensions of the light rays 780, 782 and 784.

As is shown, light 782 presented through eye-lens 230 and light 784 presented second eye-lens 750 is rendered as parallel or substantially parallel light by the nature (physical and optical characteristics, e.g., material, shape, curvature, focal length, etc.) of eye-lens 230 and second eye-lens 750.

Figure 7E:
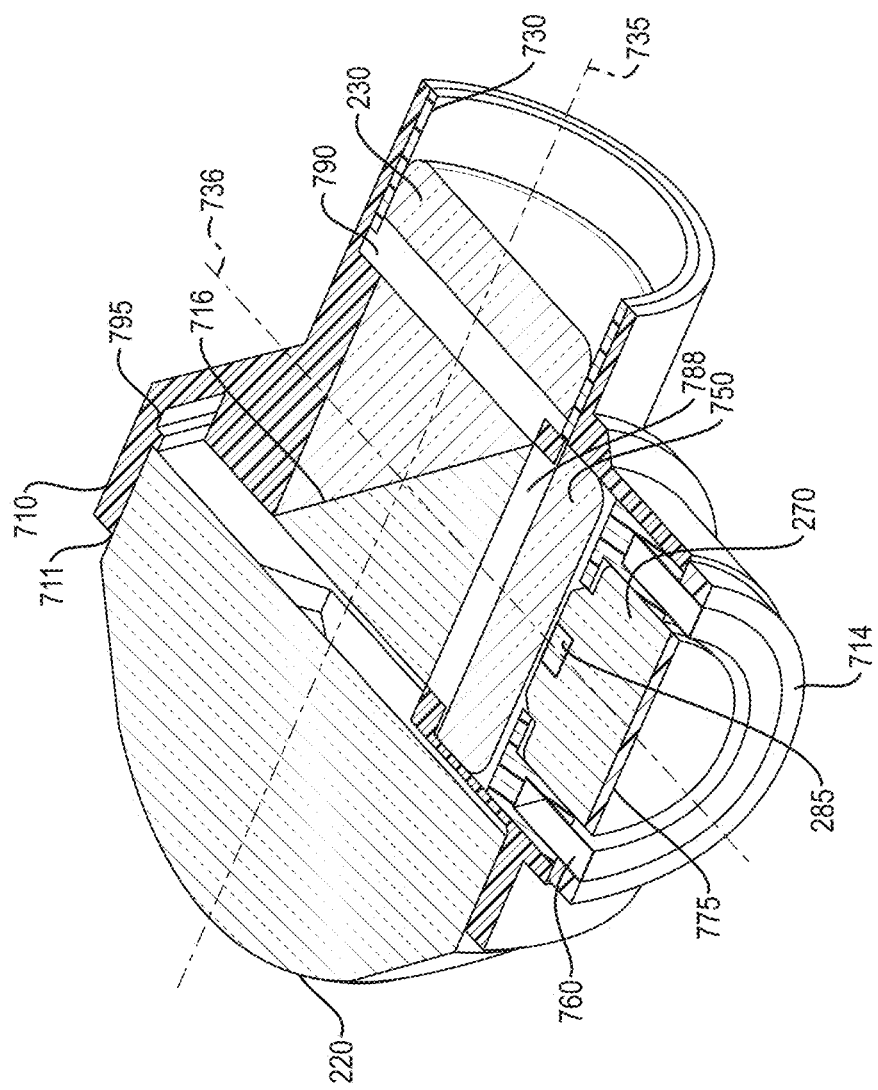
FIG. 7E illustrates a cut-away top view of the assembled viewing/capturing system shown in FIG. 7A.

FIG. 7E illustrates a cut-away perspective top view of the assembled viewing/capturing system shown in FIG. 7A.

In this exemplary perspective top view of integrated viewing/capturing system 320, it is more clearly shown eye-lens 230 and lens housing 730 positioned within proximal end 712 of housing 710 and sensor housing 760 including second eye-lens 750 and image capture device 270 positioned within offset image collection assembly 713.

Figure 8:
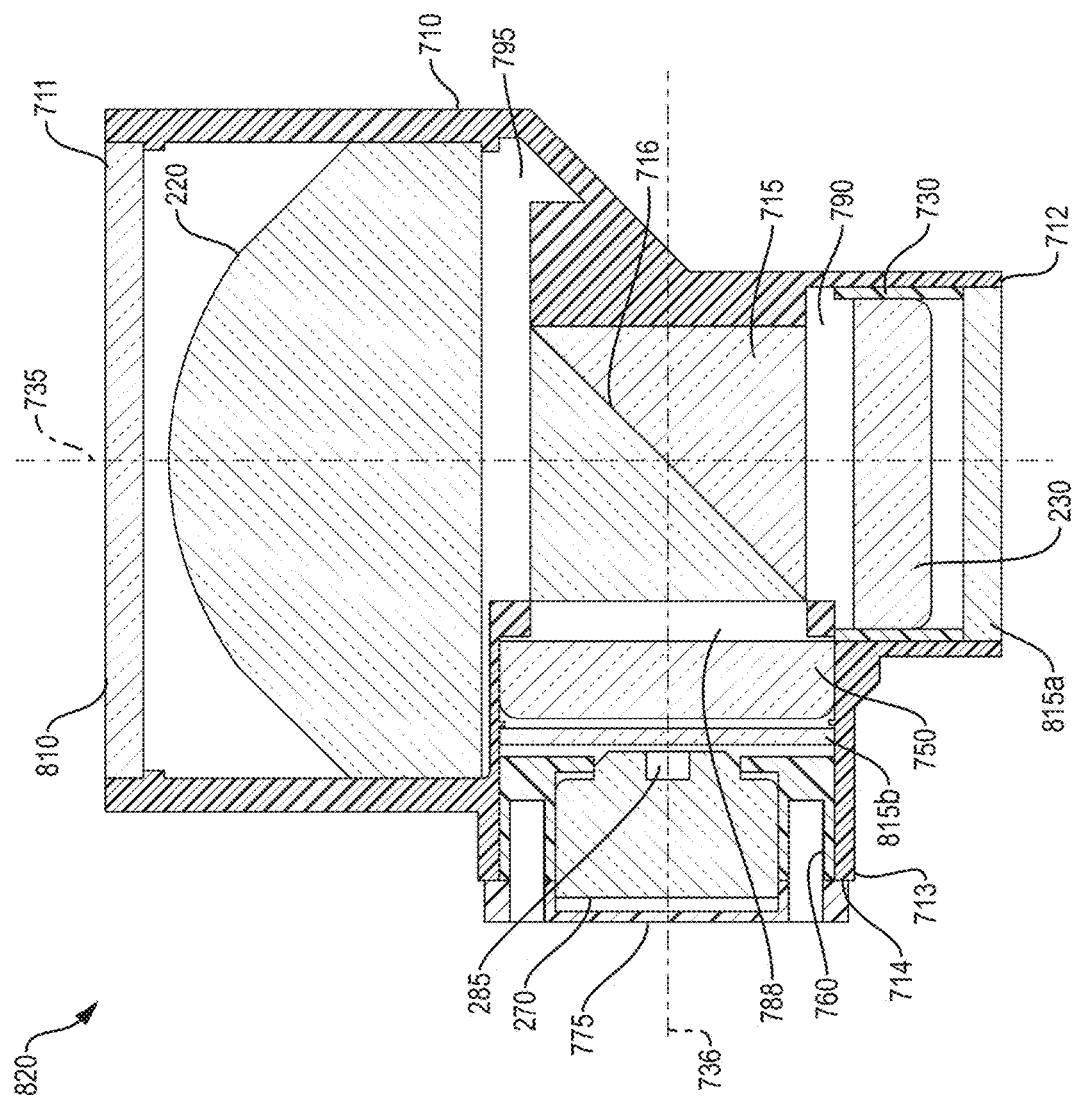
FIG. 8 illustrates a cut-away top view of a second aspect of the second exemplary embodiment of the viewing/capturing system shown in FIG. 7A.

FIG. 8 illustrates a cut-away top view of a second aspect of the second exemplary embodiment of the viewing/capturing system shown in FIG. 7A.

In this illustrated second aspect, which is similar to the configuration shown in FIG. 7A-7E, telescopic/image capture device 820 comprises objective lens 220 contained within distal end 711 of housing 710 and eye-lens 230 positioned within eye-lens housing 730 within proximal end 712. Further illustrated is second eye-lens 750 and image capture device 270 positioned within housing 760, which is positioned in offset image collection assembly 713.

In accordance with this second aspect of a visualization system, further illustrated is objective filter 810 positioned toward distal end 711 of housing 710, wherein filter 810 includes optical characteristics (e.g., absorbance/reflectivity, optical density, wherein optical density is a measure of the transmission of light, at a known wavelength, through the medium of filter 810) to limit, by reduction (attenuation) or reflection, a range of light wavelengths associated with an image being viewed through the objective lens 220, while allowing passage of desired wavelengths. For example, filter 810 may include optical characteristics or properties (absorptive and/or reflective properties) that reduce in magnitude or intensity light (light 780) associated with an image of a viewed object in a first wavelength range while allowing light associated with the viewed object within a second wavelength range to pass unattenuated or substantially unattenuated. In one case wherein the wavelengths within the first wavelength range are less than the wavelengths within the second wavelength range, filter 810 may be referred to as a high-pass filter. Alternatively, when the wavelengths in the first wavelength range are greater than the wavelengths within the second wavelength range, filter 810 may be referred to as a low-pass filter.

In accordance with the principles of the invention, light remaining in the first wavelength range, after being reduced in intensity by filter 810, may then be magnified based on the magnification level obtained by the combination of objective lens 220 and eye-lens 230 (or second eye-lens 750). To reduce the magnified remaining (i.e., residual) light to levels that prevent the viewing of the associated wavelengths, eye-lens filter 815a and second eye-lens filter 815b may be introduced to further reduce the intensity of the residual light.

Eye-lens filter 815a and second eye-lens filter 815b each possess optical characteristics (e.g., absorbance/reflectivity, optical density) to limit, by reduction or attenuation, the intensity of the magnified residual light wavelengths associated with the image being viewed. For example, further filtering of the light in the first wavelength range to a second residual magnitude while allowing light in the second wavelength range to pass unattenuated or substantially unattenuated.

In one aspect of the invention, the optical characteristics or properties (whether absorptive or reflective) of objective filter 810 may be determined based at least on an expected magnitude or intensity of light 780 within a first wavelength range so as to reduce the intensity of the incoming light 780 to a known residual magnitude and the optical characteristics or properties (whether absorptive or reflective) of each of eye-lens filter 815*a* and image capture device filter 815*b* may be based at least on the optical characteristics of objective filter 810, the known level of magnification of the combination of objective lens 220 and eye-lens 230, and the percent of light distribution of light director 715, wherein the intensity of the magnified residual light is reduced to a second residual magnitude.

In one aspect, the second residual magnitude may be selected to be below a level that may cause damage to the eyes of a user viewing the image. Alternatively, the intensity of the light within the first wavelength range may be reduced to prevent the light in the first wavelength range from being viewed or obstructing the viewing of light within the second wavelength range, which may have a significantly lower intensity than the light in the first wavelength range.

In one aspect of the invention, the optical characteristics of eye-lens filter 815*a* and second eye-lens filter 815*b* may be selected to be the same or selected to be different. In one aspect of the invention, the optical characteristics of filters 815*a* and 815*b* may be different based at least in part on the characteristics of light director 715, as the amount of light reaching filter 815*b* may be less than or substantially less than the amount of light reaching filter 815*a*.

Thus, while the optical characteristics of eye-lens filter 815*a* may be selected to reduce the magnitude of an incoming light, as reduced by the characteristics of light director 715, in a first (or undesired) wavelength range to a level that prevents the light in the wavelength range from being harmful to a user or allow light in a desired wavelength range to viewed, the optical characteristics of filter 815*b* may further be determined based on the sensitivity of the image capture device 270. Thus, the optical characteristics of filter 815*b* may be significantly different than those of filter 815*a*.

U.S. Pat. Nos. 10,895,735 and 11,099,376 provide further detailed teaching regarding the selection of the optical characteristics or properties of objective filter 810 and eye-lens filter 815*a* (and/or filter 815*b*) to reduce the intensity of incoming light 780 within a first wavelength band while allowing the incoming light 780 to be unattenuated or substantially unattenuated in a second wavelength band.

Although high-pass and low-pass filters are discussed, it would be known in the art that filters 810, 815*a*, 815*b* may be comprise band-pass type filters, wherein only wavelengths in a desired wavelength band are allowed to pass (e.g., allow only green light to pass) and blocking all other wavelengths. Or may comprise a notch type filter, wherein a band of undesired wavelengths are not allowed to be viewed while allowing all other wavelengths to be viewed (e.g., prevent green light from being viewed). In another aspect of the invention, filter 810 may comprise a high-pass filter that blocks wavelengths below a known value (e.g., 600 nanometer (nm)) and filters 815*a*, 815*b* may comprise a short (or low)-pass filter that blocks wavelengths above a known value (e.g., 500 nm). In this case, wavelengths between 500 nm and 600 nm may not be viewed (i.e., notched out).

Figure 9A:
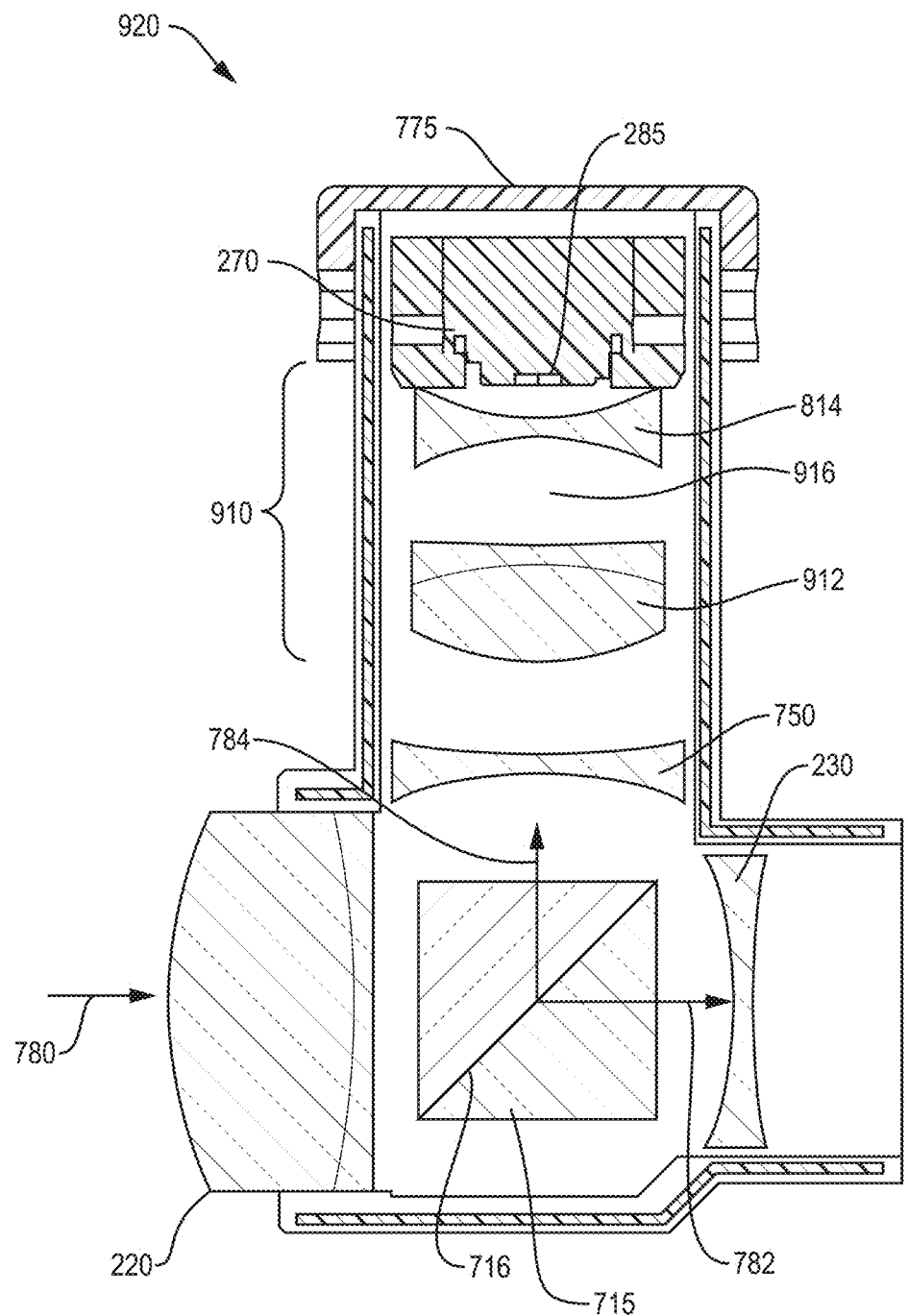
FIG. 9A illustrates a cross-sectional view of a first aspect of a third exemplary embodiment of a viewing/capturing system in accordance with the principles of the invention.

FIG. 9A illustrates a cross-sectional view of a first aspect of a third exemplary embodiment of a viewing/capturing system in accordance with the principles of the invention.

In this illustrated aspect, viewing/capturing system 920 comprises objective lens 220, light director 715, eye-lens 230 and second eye-lens 750, as previously discussed.

Further illustrated is image capture device 270 including lens 285 wherein lens 285 may be integrated into image capture device 270 or separated from image capture device 270, as previously discussed.

In accordance with this aspect of the invention, an "afocal" telescope 910 (i.e., focused at infinity) is inserted between second eye-lens 750 and lens 285 Afocal telescope 910 comprises a second objective lens 912 and a third eye-lens 914 separated by spacer 916.

Afocal telescope 910 represents an additional level of magnification that further magnifies the images (and/or videos) to be captured by image capture device 270. For example, with a 2.5× (2.5 times) magnification level achieved by the optical characteristics of objective lens 220 and second eye-lens 750, afocal telescope 910 provides a further level of magnification of the image to be collected by image capture device 270. For example, with a 2 times (2×) magnification associated with afocal telescope 910, the images (and/or video) captured or collected by image capture device 270 are magnified by five times (5×).

Figure 9B:
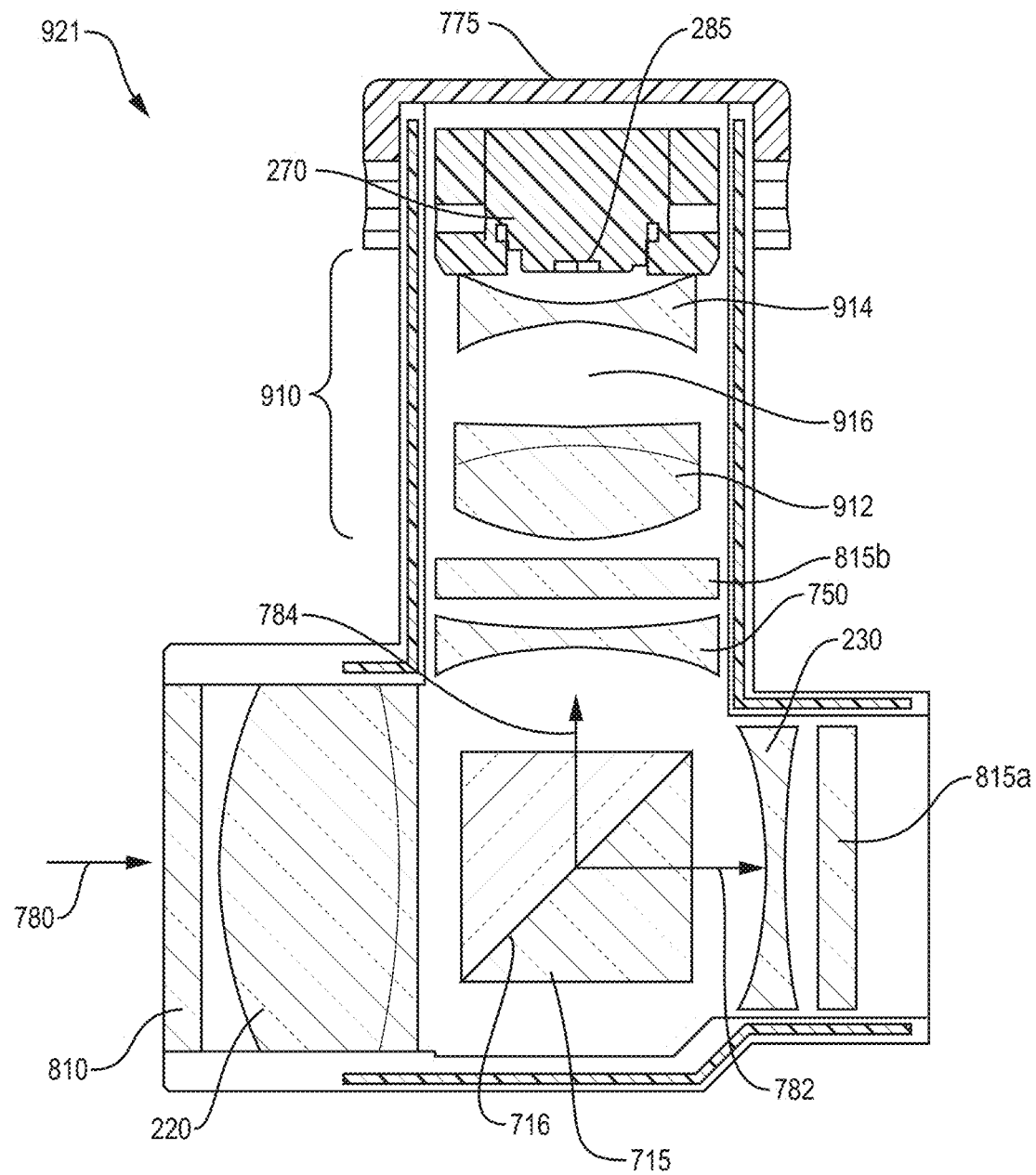
FIG. 9B illustrates a cross-sectional view of a second aspect of the third exemplary embodiment of the viewing/capturing system shown in FIG. 9A.

FIG. 9B illustrates a cross-sectional view of a second aspect of the third exemplary embodiment of the viewing/capturing system shown in FIG. 9A.

In this illustrated aspect of the invention viewing/capturing system 921, similar to device 920 shown in FIG. 9A, comprises a first magnification device comprising objective lens 220 and eye-lens 230 and a second magnification device comprising a second magnification device comprising objective lens 220 and second eye-lens 750. Further illustrated are 810, 815*a* and 815*b*, which were previously discussed with regard to FIG. 8, to filter out wavelengths of incoming light 780 from being viewed by a practitioner or collected by image capture device 270.

Operation of the viewing/capturing system 921 is comparable to device 920 (FIG. 9) with the addition filtering elements of device 820 (FIG. 8) to limit the wavelength range viewed by a practitioner in a manner similar to that discussed with regard to FIG. 8.

Although FIGS. 1-9B illustrate a Galilean telescopic configuration in the discussion of the integrated magnification/collecting device disclosed, herein, it would be recognized by those skilled in the art that a Keplerian telescopic configuration (i.e., objective lens, eye-lens and orienting prism) would be applicable to the combined magnification/recording devices discussed, without altering the scope of the invention claimed. Keplerian telescopes are known to those skilled the art and, thus, a detailed discussion of the incorporation of a Keplerian telescopic configuration into the illustrated embodiments of the invention is not believed needed for the understanding and practicing of the invention.

In addition, although FIGS. 7A-8C illustrate a magnification/collecting devices wherein a magnification level associated with each of the first magnification device and the second magnification device is equal or substantially equal by the positioning of the first eye-lens 230 and the second eye-lens 750 with respect to the objective lens 220, and FIGS. 9A and 9B illustrate devices for increasing the magnification level of the second magnification device through the introduction of an "afocal" telescopic lens, it would be recognized by those skilled in the art, that the magnification level of the second magnification device may be different than that of the magnification level of the first magnification device by the use of a different positioning of second eye-lens 750 with respect to objective lens 220, or the use of a second eye-lens 750 with optical characteristics that are different than those of the first eye-lens 230 or the use of a lens 285 of a different magnification level associated with image capture device 270, for example. Such methods for increasing the magnification level of offset image capture section 713 have been contemplated and are considered within the scope of the invention claimed.

Figure 10:
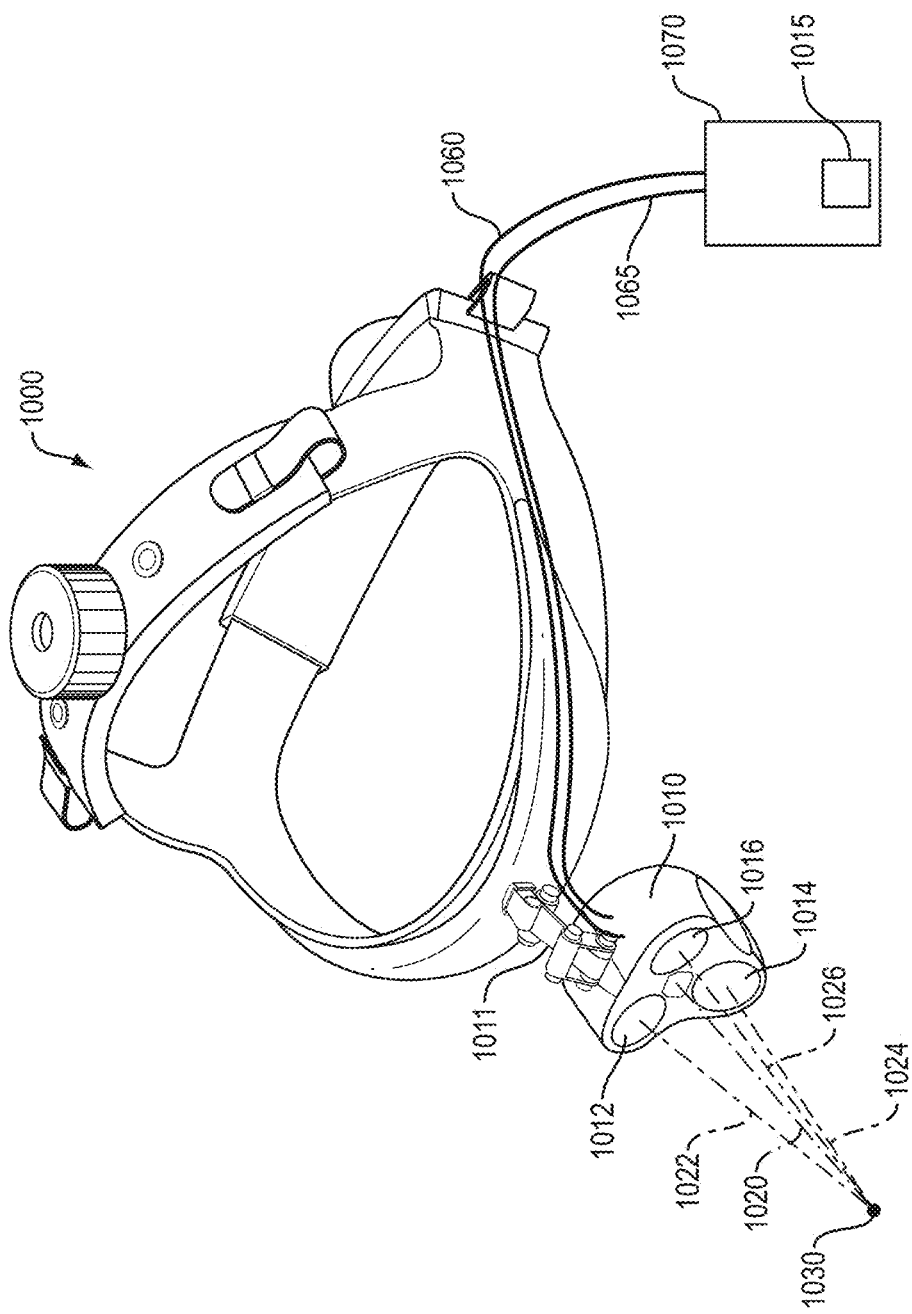
FIG. 10 illustrates a perspective view of a first exemplary embodiment of a lighting system in accordance with the principles of the invention.

FIG. 10 illustrates a perspective view of a first exemplary embodiment of a head-mounted lighting system in accordance with the principles of the invention.

In this first exemplary embodiment, lighting system 1000 comprises head band or head strap 1005 (which is similar to headband 330 previously discussed) and light assembly 1010, shown suspended from a head band or head strap 1005, wherein light assembly 1010 includes a plurality of lighting elements 1012, 1014, 1016, concentrically positioned about central (or center) axis 1020 extending orthogonal or substantially orthogonal to a plane of light assembly 1010.

Lighting elements 1012, 1014, 1016 are further illustrated as being oriented at an angle with respect to central axis 1020, wherein the angle of orientation of each of lighting elements 1012, 1014, 1016 is such that the light emitted along a respective optical axis, represented as dashed lines 1022, 1024 and 1026, of corresponding ones of lighting elements 1012, 1014, 1016, respectively, converge on a same or common point 1030 (i.e., viewing point) along central axis 1020. Viewing point 1030, which is in the area or the FoV, a known distance from light assembly 1010.

Lighting elements 1012, 1014, 1016 may be configured to output light independently of each other or in combination with one or more of the other lighting elements 1012, 1014, 1016. Accordingly, the light emitted from lighting elements 1012, 1014, 1016, may, thus, be mixed together at the point of convergence 1030 along central axis 1020. Or may be individually emitted such that light from one lighting element is presented at point of convergence 1030.

The light emitted by lighting elements 1012, 1014, 1016 may, for example, be one of a white light, an ultra-violet light, an infra-red light or a visible light in one or more visible light bands (referred to as colored light). For example, one or more lighting elements 1012, 1014, 1016 may emit light in an ultra-violet wavelength range of about 10 to about 400 nanometer (nm). Or may emit light in one or more of a visible color light range. For example, in one or more specific color wavelength ranges (e.g., violet—380-435 nm; blue—435-495 nm; cyan—495-520; green—720-570 nm; yellow—570-590 nm; orange—590-620 nm and red—620-750 nm) or combinations thereof, and an infra-red light (greater than 700 nm) Or may emit light as a white light (i.e., 380-750 nm).

For example, lighting element 1012 may emit a white light and each of lighting elements 1014 and 1016 emit a light at a same wavelength. In another aspect of the invention, lighting element 1012 may emit a white light and each of lighting elements 1014 and 1016 may emit light in a same wavelength band. In still another aspect of the invention, the intensity of the light emitted by lighting elements 1012, 1014, 1016 may be varied when light is concurrently emitted from the lighting elements.

Although specific wavelength ranges are discussed above, it would be recognized that the wavelength ranges are merely representative of light wavelength ranges as different sources may quote different specific values for the disclosed color wavelength ranges.

Further details regarding the lighting assembly configuration shown in FIG. 10 may be found in U.S. Pat. Nos. 10,247,384 and 11,099,376 and the patents and patent applications depend therefrom.

Light assembly 1010 may be retained to head band 1005 by bracket 1011 that allows for the adjustment of light assembly 1010 to direct light generated by the lighting elements 1012, 1014, 1016 toward viewing point 1030. As will be discussed, a practitioner, by the adjustment of light assembly 1010, may orient viewing point 1030 to be co-incident or substantially co-incident to a FoV established by the magnification devices previously discussed.

Further illustrated is power controller 1070. Power control 1070 may include a power source (i.e., a battery, an AC/DC converter) that provides power to the lighting elements 1012, 1014, 1016 through one or more electrically conductive elements 1060, 1065. For example, power and/or control signals to control which of lighting elements 1012, 1014, 1016 is to receive the provided power and not to receive provided power may be provided to lighting assembly 1010 through conductive elements 1060, 1065. Alternatively, electronic elements associated with the control of providing power to one or more of lighting elements 1012, 1014, 1016 may be incorporated into housing 1010.

Further illustrated is switch 1015 that may operate to determine which of the multiple lighting sources within lighting elements 1012, 1014, 1016 emit light in at least one wavelength band.

Switch 1015 may represent at least one of: a physical switch, a contact switch and a contactless switch. For example, switch 1015 may represent a contact-type switch control, which utilizes a physical switch or a capacitive touch (e.g., a touch of a contact point that alters a capacitance or an alternation in an electro-static field) to alter the output of light from corresponding ones of lighting elements 1012, 1014, 1016. For example, switch 1015 may comprise a multi-functional switch that allows for different combinations of light to be emitted by lighting assembly 1010 wherein a change state of one or more of lighting elements 1012, 1014, 1016 in assembly 1010 may occur by the contact of a finger, a hand, an elbow or foot pressed against, or coming in proximity to, switch 1015. In one aspect of the invention, switch 1015 may represent a bellows switch attached to a belt that may be operated by depression of the bellows by an elbow). For example, switch 1015 may enable lighting assembly 1010 to emit different combinations of light (e.g., white only, white/colored, colored only, IR, etc.) with sequential actions on switch 1015.

Alternatively, switch 1015 may represent contactless switch control for the application of a voltage (or current) to be applied to lighting sources 1012a, 1014a, 1016a. For example, a non-contact control of the voltage (or current) applied to lighting sources 1012a, 1014a, 1016a may be achieved by the occurrence of a detection of a reflection of a signal, such as an infra-red, or an ultra-sonic, signal, that may be transmitted through a transmitter (not shown) and which is reflected by an object passing through the transmitted signal. A reflection of the transmitted signal may be detected by a receiver (or a detector, not shown). The receiver or detector may then generate an indication of the reflected signal power controller 1070 to apply a voltage to, or remove a voltage from, lighting sources 1012a, 1014a, 1016a.

In still another example, a capacitive non-contact switch may be used to apply a voltage or current to lighting sources 1012a, 1014a, 1016a. In example, an electrostatic field may be established around switch 1015 and an alteration of the electrostatic field (by an object passing through the electrostatic field) may then generate an indication of the alteration of the field to apply or remove the voltage to or from lighting sources 1012a, 1014a, 1016a.

Contactless switch 1015 may be local to the power controller 1070 or remote from power controller 1070, as previously discussed in a manner similar to the discussion of a contact switch control.

Although switch 1015, is shown within power controller 1070, it would be recognized that switch 1015, 1115 may be a separate unit, remote from power controller 1070, that may be placed within housing 1010, on a belt (e.g., a bellow switch activated by an elbow) or on a floor (e.g., a foot switch), wherein the remote switch may be in wired or wireless communication with a controller (e.g., power controller 1070) that is responsive to the engagement (i.e., contact or proximity) of switch 1015 to provide electrical energy from power controller 1070 to lighting assembly 1010.

In one aspect of the invention, the selection of which of integrated viewing/capturing systems 320a, 320b (110a, 110b) is activated to capture images of an object positioned within the field of view (FoV) may be determined based on the light emitted by one of lighting elements 1012, 1014, and 1016.

For example, integrated viewing/capturing system 320a may be activated with the emission of a white light from source 1012, and integrated viewing/capturing system 320b may be activated with the emission of a colored light (e.g., a non-white visible light) from at least one of light source 1014, 1016. Alternatively, integrated viewing/capturing systems 320a, 320b may both be activated with the emission of an infra-red light from one of lighting elements 1014, 1016. In one aspect of the invention, the intensity of the white light when emitted solely may be different when the white light is emitted concurrently with one or more colored light or non-visible light (e.g., infra-red, ultraviolet).

Figure 11:
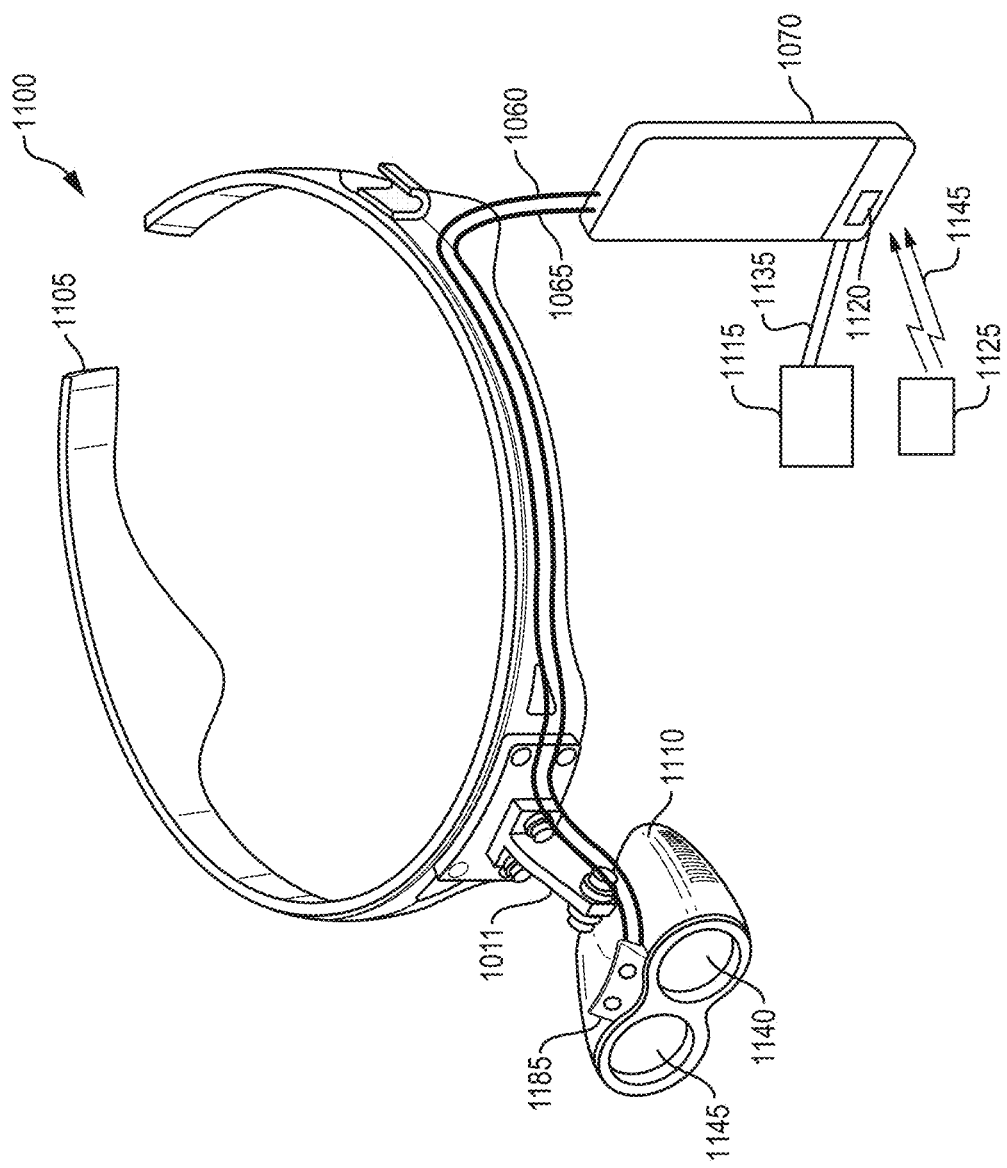
FIG. 11 illustrates a perspective view of a second exemplary embodiment of a lighting system in accordance with the principles of the invention.

FIG. 11 illustrates a perspective view of a second exemplary embodiment of a head-mounted lighting system in accordance with the principles of the invention.

In this illustrated exemplary second embodiment, lighting system 1100 comprises head band 1105 and lighting assembly 1110, which, in this illustrate embodiment, comprises lighting elements 1140, 1145, shown suspended from head band 1105 by bracket 1011.

Bracket 1011 allows for the positioning of lighting assembly 1110 to direct light onto a desired common point (i.e., a FoV) as previously discussed.

Each of the two lighting elements 1140, 1145 may be capable of generating light in at least one of a plurality of wavelength ranges similar to those discussed with regard to FIG. 10. Further illustrated is power controller 1070 (e.g., a battery pack), remotely located from light assembly 1110. Power controller 1070 provides electrical energy to the lighting sources (not shown) within lighting elements 1140, 1145, in a manner as previously disclosed.

Further illustrated are switches 1115 and 1125, which are illustrated as being remote from power controller 1070, wherein switches 1115 and 1125 operate similar to switch 1015, previously discussed, to determine which of the multiple lighting sources within lighting elements 1140, 1145 emit light in at least one wavelength bands. Switch 1115 may represent a single function (or a multi-functional) switch that is wired communication with power controller 1070, as represented by wired connections 1135 to alter the state of the emitted light in a manner similar to that discussed with regard to switch 1015. In one aspect of the invention, switch 1115 may, for example, be attached to a collar, a shirt, a belt, etc., that may be operated by the touch of switch 1115. Alternatively, switch 1115 may be operated by the detection of the proximity of an object (e.g., a hand) to switch 1115. In another aspect of the invention, switch 1115 may be a foot switch, which is placed on the floor near a practitioner's foot to change the state of light emitted.

Switch 1125 may represent a single functional (or a multi-functional) switch that is in wireless communication with power controller 1070, to alter the state of the emitted light in a manner similar to that discussed with regard to switches 1015 and 1115. Switches 1115 and 1125 may be in communication with power controller 1070 through interface 1120. Interface 1120 may represent a conventional wired interface (RS 232, USB-A, USB-c, etc.), for example. Alternatively, interface 1120 may represent a conventional wireless communication interface (BLUETOOTH, Wi-Fi using one or more of IEEE 811 protocols, etc.).

Although FIGS. 10 and 11 illustrate multiple lighting elements, it would be recognized that lighting assemblies 1010 and 1110 may comprise a single lighting element without altering the scope of the invention claimed. In this case, the single lighting element may comprise a plurality of lighting sources that emit light in a plurality of wavelength bands.

FIGS. 12A-12E illustrated exemplary embodiments of lighting sources that may be contained within the illustrated lighting elements of assemblies 1010 and 1110. A more detailed discussion of exemplary embodiments of lighting sources may be found in U.S. Pat. Nos. 11,231,165, 11,099, 376 and 10,247,384.

FIG. 12A illustrates an exploded perspective view of a first exemplary embodiment of a lighting element incorporated into light assemblies 1010, 1110 shown in FIGS. 10 and 11, respectively.

In this exemplary embodiment lighting element 1012 (or 1014, 1016) comprises a housing 1210 including, therein, a lighting source 1012a, centered or substantially centered on a printed circuit board 1211 retained on base 1215 within housing 1210. As would be known in the art lighting source 1012a may comprise a single light or an array of lights (light emitting diodes) arranged to emit light. For example, lighting source 1012a may represent a light emitting diode, which may be of a laser or non-lasing variety.

Although discussion is made with regard to lighting element 1012, it would be understood that the discussion of lighting element 1012 would be applicable to a discussion of lighting elements 1014, 1016. Thus, a more detailed discussion of the elements of lighting elements 1014, 1016 is not believed needed for those skilled in the art to practice the invention claimed.

Printed circuit board (PCB) 1212 includes electrical/electronic circuitry, similar to that previously discussed, that controls the operation of lighting source 1210a (e.g., turn on/off).

In one aspect of the invention, lighting element 1012 may include aperture holder (or plate) 1220 and aperture 1230, including centered or substantially centered aperture holder passthrough 1225 and aperture passthrough 1235, respectively, through which light from lighting source 1210a may pass. Aperture holder passthrough 1225 and aperture passthrough 1235 are sized to provide for a reduction of stray light emanating from lighting source 1012a.

Although aperture holder passthrough 1225 and aperture passthrough 1235 are shown as comprising a circular form, it would be understood that aperture holder passthrough 1225 and aperture passthrough 1235 may be in a square or rectangular form, or a combination thereof, without altering the scope of the invention. In one aspect or the invention, the circular, the square or the rectangular form of passthroughs 1225, 1235 may be sized such that the die portion of a semiconductor light emitting diode forming light source (e.g., 1012a) may be inserted into at least one of aperture holder passthrough 1225 and aperture passthrough 1235.

Further illustrated is a dome lens 1240, centered or substantially centered over the passthroughs 1225, 1235, wherein the lighting source 1012a is positioned within or at a focal point of dome lens 1240. Dome lens 1240 provides for the focusing of the light generated by lighting source 1012a.

Lighting element 1012 may further include lens housing 1250, which is attachable to housing 1210 and used to retain the lighting source 1012a within the housing 1210.

In this illustrated embodiment, housing 1210 further includes an internal screw thread 1217, that mates to a corresponding screw thread 1251 on lens housing 1250 to enable housing 1210 and lens housing 1250 to be rendered as a single unit).

Although a screw thread is illustrated, it would be recognized that housing 1210 and lens housing 1250 may be joined by other means. For example, a bayonet connection, a snap-fit connection, a form fit connection and other similar connections.

Further shown, on lens housing 1250, are grooves 1254 circumventing lens housing 1250. Grooves 1254, which is an optional feature of lens housing 1250, provide for an increased surface area to distribute heat generated within lighting element 1012.

Lighting element 1012 is closed by lens 1245. In accordance with the principles of the invention, the lighting source 1012a is positioned within a focal length of the objective lens 1245 when lens housing 1250 is joined to housing 1210. The positioning of light source 1012a within the focal lengths of dome lens 1240 and lens 1245 provides for a more even distribution of light. See for example, U.S. Pat. Nos. 7,690,806 and 10,247,384 for further details regarding obtaining a uniform or a substantially uniform light distribution.

Figure 12B:
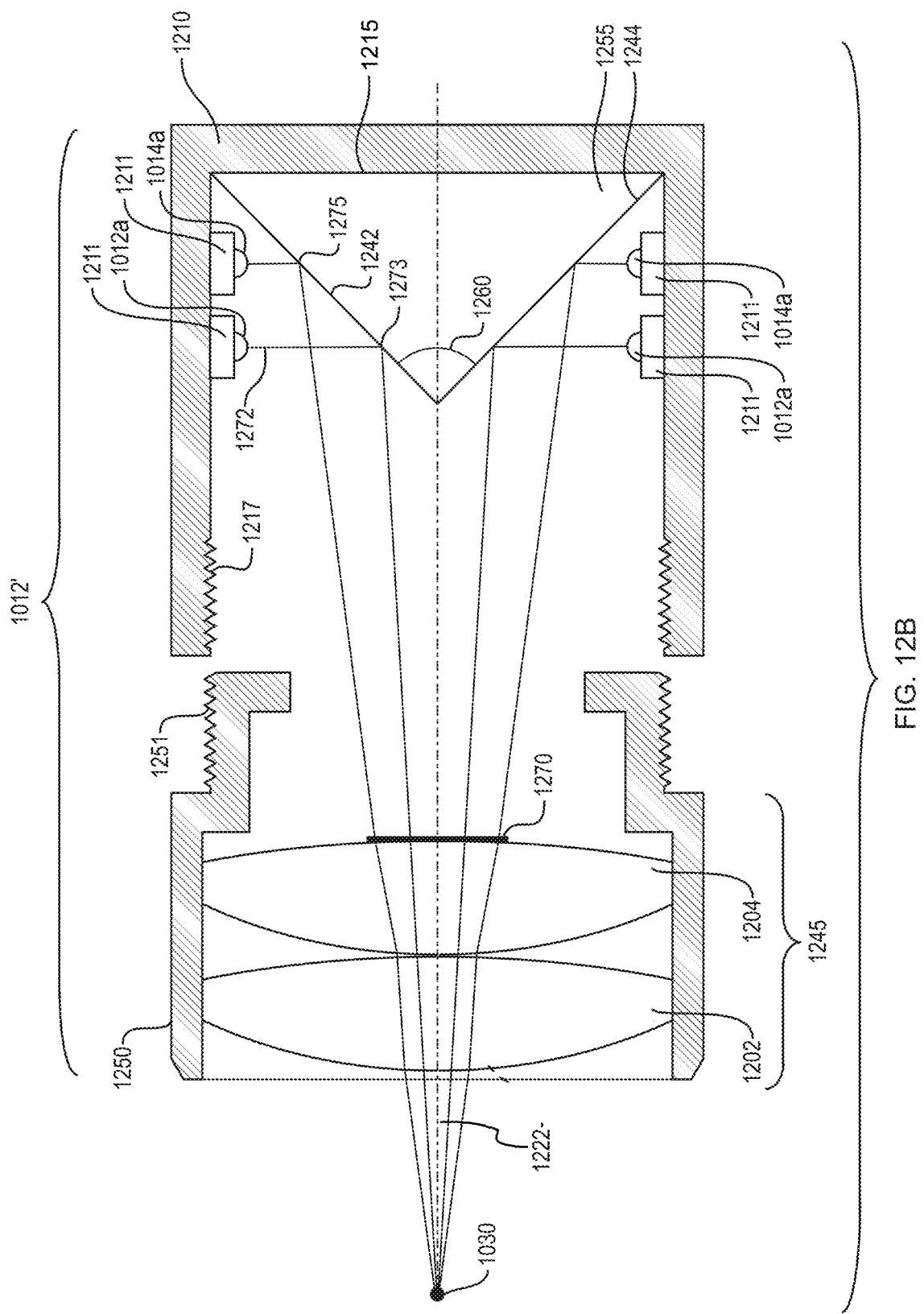
FIG. 12B illustrates a side view of the first aspect of the second exemplary embodiment of a lighting element incorporated into lighting assemblies shown in FIGS. 10 and 11.

FIG. 12B illustrates a side view of a first aspect of a second exemplary embodiment of a lighting element incorporated into light assemblies shown in FIGS. 10 and 11.

In this first aspect of exemplary lighting element, which correspond to any one of lighting elements 1012, 1014, 1016, and which is referred to as lighting element 1012', lighting element 1012' comprises lens housing 1250 containing, objective lens 1245 (which in this illustrated example comprises objective lens 1202 and 1204) and housing 1210 comprising at least one of a plurality of lighting sources 1012a, 1014a (1016a not being shown). Objective lens 1245 defines an optical axis 1222 through lighting element 1012'.

Lighting sources 1012a, 1014a, (1016a) may be similar to those previously discussed including aperture 1220, aperture holder 1220 and dome lens 1240 (see FIG. 12A). Alternatively, the lighting sources 1012a, 1014a (1016a) may be construction such that the lighting source(s) lacks one or more of aperture 1220, aperture holder 1230, and dome lens 1240, without altering the scope of in the invention claimed.

In accordance with this exemplary first aspect of lighting element 1012a, the illustrated lighting sources 1012a, 1014a (1016a) are oriented about an inner circumference of housing 1210 wherein light emitted by lighting sources 1012a, 1014a (1016a) is directed to light (or lighting) director 1255.

Light director 1255, extending from base 1215 of housing 1210, comprises a plurality of reflective surfaces (e.g., highly polished mirror, etc.) 1242, 1244 joined together at a peak angle 1260, which receive light emitted by corresponding ones of light sources 1012a, 1014a (1016a) and redirects the received light towards an area 1270 about optical axis 1222.

In accordance with the aspect of the illustrated exemplary embodiment, lighting sources 1012a and 1014a (1016a) are positioned at different locations along the inner circumference of housing 1210, such that light emitted by lighting source 1012a, projected along light path 1272, contacts light director 1255 at a first point 1273 and light emitted by lighting source 1014a (1016a), projected along light path 1274, contacts light director 1255 at a second point 1275.

The light from lighting sources 1012a, 1014a (1016a) is then directed toward area 1270 on objective lens 1245, such that the emitted light from the light sources converges or substantially converges about common point 1030.

More specifically, the apex angle 1260 of light director 1255 may be selected to direct the emitted light onto region 1270 of lens 1245 such that light emitted by lighting sources 1012a, 1014a, 1016a, after passing through lens 1245, is focused, or is converged, onto common point 1030 along axis 1222 a known distance from lens 1245. As would be understood by those skilled in the art, axis 1222 is comparable to axis 1022 shown in FIG. 12A as being the axis along which light emitted by a lighting element (i.e., illustrated lighting element 1012a) is directed.

In the illustrated aspect of the invention apex angle 1260 is shown to be greater than ninety (90) degrees as the orientation of light sources 1012a, 1014a (1016a) is substantially orthogonal to axis 1222. Hence, the apex angle 1260 may be, in part, determined based on the orientation of lighting sources 1012a, 1014a (1016a), with respect to axis 1222, the characteristics of lens 1245, and the distance to common point 1030.

Further illustrated is PCB 1211 as previously disclosed with regard to FIG. 12A, comprises electrical and electronic components that may be used to control the application of an electrical energy (voltage, current) to one or more of lighting sources 1012a, 1014a (1016a) Although a plurality of PCBs 1211 are shown, it would be understood by those skilled in the art that a single PCB 1211 may be utilized to control the application of electrical energy to the illustrated lighting sources.

Light sources 1012a may comprise white light emitting elements, and selected ones of lighting sources 1014a (1016a) may emit in at least one wavelength range, wherein the first wavelength range and second wavelength range may be the same or different. For example, both lighting sources 1014a and 1016a may emit light at a same wavelength. Alternatively, at least one lighting source 1014a (1016a) may emit light in a first wavelength range (e.g., an ultraviolet wavelength range) while selected other ones of lighting sources 1014a (1016a) may comprise sources emitting light in a second wavelength range, (e.g., blue wavelength range, IR range, etc.).

Figure 12C:
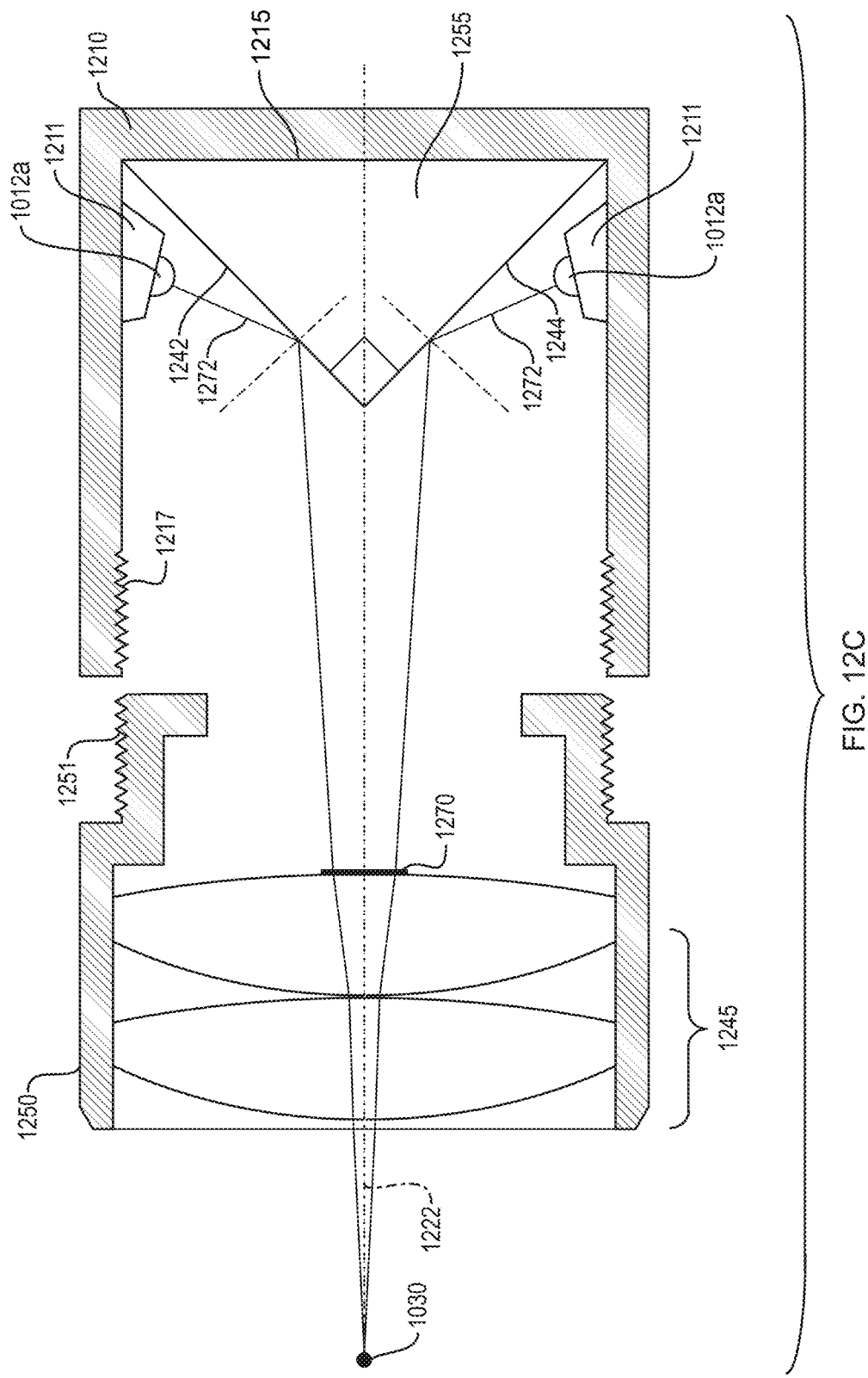
FIG. 12C illustrates a side view of a second aspect of the second exemplary embodiment of a lighting element incorporated into lighting assemblies shown in FIGS. 10 and 11.

FIG. 12C illustrates a side view of a second aspect of a second exemplary embodiment of a lighting element incorporated into light assemblies shown in FIGS. 10 and 11.

In this illustrated second aspect, light director 1255 comprises a plurality of reflective surfaces (i.e., highly polished, mirror, etc.) 1242, 1244 joined together at a peak angle 1260 extending from a base 1215 of housing 1210, wherein the apex angle 1260 of light director 1255 is ninety or substantially ninety (90) degrees.

In accordance with this illustrated second aspect, lighting sources 1012*a*, for example, is oriented offset from a vertical or substantially vertical axis with respect to axis 1222, such that light emitted by lighting source 1012 and reflected by reflecting surface 1242, 1244 is directed toward region 1270 on objective lens 1245. The light directed toward region 1270, subsequently, after passing through lens 1245, converges onto an area about common point 1030, in a manner similar to that discussed with regard to FIG. 12B. In this aspect of the invention, the orientation of lighting sources 1012*a* (1014*a*, 1016*a*) with respect to axis 1222 is based, in part, on the characteristics of lens 1245 and a distance to common point 1030.

Figure 12D:
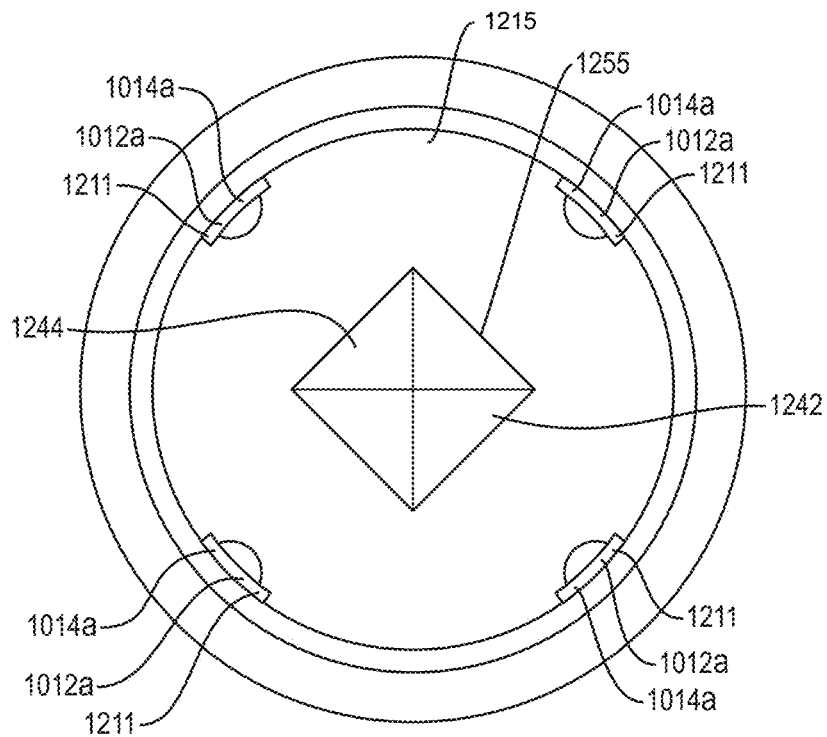
FIG. 12D illustrates a front view of a first aspect of the second exemplary embodiment of the lighting element shown in FIG. 12B.

FIG. 12D illustrates a front view of the first aspect of the second exemplary embodiment of the lighting element shown in FIG. 12B.

In this illustrated first aspect of the lighting source configuration a plurality of lighting sources 1012*a* are arranged about an inner circumference surface of lighting housing 1210 in a first plane and lighting sources 1014*a* (1016*a*), which are not visible in this illustrated first aspect as these modules are positioned behind lighting modules 1012*a*, in a second plane with respect to optical axis 1222, wherein lighting sources 1014*a* (1016*a*) are positioned behind (and thus not visible in this illustrated view) lighting sources 1012*a*. Lighting sources 1014*a* (1016*a*) are positioned behind lighting sources 1012*a*, as the light emitted from lighting sources 1014*a* (1016*a*) must contact reflective surfaces 1242, 1244 at an appropriate angle. Axis 1222 in this illustrated front view extends into the plane of the paper on which this front view is drawn.

Figure 12E:
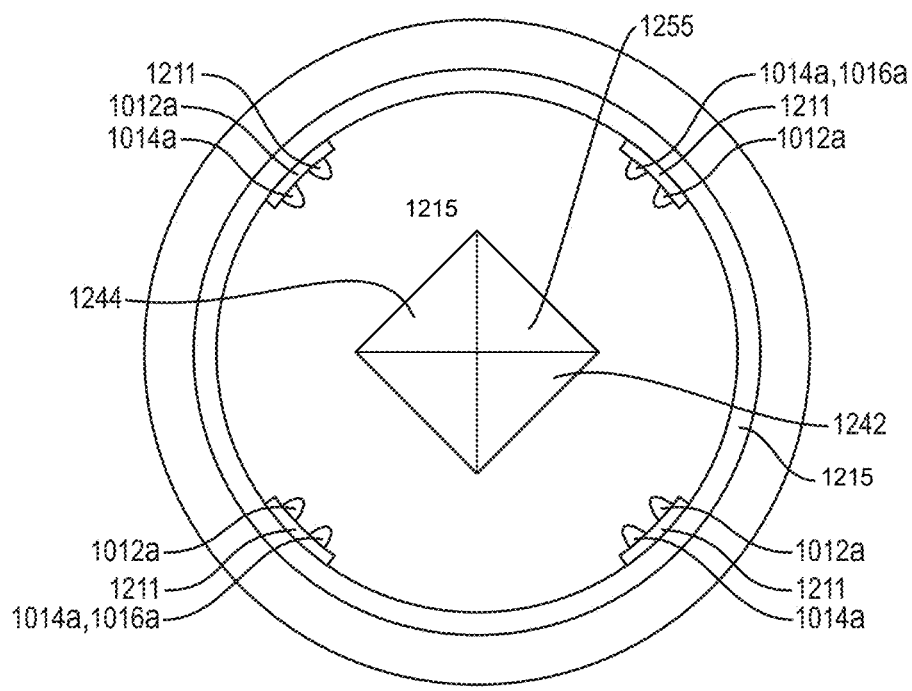
FIG. 12E illustrates a front view of a second aspect of the second exemplary embodiment of the lighting element shown in FIG. 12B.

FIG. 12E illustrates a front view of a second aspect of the second embodiment of the lighting element shown in FIG. 12B.

In this exemplary second aspect, a plurality of lighting source, 1012*a*, 1014*a*, 1016*a* are arranged as pairs along a same plane (with respect to axis 1222) about an inner circumference surface of housing 1210, wherein the lighting source pair 1012*a*, 1014*a*, 1016*a* are controlled individually, concurrently or sequentially by controller formed on PCB 1211.

In this exemplary aspect, light emitted by lighting sources 1012*a*, 1014*a*, 1016*a* is directed toward light director 1255, which redirects the light toward lens 1245 (not shown), along axis 1222, as previously discussed.

Although only four lighting sources are shown in FIGS. 12C and 12D, it would be recognized that the number of lighting sources included along the inner surface of housing 1210 may be increased or decreased based on the number of reflective surfaces 1242, 1244 of light director 1255.

Figure 13:
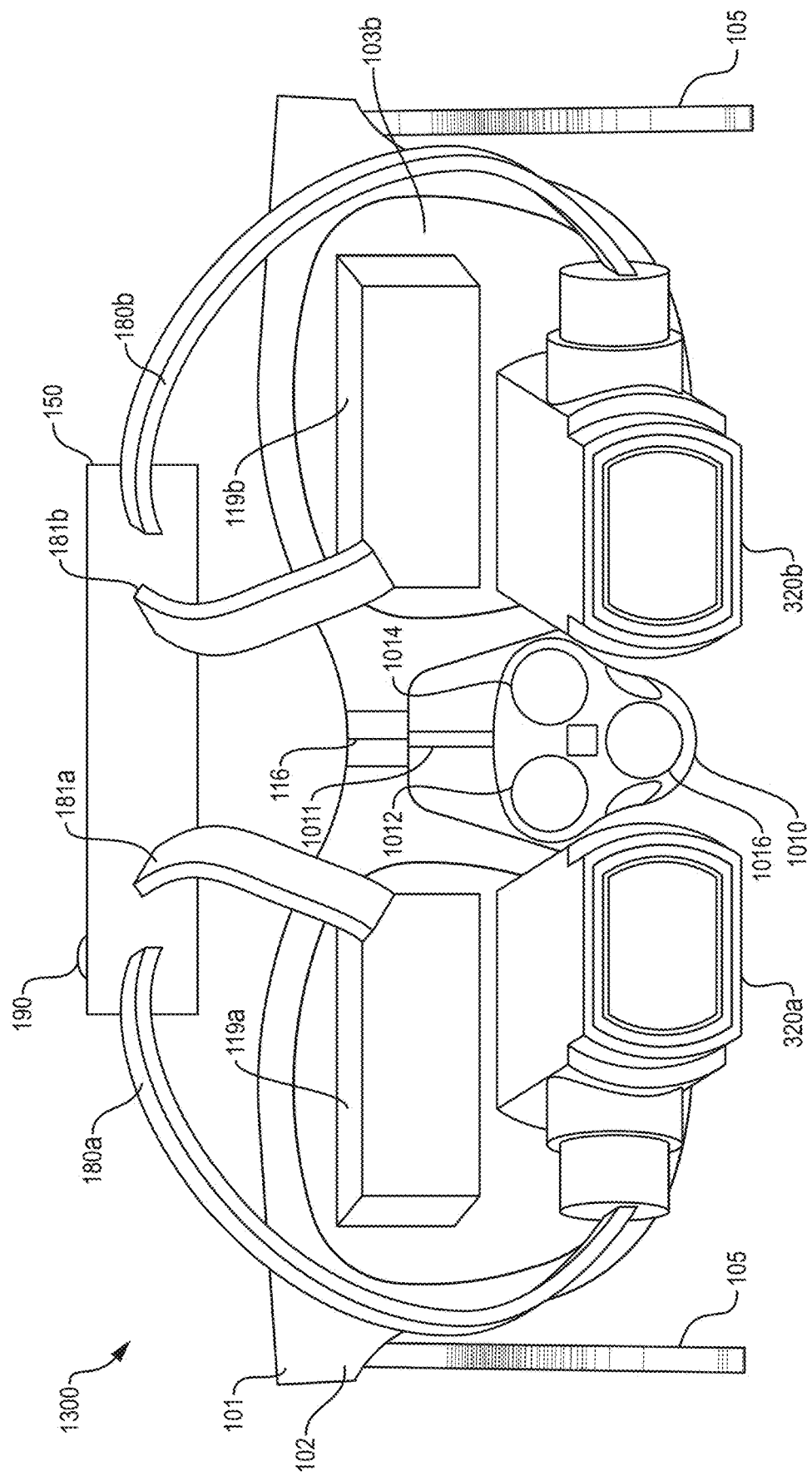
FIG. 13 illustrates a frontal view of a first exemplary embodiment of a head-worn examination/visualization/collection system with light enhancement in accordance with the principles of the invention.

FIG. 13 illustrates a frontal view of a first exemplary embodiment of a head-worn examination/visualization/collection system with light enhancement in accordance with the principles of the invention.

In this first exemplary embodiment of examination/visualization/collection system 1300 comprises eyewear 101, comprising integrated viewing/capturing system 320*a*, 320*b* and display systems 119*a*, 119*b* associated with lenses 103*a*, 103*b*, respectively, as presented in FIGS. 1-6B. Integrated viewing/capturing system 320*a*, 320*b* provide for the visualization, collection of images associated with objects (not shown) and display system provides for the display of the viewed objects within a field of view defined by the integrated viewing/capturing system 320*a*, 320*b*. Further illustrated is electronic assembly 150 and transmitter(/receiver) 190 that allow for the transfer of the collected images associated with the, not shown, viewed objects to one or more external devices (e.g., see FIG. 1) for subsequent processing.

Further illustrated is light assembly 1010 attached to eyewear 101, wherein light assembly 1010, comprising lighting elements 1012, 1014 and 1016, provides light on the, not shown, objects within the FoV associated with the integrated viewing/capturing system 320.

As previously discussed, lighting assembly 1010 may provide light in one or more wavelength bands (e.g., white light/IR light, white light/blue light, etc.) and integrated viewing/capturing system 320*a*, 320*b*, may include one or more optical filters (see FIG. 8) that limit light the wavelength range viewable through integrated viewing/capturing systems 320*a*, 320*b*. For example, with the emission of a white light and one or more blue lights, filters 810, 815*a*, 815*b* may limit (i.e., block) the light viewable by viewing/capturing systems 320*a*, 320*b* to light in a wavelength range to prevent at least one of the emitted blue lights to be viewable while allowing other light to pass unattenuated or substantially unattenuated (e.g., a long pass filter). Alternatively, filters 810, 815*a*, 181*b* may be selected to remove or block light in an undesired wavelength range (e.g., the emitted light) while allowing light in all other wavelength ranges to pass unattenuated or substantially unattenuated.

Figure 14:
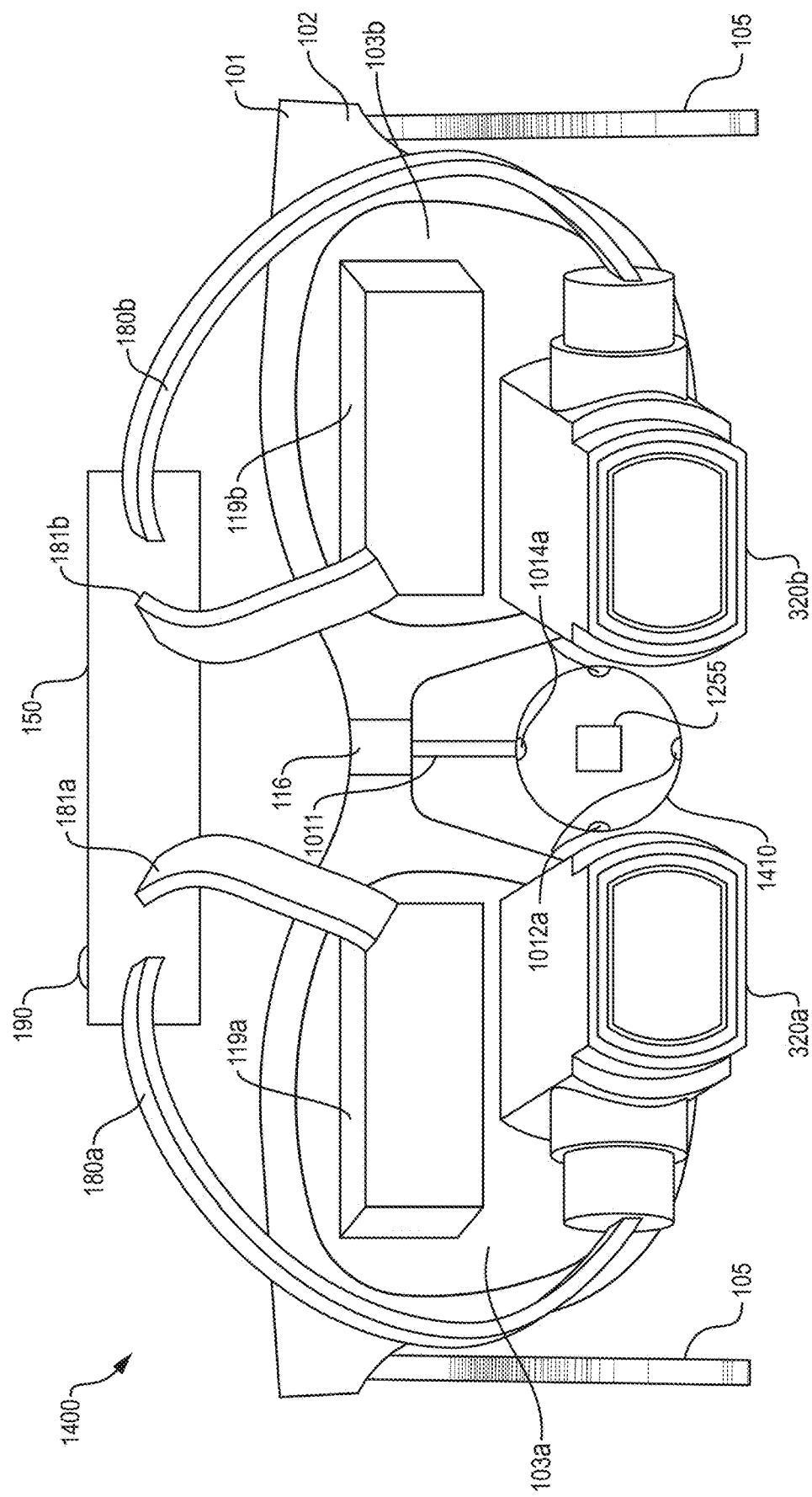
FIG. 14 illustrates a frontal view of a second exemplary embodiment of a head-worn examination/visualization/collection system with light enhancement in accordance with the principles of the invention.

FIG. 14 illustrates a frontal view of a second exemplary embodiment of a head-worn examination/visualization/collection system with light enhancement in accordance with the principles of the invention.

In this second exemplary embodiment of an examination/visualization system 1400, which is similar to examination/visualization system 1300, comprises eyewear 101, comprising integrated viewing/capturing system 320*a*, 320*b* and display systems 119*a*, 119*b* associated with lenses 103*a*, 103*b*, respectively, similar to system 1300 (FIG. 13).

Further illustrated lighting assembly 1410, which comprises a single lighting assembly 1410, which provides for the emission of a plurality of light wavelengths. In this second exemplary embodiment, lighting assembly 1410 comprises lighting sources 1012*a*, 1014*a*, etc., positioned about an inner circumference of lighting element 1140, similar to the configuration shown in FIGS. 12B, 12C, wherein light associated with one or more of lighting sources 1012*a*, 1014*a*, etc., may be emitted to illuminate objects within a FoV associated with integrated viewing/capturing systems 320*a*, 320*b*.

In one aspect of the invention, light emitted by lighting assembly 1410 may comprise white light only. In another aspect of the invention, light emitted by lighting assembly 1410 may emit a combination of white light and colored light, wherein the intensity of the colored light is greater than the intensity of the white light by one of: the use of more colored light lighting sources or by the application of a lower current to those lighting sources that emit white light than those lighting sources that emit colored light. In another aspect of the invention, light emitted by lighting assembly 1410 may emit white light and colored light, wherein the colored light may be emitted at two different wavelengths, wherein the intensity of the white light and one of the colored lights may be less than the intensity of the other colored light. In another aspect of the invention, lighting assembly 1410 may emit white light and an infra-red light concurrently.

In one aspect of the invention, integrated viewing/capturing systems 320*a*, 320*b* may include filtering capabilities (i.e., filters 810, 815*a*, 815*b* (see FIG. 8) that allow for the viewing of selected light wavelengths wherein the filtering capabilities of the filters may be selected based on the intended characteristics of the light to be emitted by lighting assembly 1410 (and 1010, 1110). For example, a long-pass filter to block wavelengths in a first wavelength range and allow wavelengths in a second wavelength range to pass, where the first wavelength range and the second wavelength range include light at wavelengths emitted by lightings sources 1014*a*, 1016*a*. Or a notch filter to where light emitted by lighting sources 1014*a*, 1016*a* are blocked from being viewed while other light wavelength ranges are allowed to pass.

Although not shown, it would be recognized that power control module 1070, shown in FIGS. 10 and 11, may provide electrical energy to integrated viewing/capturing system 320*a*, 320*b* and lighting assembly 1010, 1110 and 1410 shown in FIGS. 10, 11, 13 and 14.

In addition, although power controller 1070 is discussed as including a power source that is remote from systems 1300, 1400, it would be recognized that one or both of power controller 1070 and a (not shown) power source may be local to systems 1300, 1400 by being attached to eyewear 101, for example.

Although integrated viewing/capturing systems 320*a*, 320*b* are illustrated in FIGS. 13 and 14, it would be recognized that the visualization system 110*a*, 110*b* shown in FIG. 1 may be incorporated within the exemplary examination/visualization systems with light enhancement shown in FIGS. 13 and 14, without undue experimentation.

Figure 15A:
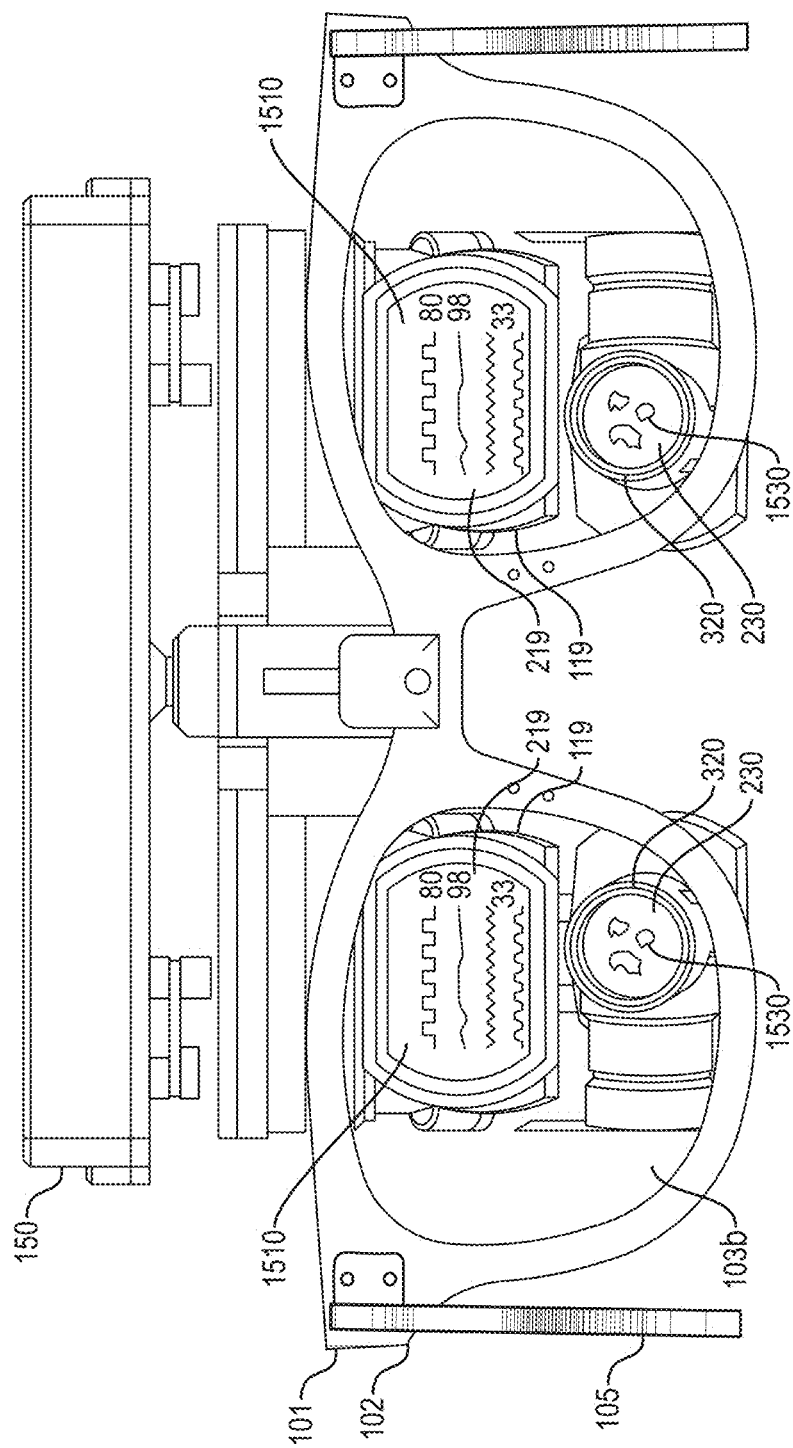
FIGS. 15A-15C illustrate exemplary displays associated with the examination and visualization systems with light enhancement disclosed herein.

FIG. 15A illustrates an exemplary presentation of real-time data that may be provided to a practitioner in accordance with the principles of the invention.

In this illustrated embodiment, lenses 103*a*, 103*b* of eyewear 101 are shown, wherein display screens 219*a*, 219*b* and eye-lenses 230*a*, 230*b* are viewable through lens 103*a*, 103*b*. As previously discussed, display screens 219*a*, 219*b* may be positioned before and after (i.e., through) lenses 103*a*, 103*b*, where the term "before" refers to the position of display screen 219*a*, 291*b* as being viewable through corresponding lenses 103*a*, 103*b* and the term "after" refers to display screen 219*a*, 219*b* being closer to an eye than corresponding lens 103*a*, 103*b*. Magnification/viewing system 320 is positioned through lenses 103*a*, 103*b* (see FIG. 4B).

Further illustrated is real-time data (e.g., heart rate, breath rate, etc.) 1510 presented on display screens 219*a*, 291*b*, by the receiving of such data by a receiving system 190, for example, associated with electronic assembly 150.

Real-time data 1510 displayed may represent heart rate, blood pressure, etc., information that is collected and processed by external monitor devices, which may then provide such data, as previously discussed by wired or wired communication to electronic assembly 150 for subsequent presentation on display screens 219*a*, 219*b*. In addition, the displayed data 1510 may concurrently be provided to an external display (e.g., remote display 170) that allows for the viewing by other personnel local or remote from the practitioner viewing data 1510.

The presentation of real-time data to the practitioner on display screen 219 is advantageous as it provides needed information to the practitioner focused on images 1530 of object through eye-lens 230 without the practitioner altering their position to view the external display containing such data.

Figure 15B:
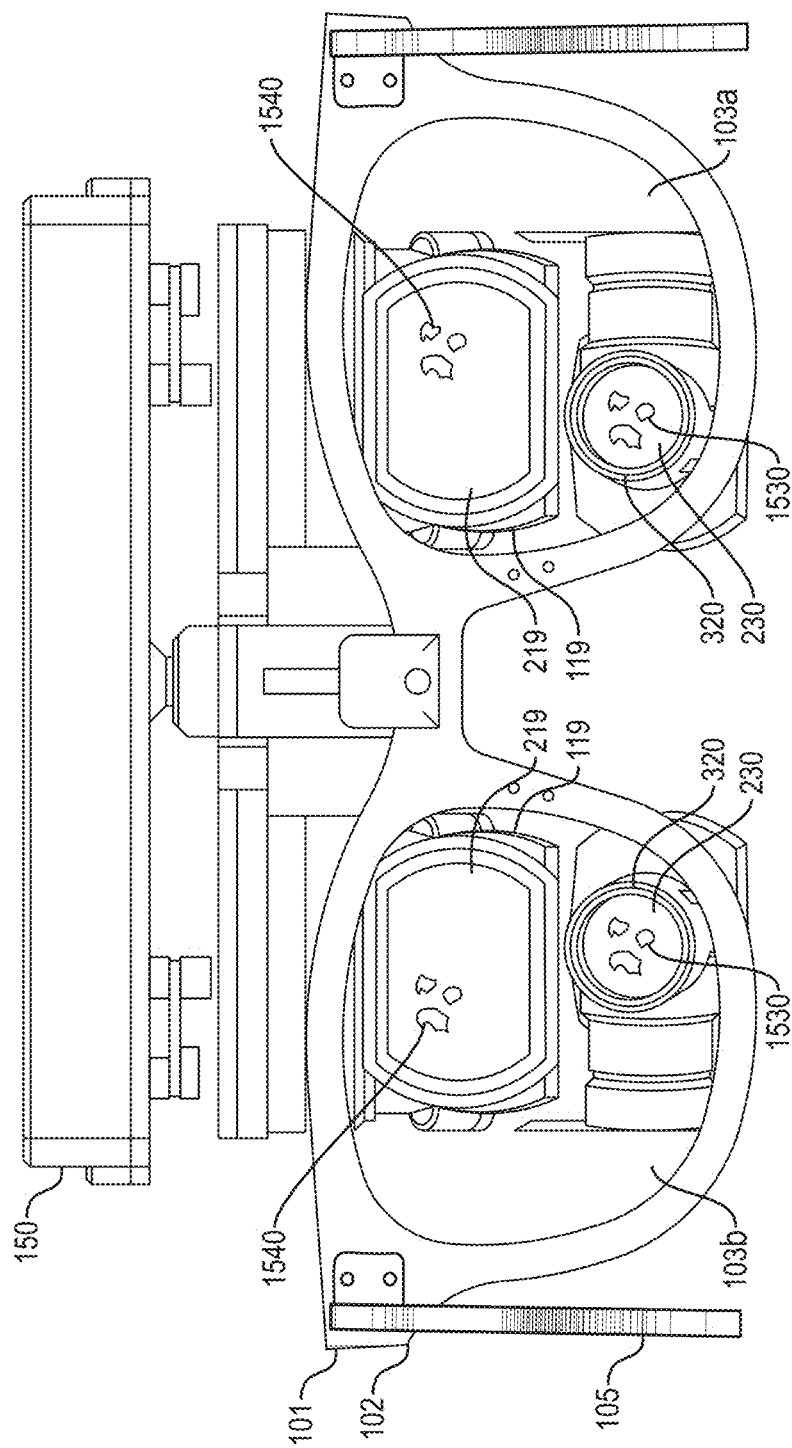

FIG. 15B illustrates an exemplary presentation of image data that may be presented to a user in accordance with the principles of the invention.

In this illustrated presentation, images 1540 viewed through integrated viewing/capturing system 320 may be presented on display screen 219 such that images 1540 correspond to images 1520 presented on eye-lens 230.

Figure 15C:
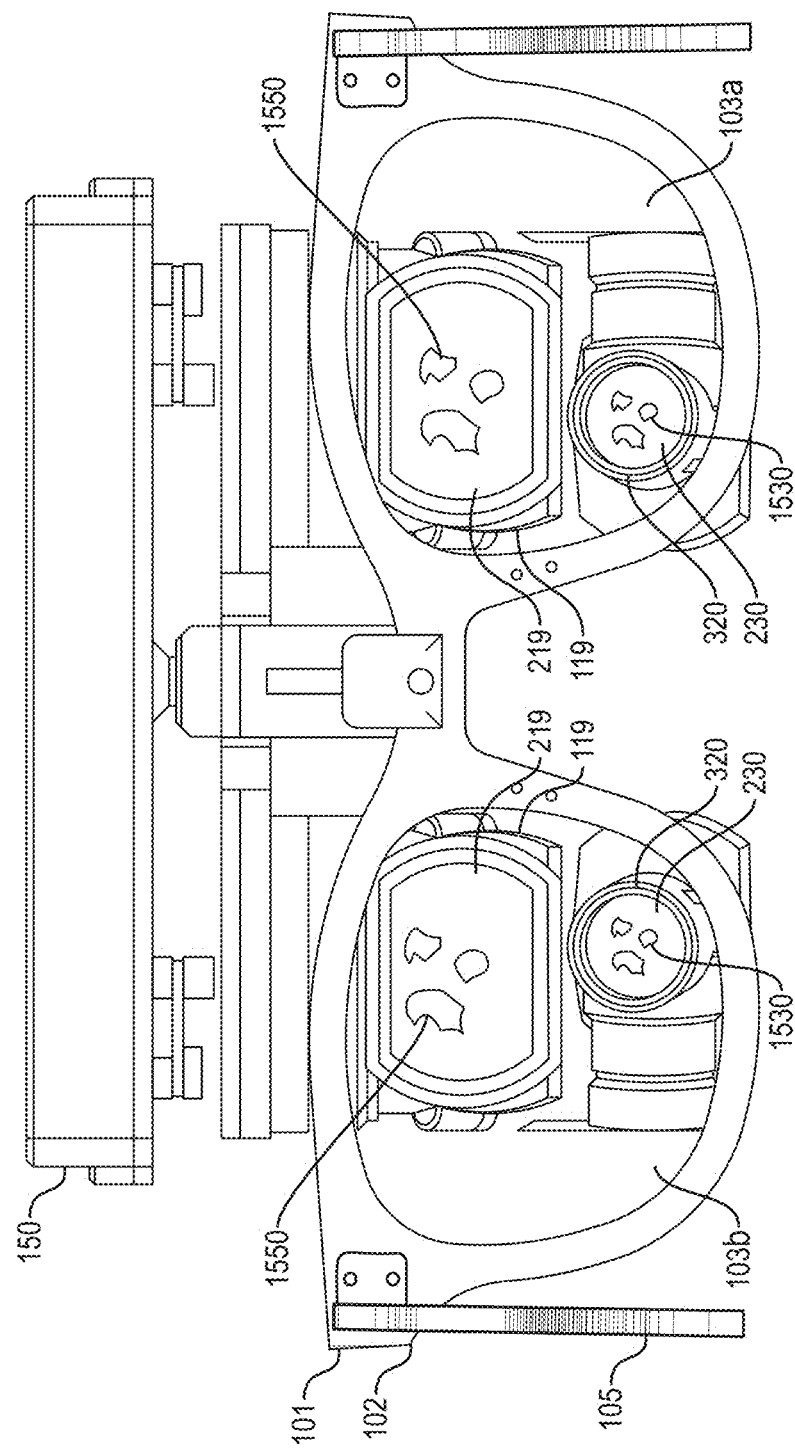

FIG. 15C illustrates an exemplary presentation of image data that may be presented to a practitioner in accordance with the principles of the invention.

In this illustrated presentation, which is similar to that shown in FIG. 15B, the images 1550 viewed on display screen 219 are digitally enlarged over images 1530 viewable through integrated viewing/capturing system 320.

Alternatively, images 1530, 1550 may represent digitally enhanced images (e.g., higher contrast, less noise, etc.) of images 1530, wherein the enhanced images 1530, 1550 may be obtained through the post-processing of images of objects collected under different lighting conditions (e.g., concurrent ambient or white, and infra-red lighting).

Figure 16:
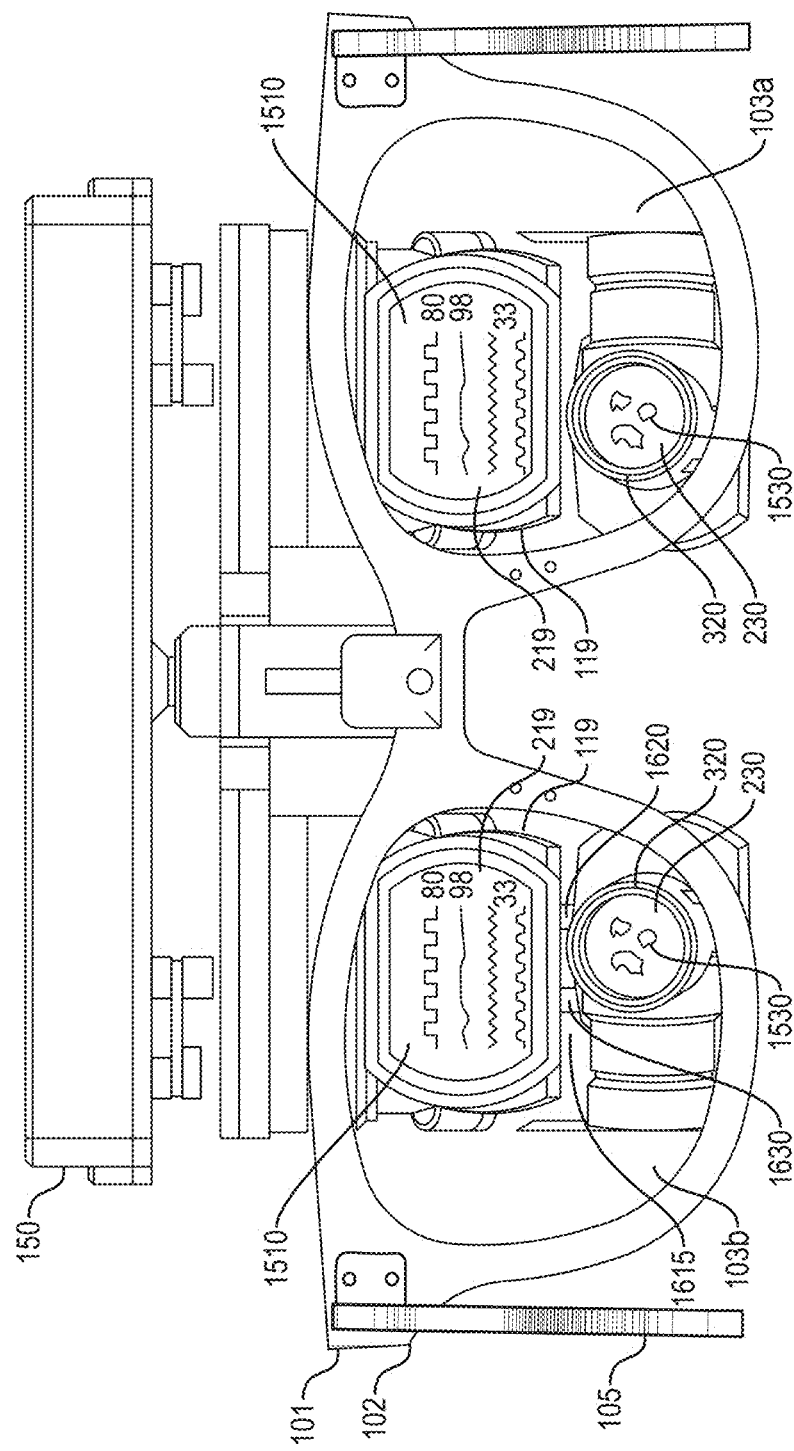
FIG. 16 illustrates an exemplary embodiment of a switching means suitable for controlling presentation of data on the exemplary display systems shown herein.

FIG. 16 illustrates an exemplary embodiment of a switching means for altering the information presented on the display systems in accordance with the principles of the invention.

In accordance with this aspect of the invention, a sensor switch 1615 comprising a transmitting unit 1620 and a receiving unit 1630 (or a single transceiving unit) may be incorporated onto or within one of integrated viewing/capture system 320 and display system 119 previously discussed (see FIG. 15A, for example).

In this exemplary embodiment, transmitting unit 1620 may comprise an active transmitting unit that emits a signal toward a user's eye (not shown). The transmitted signal may be one of a light (e.g., infra-red) and an ultra-sonic that is directed to the user's eye. Receiving unit 1630, response to receiving a reflection of the transmitted signal may determine a position of the user's eye with respect to one of eye-lens 230 or display screen 219. A determination of a position of the practitioner's eye may be made based, in part, on the intensity of the received signal.

In accordance with the principles of the invention, the presentation of information shown on display screen 219 may be altered with the determination of different eye movements. For example, a presentation, such as shown in FIG. 15A, may be initially presented to a practitioner, who may alter the position of their eye (or momentarily close their eye) to change the display presentation to that shown in FIG. 15B. A further alteration of the position of the eye (or a closure of the eye) may further alter the display presentation to that shown in FIG. 15C.

In one aspect of the invention, the alteration of the position of the eye to cause a change in display presentation may be in an up and/or down movement. In another aspect of the invention, the alteration of the position of the eye may be one of left to right or right to left.

In another aspect of the invention, the illustrated sensor may represent a passive unit, such as a camera or CCD sensor, which may monitor the position of the practitioner's eye. In still another aspect of the invention, the alteration of the display presentation may be achieved with the previously illustrated switches (1015, 1115, 1125) wherein the discussed switch(es) may include both a lighting control element and a display control element.

Figure 17A:
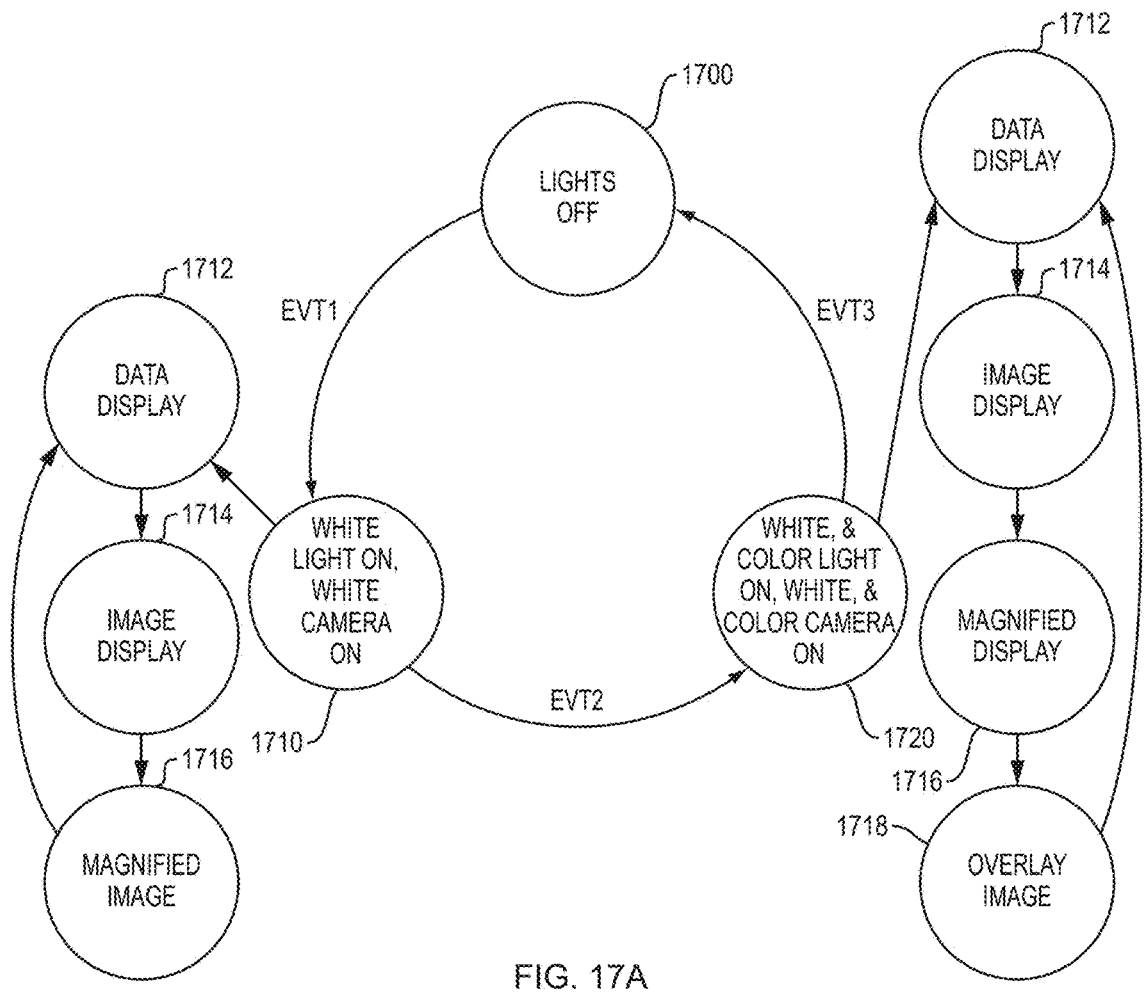
FIGS. 17A-17B illustrate state diagrams of exemplary processing in accordance with the principles of the invention.

FIG. 17A illustrates a state diagram of an exemplary processing associated with the control of head-borne examination/visualization/collection system with light enhancement shown herein.

In this exemplary state diagram, the illustrated lighting element(s) and camera (sensor) element(s) are in an initially OFF-state (state 1700).

In accordance with the principles of the invention, with the detection of a first event (EVT1) (e.g., by the depression of, or the detection of a proximal element near, switch 1015, 1115, 1125, etc.) white light lighting source and an associated image capture device (i.e., white light camera) for collecting images under white or ambient may be turned to an "ON" state (state 1710), wherein images of objects may be viewed through the magnification devices 117 and images may be concurrently collected by image capture devices 270).

With the detection of a second event (EVT2) (e.g., by the depression of, or the detection of a proximal element near, switch 1015, 1115, 1125, etc.), the white light and colored light lighting sources are turned to an ON state (state 1720), and the camera elements (e.g., white and colored or IR cameras) are also turned to an ON" state, wherein images of an object may be captured under both a white light and a colored or IR light).

In one aspect of the invention, an intensity of the white light source emitted at state 1720 may be significantly reduced as compared to the intensity of the white light source emitted when in state 1710. Alternatively, the intensity of the white light source may be reduced to a near-zero level, when in the lighting system is in state 1720.

Although, a two different camera configuration is discussed as being incorporated into visualization system 110 or visualization system 320 and may be turned to an "ON" state concurrently it would be understood that a single camera configuration may be incorporated into visualization system 110 or visualization system 320 without altering the scope of the invention.

Further illustrated are exemplary processing states for presentation of the concurrent display of data onto display screens 219*a*, 219*b* (shown in FIGS. 15A-15C), for example.

In this illustrated exemplary process, when the visualization/collecting system discussed herein enter a first state (i.e., state 1710), display screens 219*a*, 219*b* may be turned to an "ON" state to present biometric or similar data (see FIG. 15A). With subsequent detections of a change in eye-position, sensors 1620/1630, shown in FIG. 16, may operate to alter the information on display screen 219*a*, 219*b* from biometric data (FIG. 15A) to image data (FIG. 15B) and magnified image data (FIG. 15C).

This sequence of displays continues while the visualization/collecting system remains in state 1710.

However, with the detection of a second event (EVT2), and the entry into state 1720 displays 219*a*, 219*b* may present data, sequentially, through states 1712, 1714, and 1716. In addition, the use of image capture devices that capture images under different lighting conditions (e.g., white light/IR light) allows for the post-processing of the captured images to create an overlay image of the object that provides for higher contrast image to be viewed (state 1718).

This sequence of displays continues while the visualization/collecting system remains in state 1720.

Figure 17B:
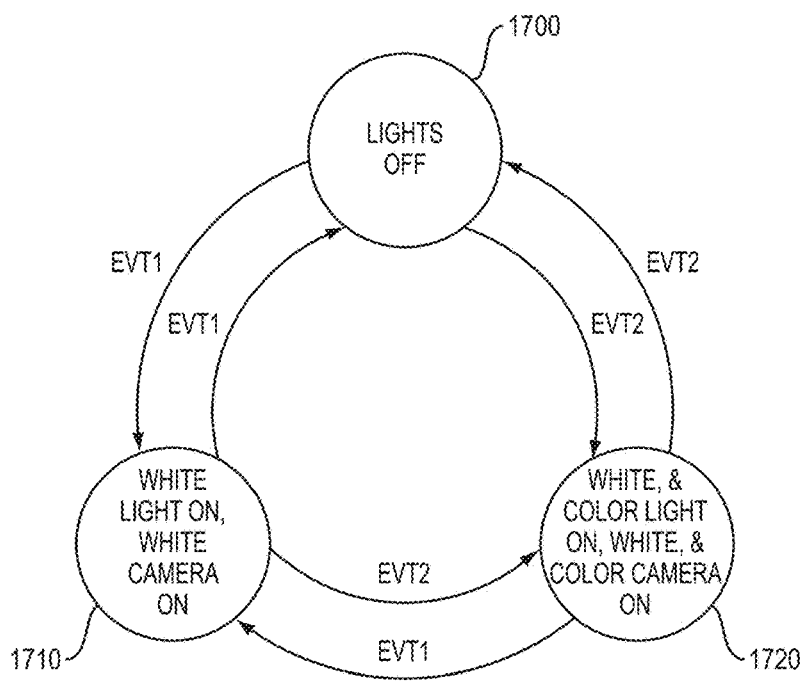

FIG. 17B illustrates a second exemplary embodiment of processing in accordance with the principles of the invention.

In this illustrated second exemplary embodiment, the status of lighting elements and image capture devices is altered based on the detection of an event (e.g., depression of switch 1510). In this embodiment, which includes processing similar to that shown and discussed with regard to FIG. 17A, the status of the lighting elements and cameras transition from one state (e.g., 1700 to 1710) with the detection of a first event (EVT1). However, in this illustrated embodiment, the processing shown need not be sequential, as the transition to a next state is based on a current state and which of the illustrated two events occurs.

In addition, while not shown, it would be recognized that the display sequence discussed above with regard to FIG. 17A may be incorporated into this second exemplary embodiment of processing without undue experimentation.

While the exemplary embodiments of processing shown in FIGS. 17A, 17B are discussed with regard to switch 1015 and sensor switch 1620/1630, it would be recognized that the processing disclosed may be performed with a single switch 1015 that provides for multiple different switch configurations.

Figure 18:
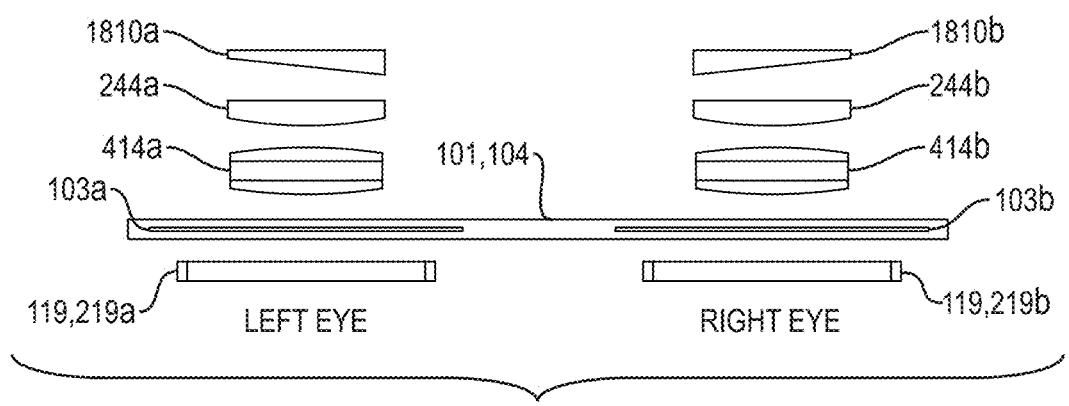
FIG. 18 illustrates a top view of a further aspect of an examination/visualization system that provides a three-dimensional presentation in accordance with the principles of the invention.

FIG. 18 illustrates a top view of a further aspect of an examination/visualization system that provides a three-dimensional presentation in accordance with the principles of the invention.

In this aspect of the invention, a three-dimensional representation of an object viewed on display screen 219 may be presented to the practitioner, wherein t images presented on display screen 219, may be viewed through collimating lens 415 and spectral correction lens (if need) 244, as previously discussed (see FIG. 4B).

Further illustrated is base-in prismatic (wedge) lens 1810*a*, 1810*b*, associated with lenses 103*a*, 103*b*, respectively, wherein wedge lens 1810*a*, 1810*b* are oriented such that the base element is directed toward the bridge element 104 of eyewear 101. Wedge lens 1810*a*, 1810*b* allow for an alternation of the light path from display screen 219 (e.g., 219*b*) to make the image of the object being viewed, when combined (through post-processing) with the image from display 219*a* in three dimensions (i.e., 3D).

Figure 19A:
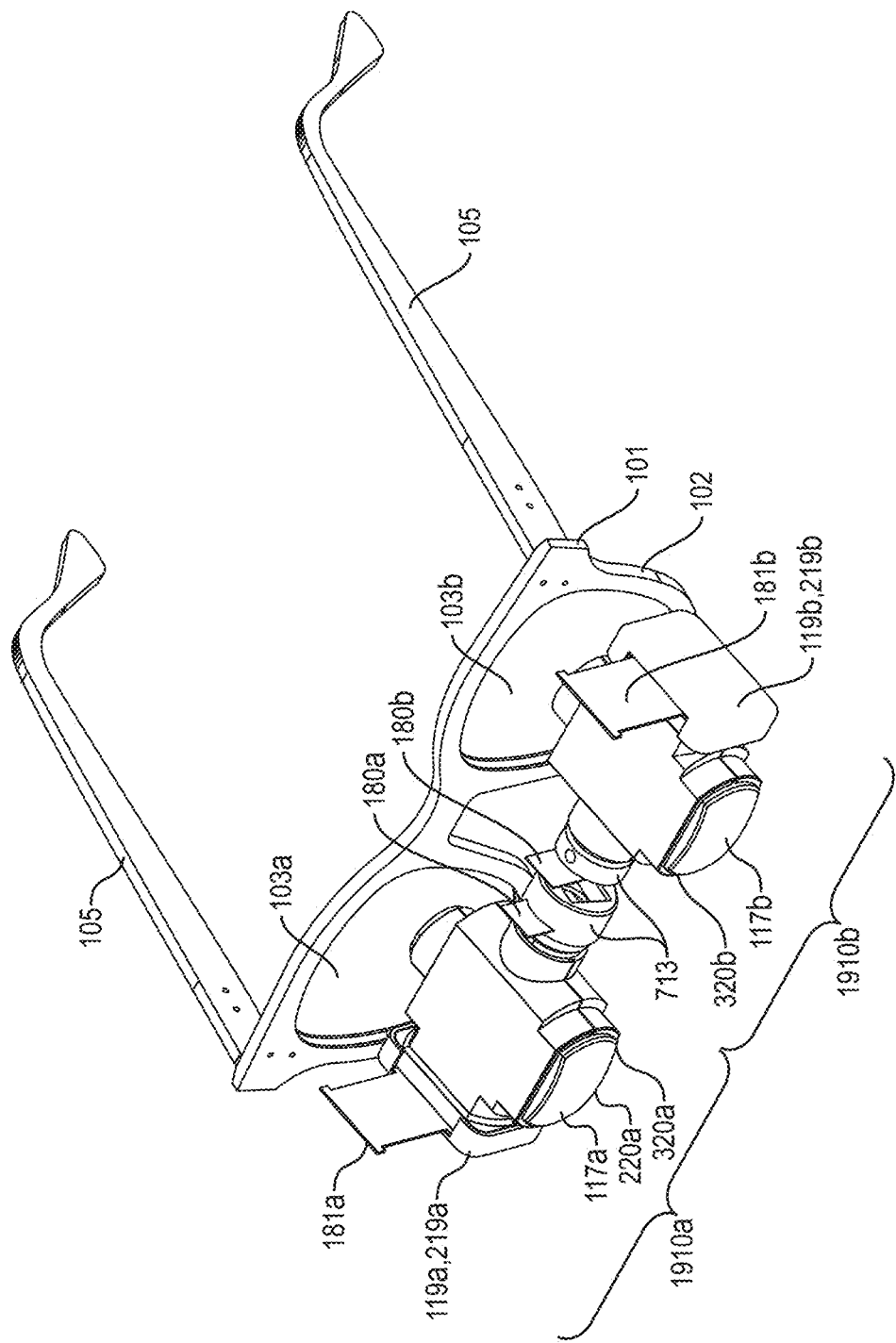
FIG. 19A illustrates a perspective view of a first aspect of a fourth exemplary embodiment of head-borne examination/visualization/collection system in accordance with the principles of the invention.

FIG. 19A illustrates a perspective view of a first aspect of a fourth exemplary embodiment of head-borne examination/visualization/collection system in accordance with the principles of the invention.

In accordance with this exemplary embodiment is shown eyewear 101, including lenses 103*a*, 103*b* and temple elements 105, as previously discussed. Further illustrated is visualization system 1910*a* incorporated into lens 103*a* and visualization system 1910*b* incorporated into lens 103*b*.

Visualization system 1910 comprises an integration of display system 119 into the previously disclosed viewing/capturing system 320, comprising magnification section 117 and offset image capture section 713, to create a fully integrated visualization system.

Fully integrated visualization system 1910 operates in a manner similar to the visualization systems 110, 310, previously discussed, wherein objects viewed through magnification section 117 are viewable by a practitioner, concurrently captured by an image capture device (not shown) within offset image capture section 713 and displayed on display screen (not shown) of display 119. Further shown are wired communication 181*a*, 181*b* connected to displays 119*a*, 119*b* respectively and wired communication 180*a*, 180*b* connected to offset image capture assembly 713*a*, 714*b*, respectively.

Figure 19B:
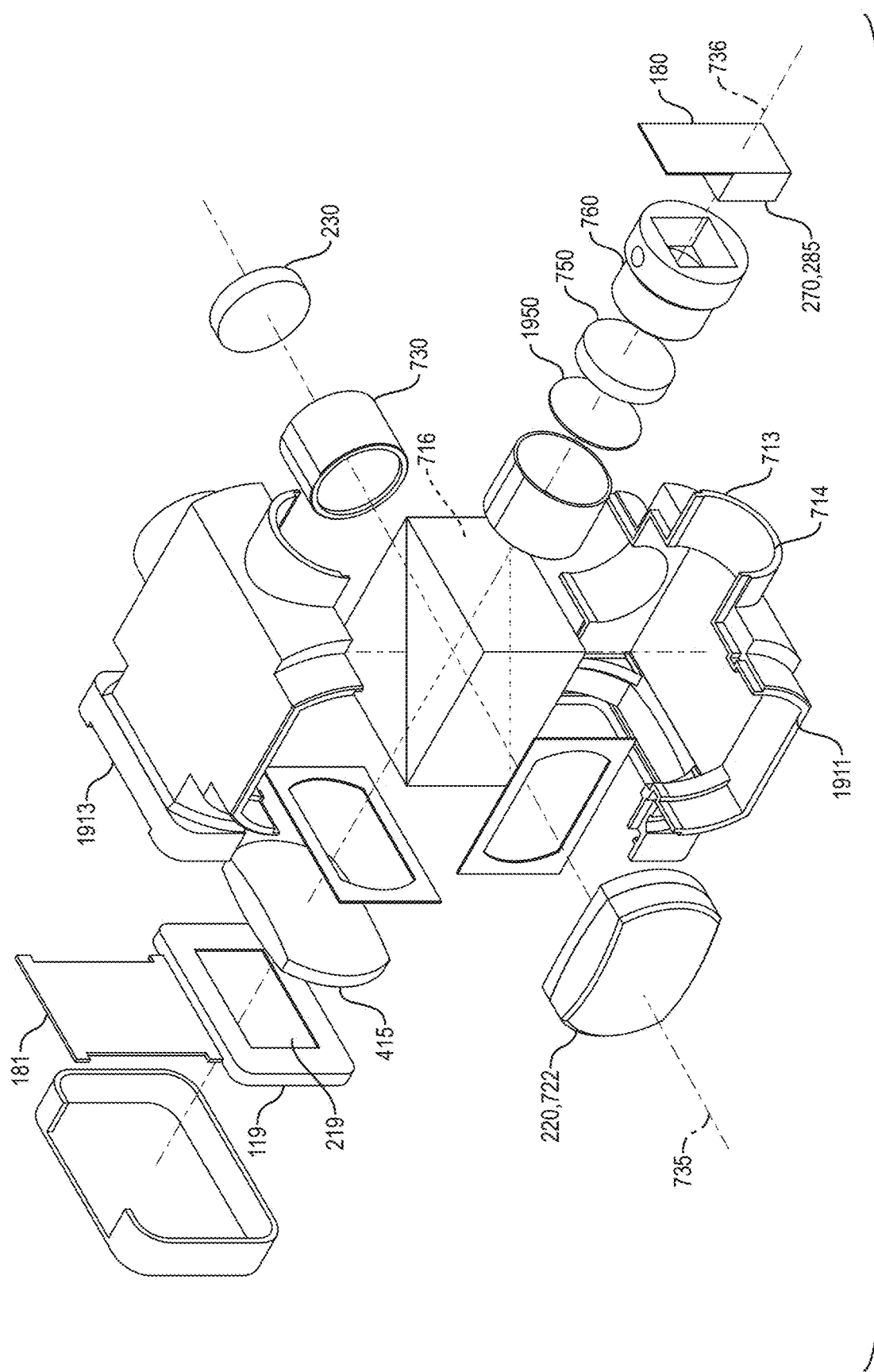
FIG. 19B illustrates an exploded perspective view of the examination and visualization system shown in FIG. 19A.

FIG. 19B illustrates an exploded perspective view of the examination and visualization system shown in FIG. 19A.

In this illustrative embodiment, visualization system 1910 comprises housing 1911 including, therein, objective lens 220 (and included working lens 722), splitter 715 and eye-lens 230 contained within eye piece 730. Objection lens 220 and eye-lens 230 forming first optical axis 735. Further illustrated is offset image capture section 713 containing, therein, image capture device 270 (with lens 285) and second eye-lens 750 contained within sensor housing 760. Objective lens 220 and second eye-lens 750 forming second optical axis 736. As shown, first optical axis 735 and second optical axis 736 are in a same plane.

Further illustrated is second offset section 1913 within housing 1911. Second offset section 1913, arranged orthogonal or substantially orthogonal to optical axis 735, enables the placement of display system 119 (and display screen 219) to project images into housing 1911 toward light director 715 along optical axis 736.

Further illustrated is polarization lens 1950 and collimating lens 415 positioned within offset image capture section 713. Polarization lens 1950 is configured to block light of a known polarization from being received by image capture device 270, wherein collimating lens 415, which as previously discussed, provides for rendering the light associated with the images shown on display screen 219 to be parallel or substantially parallel. The light of the displayed images may then, when viewed through eye-lens 230, be properly focused onto a user's retina.

Figure 19C:
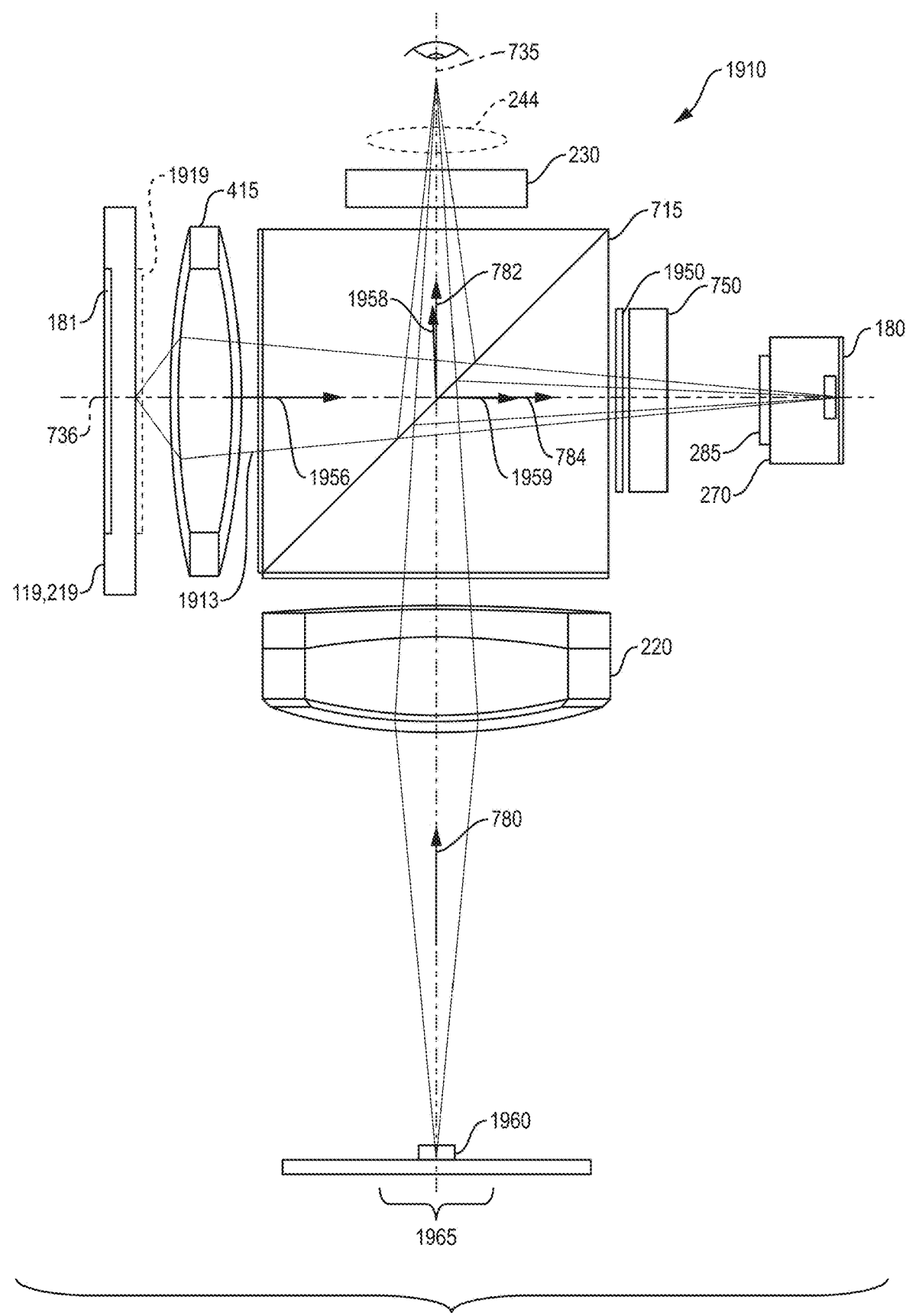
FIG. 19C illustrates a top view of the examination and visualization system shown in FIG. 19A.

FIG. 19C illustrates a top view of the examination and visualization system shown in FIG. 19A.

In this illustrated view, light 780 emitted by (or reflected off of) object 1960, within a FoV 1965, and travelling along axis 735, is viewed through objective lens 220 and presented to light director 715, which divides the light into two components 782 and 784 (see FIG. 7A). Light 782, proceeding through to eye-lens 230, along axis 735, provides a magnified view of object 1960 and light 784, proceeding, along axis 736, through second eye-lens 750 is captured by image capture device 270.

Further illustrated is display screen 219, which presents images of objects captured by image capture device 270. In this aspect of the invention, light 1956 associated with images presented on display screen 219 is directed, along axis 736, through second offset opening 1913 and collimating lens 415 toward light director 715. As previously discussed, display screen 219 is positioned at a focal length of collimating filter 415 to render the light emitted by display screen 219 substantially parallel as the light is directed toward light director 715. In a manner similar to light 780, light director 715 directs light 1956, along axis 735, toward eye-lens 230 (i.e., light 1958) and, along axis 736, toward image capture device 270 (light 1959).

In accordance with the principles of the invention, light 1959 is prevented from being viewed by image capture device 270 by the intervention of polarization filter 1950 that blocks light lacking a known polarization from passing through. Hence, the practitioner is enabled to concurrently view a magnified view of object 1965 and a processed view of object 1965. As would be known in the art, thin film transistor (TFT) screens or liquid crystal displays (LCD) screens generally emit a polarized light (by the addition of a polarized film on the display screen) and, thus, polarizing lens 1950 is oriented ninety (90) degrees out-of-phase to block the emitted light from display screen 219.

Although polarization filter 1950 is shown, it also would be known in the art that should display screen 219 not include a polarization film, then a polarizing lens or film 1919 may alternatively be added to display screen 219 to polarize to emitted from screen to 219 to block the light emitted by display screen 219 from being received by image capture device 270.

Further illustrated is spectral correction lens 244, which as previously discussed, may be incorporated into the fully integrated viewing/collection system 1910, should the user require such image correction to obtain a focused image to the user.

Figure 20:
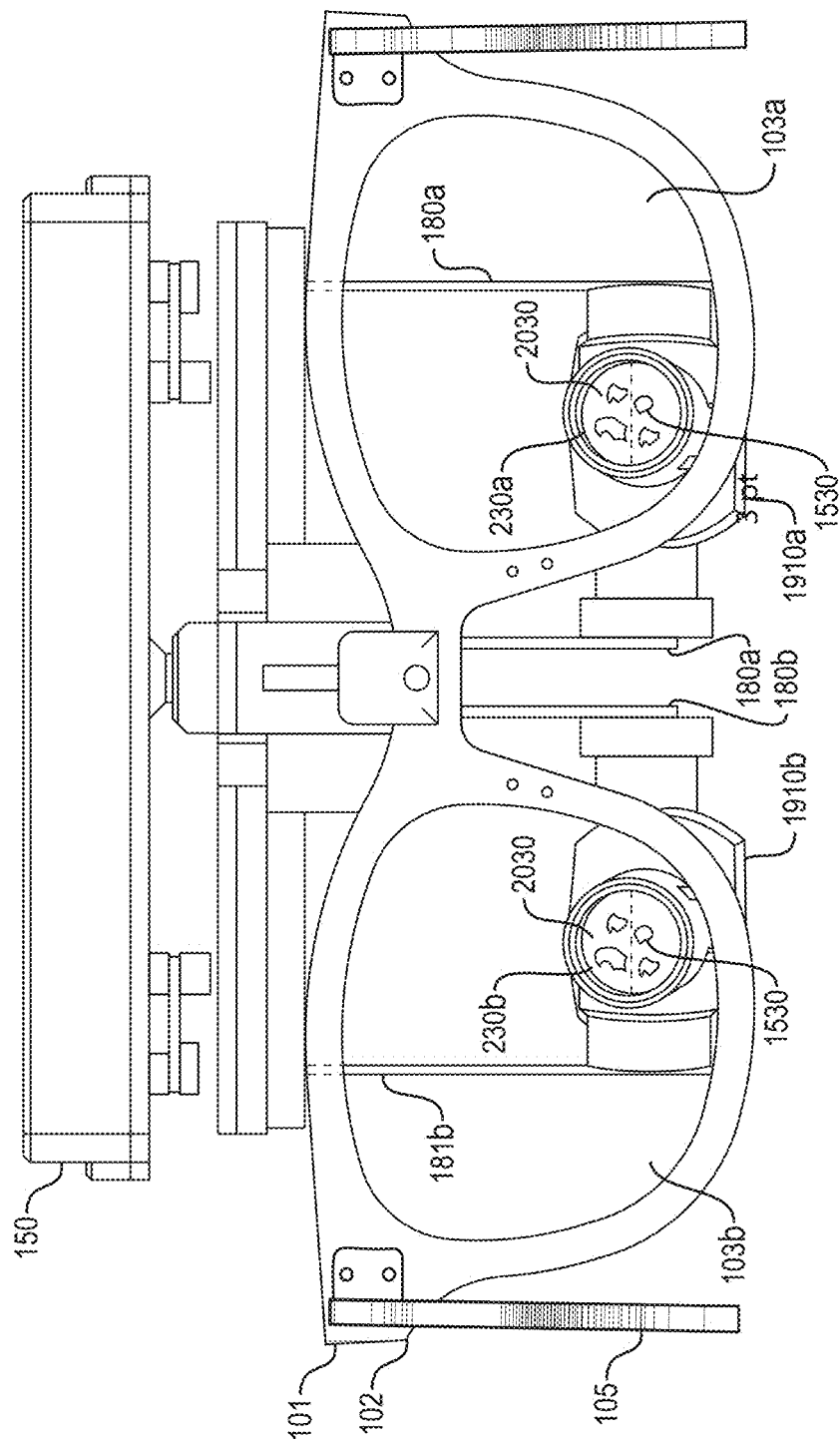
FIG. 20 illustrates an exemplary display associated with the examination/visualization system shown in FIGS. 19A-19C.

FIG. 20 illustrates an exemplary display associated with the examination/visualization system shown in FIGS. 19A-19C.

FIG. 20, similar to FIGS. 15A-15C, illustrates a rear view of eyewear 101 comprising lenses 103a, 103b.

Further illustrated is image data 1530 shown on eye-lenses 230a, 230b, and corresponding image data 2030, concurrently shown through eye-lenses 203a, 203b.

In this illustrated aspect, image data 2030 may represent one of: images of object 1960 obtained at a same level of magnification as that of object 1960 obtained through magnification section of device 1910, images of object 1960 obtained at a different level of magnification than that of object 1960 obtained through magnification section (i.e., 117) of device 1910, or an overlay of an image of object 1960 when object 1960 is illuminated under different lighting conditions (e.g., white light and IR light, white light and blue light, etc.) wherein images are concurrently captured by a white light and an infra-red camera, for example. In addition, biometric data may be presented through eye-lenses 230a, 230b, as previously discussed.

Figure 21:
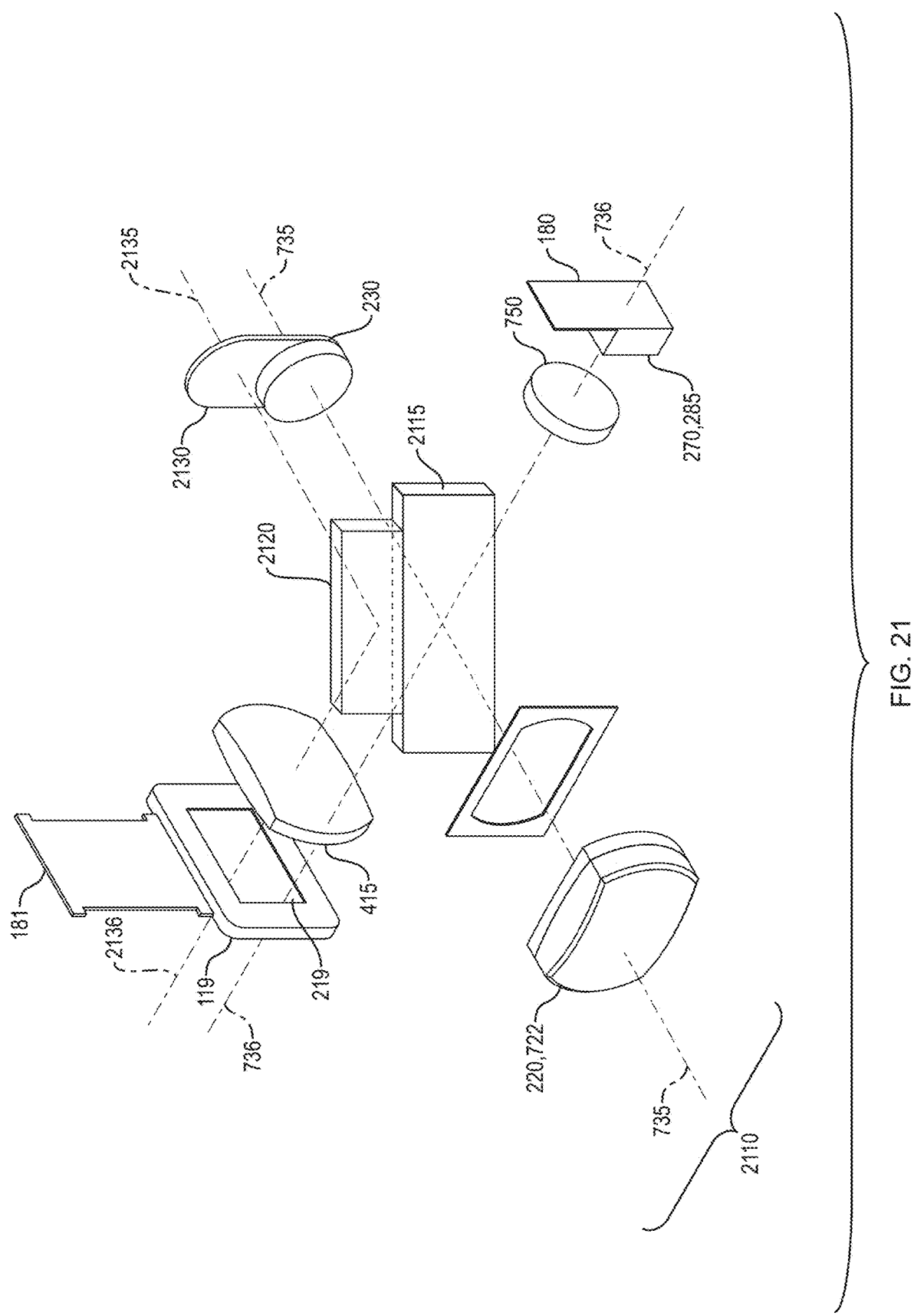
FIG. 21 illustrates a perspective view of a second aspect of the fourth exemplary embodiment of the examination/visualization system shown in FIG. 19A.

FIG. 21 illustrates a perspective view of a second aspect of the fourth exemplary embodiment of the examination/visualization system shown in FIG. 19A.

In this second aspect, visualization system 2110, which is similar to system 1910, comprises a fully integrated display 119 and viewing/collecting system 320, wherein a user may concurrently view object 1960 through magnification section 117 of system 320 and collected images of the viewed object 1960 presented on display 219.

In accordance with this aspect of the invention, light associated with object 1960 (not shown) travels along axis 735 through objective lens 220 toward eye-lens 230, wherein a magnified view of object 1960 is presented to the practitioner by the magnification capability of objective lens 220/eye-lens 230. Light from object 1960 is further directed, by light director 715, along axis 736 toward image collection device 270, wherein a magnified image of object 1960 is captured.

Further illustrated is display screen 219 configured to emit light (associated with a collected image) along axis 2136 (i.e., a third optical axis), which, as shown, is positioned offset from axis 736, wherein light associated with images displayed on display screen 219 is directed to reflective surface 2120 (e.g., mirror). Reflective surface 2120, proximal to light director 2115, is oriented to direct light, along axis 2135 (i.e., a fourth optical axis) toward display lens 2130, wherein a user may view an image displayed on display screen 219.

In accordance with this second aspect of a fully integrated visualization system 2110, a concurrent view of a magnified image of object 1960 through eye-lens 230 and a displayed image of object 1960 may be presented on display lens 2130 may be presented to a user. In one aspect of the invention, lens 2130 may be a plano lens.

Although not shown it would be understood that a spectral correction lens 244 may be included with eye-lens 230, as previously discussed (see FIG. 4B) and incorporated into lens 2130.

In addition, although axes 2135 and 2136 are shown vertically offset from axes 735 and 736 respectively, in a positive direction (i.e., in a plane above a plane formed by axes 735, 736) it would be recognized that axes 2135 and 2136 may be vertically offset from axes 735 and 736, respectively, in a negative direction (i.e., in a plane below a plane formed by axes 735, 736). Similarly, axes 2135 and 2136 may be offset from axis 735 and 736 in a horizontal direction.

Figure 22:
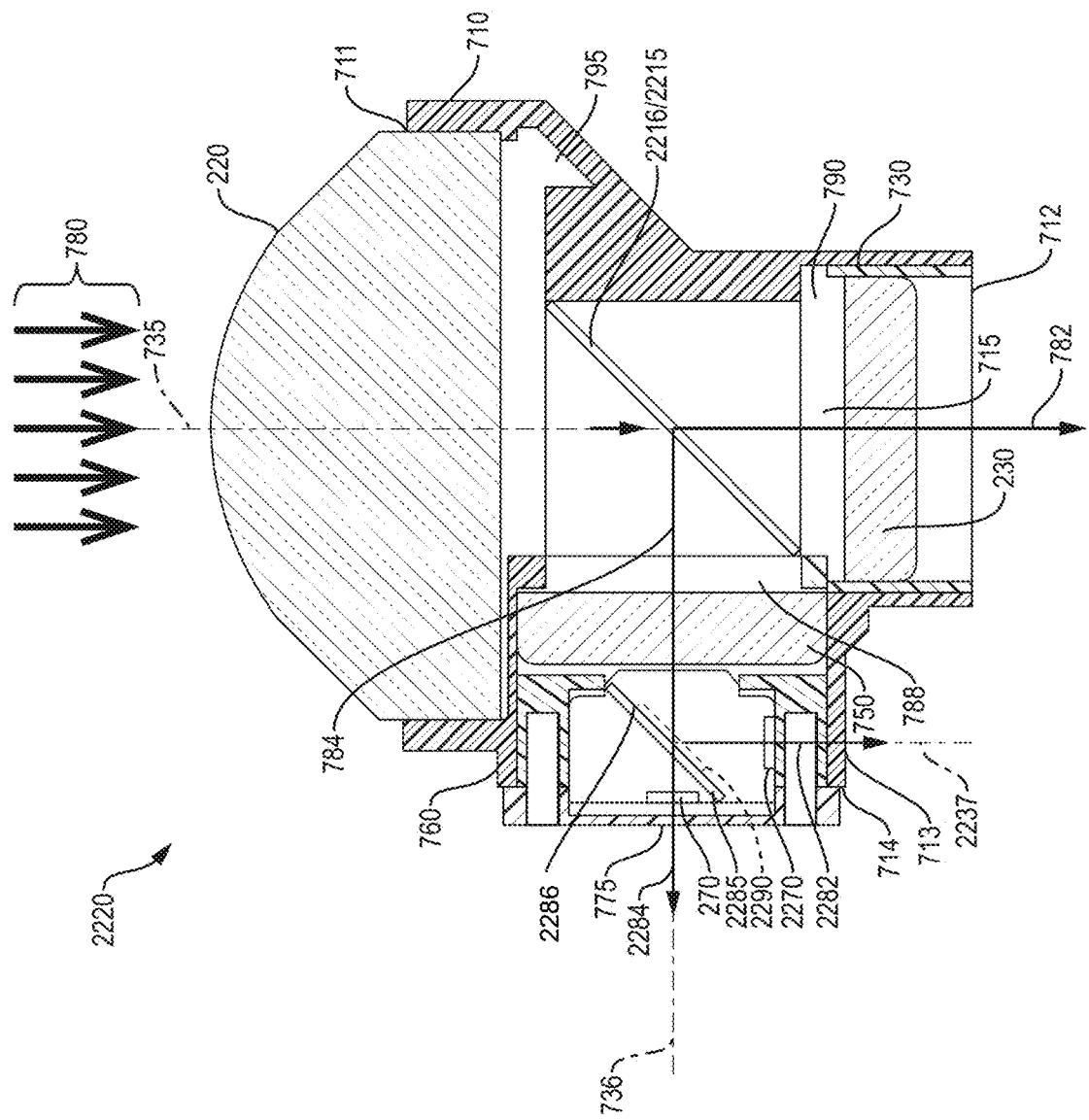
FIG. 22 illustrates a cutaway top view of a still further exemplary embodiment of a viewing/capture system in accordance with the principles of the invention.

FIG. 22 illustrates a cutaway top view of a still further exemplary embodiment of a viewing/capture system in accordance with the principles of the invention.

In this illustrated exemplary embodiment, which is similar to the embodiment shown in FIG. 7D, viewing/capture system 2220 comprises objective lens 220, eye-lens 230 and light director 2215, which includes partially transmission/partially reflective surface 2216. In this illustrated embodiment light director 2215 is presented as a plate splitter. However, it would be recognized that light director 2215 may be presented as one of a block beam splitter, a thin film beam splitter, Pellicle beam splitter, or polka dot beam splitter, without altering the scope of the invention claimed.

As this illustrated embodiment includes elements that are common to and identified with the same reference labels as those elements discussed with regard to the configuration shown in FIG. 7D, a full understand of the operation of those element may be obtained by those skilled in the art by reference to the discussion with regard to FIG. 7D. Accordingly, a further detailed discussion of similar or common elements between the elements shown in FIG. 7D and the elements shown in FIG. 22 is believed not needed to understand the principles of the embodiment shown in FIG. 22.

In accordance with this aspect of the invention, included within offset image capture section 713 is image capture device 270 positioned to capture light 784, which is reflected by light director 2215 along second optical axis 736, in a manner similar to that discussed with regard to FIG. 7D.

Further illustrated within offset image capture section 713 is second light director 2285, positioned offset from (i.e., at an angle with respect to) second optical axis 736. Second light director 2285, similar to light director 2215, also includes a partially reflective/partially transmission surface 2286 and may be represented as one of a block beam splitter, plate beam splitter, a thin film beam splitter, Pellicle beam splitter, or polka-dot beam splitter, etc. Similar to light director 2215/2216, second light director 2285/2286 is configured to allow a known amount of light 784 travelling along second optical axis 736 to pass through (i.e., light 2284) to image capture device 270 and to re-direct (i.e., reflect) on to optical axis 2237, a second known amount of light 784 (i.e., light 2282). As would be recognized the amount of light that may be transmitted or passed to image capture device 270 (i.e., light 2284) may be similar to, or different than, the amount of light (i.e., light 2282) reflected by reflective surface 2285/2286. For example, light director 2285/2286 may include transmissive/reflective properties that allow for 90 percent of light 784 to pass through to image capture device 270, while 10 percent of light 784 is reflected along optical axis 2237. Alternatively, light director 2285/2286 may possess transmissive/reflective properties corresponding to 80/20, 70/30, etc. In one aspect of the invention, the transmissive/reflective properties associated with light director 2286/2286 may be determined, in part, by the transmissive/reflective properties associated with light director 2215/2216.

In accordance with this embodiment of the invention, further illustrated is second image capture device 2270 positioned within offset image capture section 713. Second image capture device 2270 is configured to capture light (i.e., light 2282) travelling along optical axis 2237, wherein the captured light is associated with an object (not shown) in a manner as previously discussed.

In one aspect of the invention, wherein image capture device 270 may represent device suitable for capturing images under normal or ambient I (i.e., light within the surrounding environment of an object at or near viewing point, e.g., daylight, artificial light, etc.) light conditions and image capture device 2270 may represent a device suitable for capturing images under light in a different wavelength range (e.g., infra-red light). Alternatively, image capture device 2270 may capture images in one or more different wavelength ranges.

In this aspect of the invention, both light directors 2216/2215 and 2286/2285 may reflect incoming light 780, 784 respectively, wherein image capture device 2270 may capture images associated with light in an infra-red wavelength band while ignoring or not processing light outside the infra-red wavelength band. Similarly capture device 270 may capture images associated with light in an ambient or surrounding environment (e.g., white) wavelength range and ignore or not process light in a wavelength band outside the ambient wavelength band. For example, when light within a surrounding area around an object is within a blue wavelength range (i.e., light emitted is within a blue wavelength range), image capture device 270 may process light within the ambient light wavelength range (or a portion of the ambient light wavelength range) and ignore light outside the ambient light wavelength range.

In accordance with one aspect of the invention, reflective surface 2286 may include, or comprise, a filter element 2290 that operates as a high-pass filter (in the frequency domain or low-pass filter in the wavelength range), wherein wavelengths associated with an ambient light (i.e., light surrounding an area) is passed though surface 2285 toward image capture device 270 (i.e., below a known wavelength) while wavelengths associated with infra-red light (i.e., above the known wavelength) is reflected by filter 2290 toward image capture device 2270. In this aspect of the invention image capture device 2270 may collect light in the Infra-red wavelength range associated with an image. However, it would be understood that alteration of the positioning of ambient device 270 and IR device 2270 would be within those skilled in the art and is considered within the scope of the invention claimed.

Figure 23:
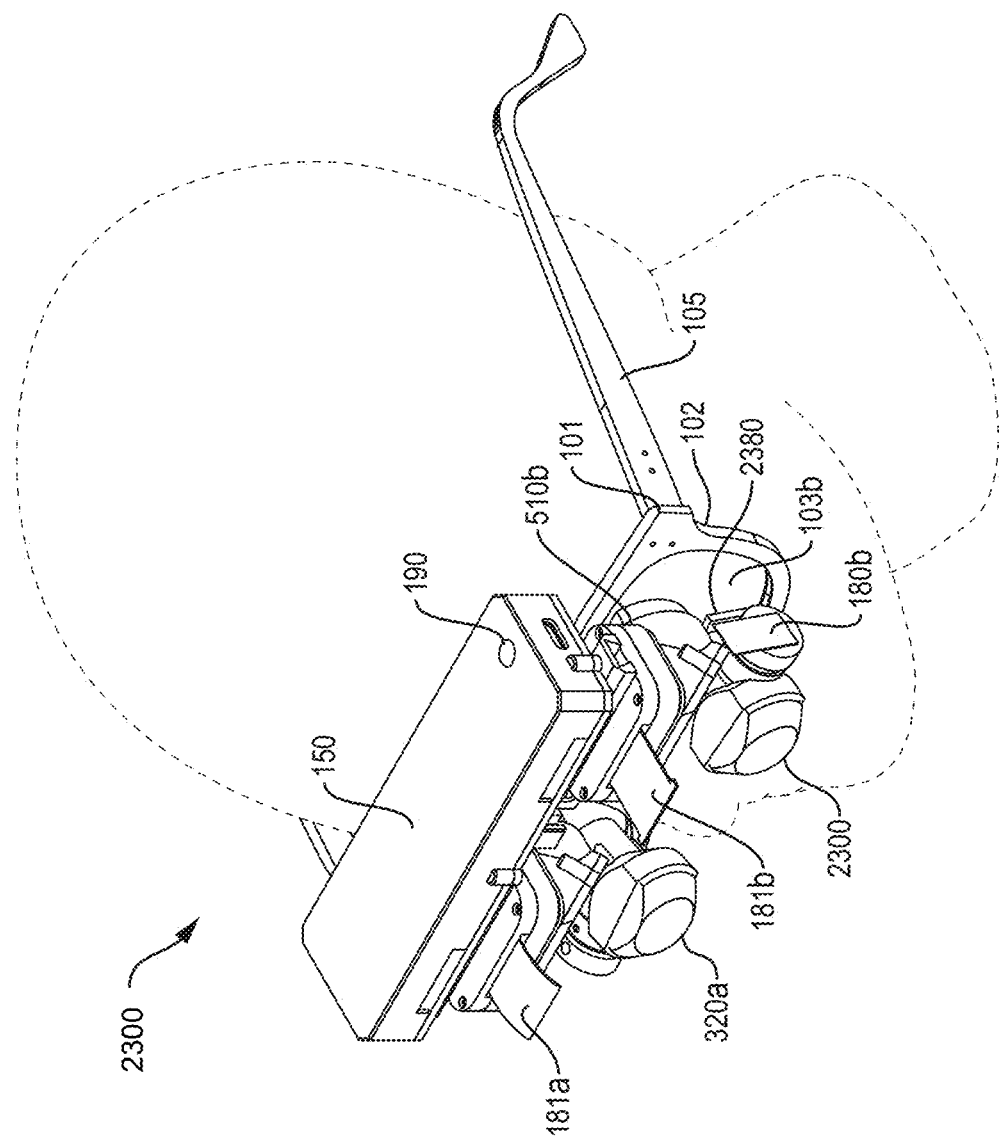
FIG. 23 illustrates a perspective view of an examination and visualization system utilizing the viewing/capture system shown in FIG. 22.

FIG. 23 illustrates a perspective view of an examination and visualization system utilizing the capturing/recording system shown in FIG. 22.

In this illustrated exemplary embodiment, which is similar to the embodiment disclosed with regard to FIG. 5A, examination/visualization system 2300, comprises eyewear 101 including first lens 103*a* and second lens 103*b* and at least one viewing/capturing systems 2300 incorporated into, in this illustrated example, second lens 103*b*.

As this illustrated embodiment includes elements that are common to and identified with the same reference labels as those elements discussed with regard to the configuration shown in FIG. 5A, a full understanding of the operation of those elements that are identified as being common to both FIG. 5A and FIG. 23 may be obtained by those skilled in the art by reference to the discussion with regard to FIG. 5A. Accordingly, a further detailed discussion of similar or common elements is believed not needed to understand the principles of the embodiment shown in FIG. 23.

As is shown, image capture device 270 (not shown) is in wire-ed connection 180*b* to electronic assembly 150, wherein images captured by image capture device 270 (not shown) are transmitted to electronic assembly 150. Further illustrated is wire-ed connection 2380, which is associated with image capture device 2270 (not shown). Wire-ed connection 2380 provides images captured by image capture device 2270 (not shown) to electronic assembly 150.

Images processed by electronic assembly may subsequently, through connections 181*a*, 181*b*, be presented to a display system, as previously discussed.

In summary, multiple embodiments of a head-born user-wearable examination/visualization/collection system with light enhancement have been disclosed, wherein the viewing and collection of images or video under natural (i.e., white) light and/or colored light (non-white) and/or non-visible (e.g., Infra-Red) conditions is discussed and the collected images may be processed and presented to a user on display that is local to the visualization device. Further disclosed are different configurations of lighting assemblies and viewing capturing/recording devices, wherein the lighting assemblies provide for the light necessary to collect images under natural light and colored light and the capturing/recording devices allow for the collection of images of a viewed object in one or more light wavelength ranges.

Further disclosed is a viewing/capturing system that provides for the concurrent viewing and image capturing of an object, wherein the captured image is magnified to at least one of: a same level as that of the viewed image, a different level of magnification and an enhanced magnified image of the object. Furthermore, filters are disclosed as being incorporated into the visualization/collection device to allow for the attenuation of light in undesired wavelengths while allowing light in desired wavelengths to pass unattenuated. In still a further aspect of the invention, a second telescopic lens may be incorporated into the path of light to be captured by the image capture device, wherein the image captured and recorded is of a greater magnification than that of the user viewable image.

Although the embodiments of the lighting assemblies show the light paths as being a single line, it would be understood by those skilled in the art that the light paths represent light beams that have a desired light beam width that would form a substantially circular light pattern centered substantially about the discussed common point (i.e., 1030). In addition, the substantially circular light pattern would encompass the field of view (i.e., 1965) shown in FIG. 19C.

The invention has been described with reference to specific embodiments. One of ordinary skill in the art, however, appreciates that various modifications and changes can be made without departing from the scope of the invention as set forth in the claims. Accordingly, the specification is to be regarded in an illustrative manner, rather than with a restrictive view, and all such modifications are intended to be included within the scope of the invention.

Benefits, other advantages, and solutions to problems have been described above regarding specific embodiments. The benefits, advantages, and solutions to problems, and any element(s) that may cause any benefits, advantages, or solutions to occur or become more pronounced, are not to be construed as a critical, required, or an essential feature or element of any or all of the claims.

What is claimed is:

1. An examination/visualization system comprising:
   an eyewear comprising:
      a first lens; and
      a second lens, joined by a bridge element;
      a visualization system associated with at least one of the first lens and the second lens, the visualization system comprising:
         a viewing/collection system comprising:
            a magnification device configured to:
               magnify, by a known level of magnification, an image of an object, the magnification device comprising:
                  an objective lens; and
                  an eye-lens, the objective lens and the eye-lens forming a first optical axis; and
            an image capture assembly comprising:
               a second eye-lens, wherein the second eye-lens forms a second optical axis substantially orthogonal to the first optical axis;
               a light director positioned between the objective lens and the eye-lens, the light director configured to:
                  direct a first portion of light, associated with the object, entering the objective lens along the first optical axis to the eye-lens; and
                  reflect a second portion of the light along the second optical axis to the second eye-lens; and
               a second light director configured to:
                  receive the second portion of the light along the second axis; and
                  direct a known portion of the second portion of the light along the second optical axis toward a first image capture device, the first image capture device configured to:
                     capture an image in a first wavelength range; and
                  reflect a second known amount of the second portion of light directed along the second optical axis along a third optical axis toward a second image capture device, the second image capture device being configured to:
                     capture the image in a second wavelength range.

2. The examination/visualization system of claim 1, wherein the second eye-lens and the objective lens form a second magnification device, the second magnification device having a same level of magnification as the known level of magnification of the first magnification device.

3. The examination/visualization system of claim 1, wherein the second eye-lens and the objective lens form a second magnification device, the second magnification device having a different level of magnification than the known level of magnification level of the first magnification device.

4. The examination/visualization system of claim 1, wherein the first wavelength range comprises:
   a wavelength range in one of: an ambient light wavelength range, a white light wavelength range and a non-visible wavelength range, and
   the second wavelength range comprises:
   a wavelength range in of: an ambient light wavelength range, a white light wavelength range and a non-visible wavelength range.

5. The examination/visualization system of claim 1,
   a display system comprising:
      a display screen configured to:
         display information, wherein the display information comprises the captured image of the object in at least one of the first wavelength range and the second wavelength range; and
   an electronic assembly, in electrical communication with the image capture system and the display system, the electronic assembly configured to:

provide power to the image capture system and the display system;
receive images from the image capture system; and
present representations of the images to the display system.

6. The examination/visualization system of claim 5, wherein the display screen is positioned before a corresponding one the first lens and the second lens, or after a corresponding one of the first lens and the second lens.

7. The examination/visualization system of claim 5, wherein the display system comprises:
a display director configured to:
receive light associated with the received images; and
re-direct the received light to the display screen.

8. The examination/visualization system of claim 7, further comprising:
a display offset section incorporated substantially orthogonal to the first magnification device wherein the display screen is positioned within the display offset section.

9. The examination/visualization system of claim 1, further comprising:
an objective lens filter, the objective lens filter configured to:
block light wavelengths associated with the image being viewed through the objective lens in a first wavelength range, and
allow light wavelengths associated with the image being viewed through the objective lens in a second wavelength range to pass substantially unattenuated.

10. The examination/visualization system of claim 9, further comprising:
an eye-lens filter, the eye-lens filter configured to:
block the light wavelengths associated with the image being viewed through the objective lens in the first wavelength range, and
allow the light wavelengths associated with the image being viewed through the objective lens in the second wavelength range to pass substantially unattenuated.

11. The examination/visualization system of claim 10, wherein the objective lens filter and the eye-lens filter comprise at least one of: a high-pass filter, a long-pass filter, a short-pass filter, a low-pass filter, a band-pass filter and a notch filter.

12. The examination/visualization system of claim 1, comprising at least one of: a headband and a head strap.

13. The examination/visualization system of claim 12, wherein the electronic assembly is attached to one of: the eyewear, the headband and the head strap.

14. The examination/visualization system of claim 12, comprising:
a lighting assembly attached to at least one of: the eyewear, the headband and the head strap, the lighting assembly comprising:
at least one lighting element, the lighting assembly configured to:
emit light in at least one light wavelength range.

15. The examination/visualization system of claim 14, wherein the lighting assembly comprises:
a plurality of lighting elements arranged concentrically about a central axis, wherein the light emitted by the lighting elements converge at a common point along the central axis.

16. The examination/visualization system of claim 14, wherein the lighting assembly comprises:
at least one lighting element comprising:
a plurality of lighting sources arranged about an inner circumference of the lighting element; and
a lighting director configured to:
direct light received by corresponding ones of the plurality of lighting sources toward at least one objective lens, wherein the at least one objective lens is configured to:
focus the received light onto a known area a known distance from the at least one objective lens.

17. A visualization system comprising:
a lighting assembly configured to:
emit light in at least one wavelength range;
a viewing device configured to:
view an enlarged image of an object located a known distance from the viewing device; and
record images of object in at least one wavelength range, the viewing device comprising:
a magnification section providing a known level of magnification, the magnification section comprising:
an objective lens; and
an eye-lens, the objective lens and eye-lens forming a first optical axis, and;
an offset section comprising:
a second eye-lens, the second eye-lens forming a second optical axis offset from the first optical axis; and
a first light director positioned at an intersection of the first axis and the second axis, the first light director comprising:
a partially reflective/partially transmissive surface, wherein the partially reflective/partially transmissive surface is configured to:
receive light associated with the object viewed through the objective lens; and
transmit a first portion of the received light toward the first eye-lens; and
reflect a remaining portion of the received light toward the second eye-lens; and
a second light director positioned within the offset section, the second light director comprising:
a second partially reflective/partially transmission surface, wherein the second partially reflective/partially transmission surface is configured to:
transmit a first portion of the remaining portion of the received light along the second optical axis toward a first image capture device; and
reflect a remaining portion of the remaining light along a third optical axis toward a second image capture device;
a processing section configured to:
receive images provided by the first image capture device and the second image capture device; and
provide the received images to a display system, wherein the display system is configured to:
display the received images on a display screen.

18. The visualization system of claim 17, wherein the first image capture device and the second image capture device are selected from a group of devices comprising one of: a digital camera, a CCD chip and a CMOS chip, wherein the selected image capture device is suitable for capturing light in at least one of: an ambient light wavelength range, a white light wavelength range, an IR wavelength range and a UV wavelength range.

19. The visualization system of claim 17, wherein the second light director comprises a filter configured to: pass light within a wavelength range less than a known wavelength and reflect light within a wavelength range greater than the known wavelength.

* * * * *